US008168168B2

(12) United States Patent
Fueyo et al.

(10) Patent No.: US 8,168,168 B2
(45) Date of Patent: May 1, 2012

(54) INFECTIVITY-ENHANCED CONDITIONALLY-REPLICATIVE ADENOVIRUS AND USES THEREOF

(76) Inventors: Juan Fueyo, Houston, TX (US); Candelaria Gomez-Manzano, Houston, TX (US)

(*) Notice: Subject to any disclaimer, the term of this patent is extended or adjusted under 35 U.S.C. 154(b) by 0 days.

(21) Appl. No.: 12/636,134

(22) Filed: Dec. 11, 2009

(65) Prior Publication Data
US 2011/0045583 A1  Feb. 24, 2011

Related U.S. Application Data

(63) Continuation of application No. 10/697,535, filed on Oct. 30, 2003, now abandoned.

(51) Int. Cl.
*C12N 15/09* (2006.01)
*C12N 15/34* (2006.01)
*C12N 7/00* (2006.01)
(52) U.S. Cl. .................. 424/93.2; 500/350; 435/91.42
(58) Field of Classification Search .................. None
See application file for complete search history.

(56) References Cited

U.S. PATENT DOCUMENTS

| 5,677,178 | A  | 10/1997 | McCormick |
| 5,801,029 | A  | 9/1998  | McCormick |
| 5,846,782 | A  | 12/1998 | Wickham et al. |
| 5,856,181 | A  | 1/1999  | McCormick |
| 6,096,718 | A  | 8/2000  | Weitzman et al. |
| 6,824,771 | B1 | 11/2004 | Curiel et al. |

FOREIGN PATENT DOCUMENTS

| WO | WO 96 17053 | 6/1996 |
| WO | WO 96 34969 | 11/1996 |
| WO | WO 98 39467 | 9/1998 |
| WO | WO 00 29599 | 5/2000 |
| WO | WO 00 56909 | 9/2000 |
| WO | WO 00 67576 | 11/2000 |
| WO | WO 01 23004 | 4/2001 |
| WO | WO 01 28569 | 4/2001 |

OTHER PUBLICATIONS

Harding et al, Molecular and Cellular Biology, Sequence-Independent Autoregulation of the Adenovirus Type 5 EIA Transcription Unit, Nov. 1985, p. 3214-3221.*
Imler et al., "Novel complementation cell lines derived from human lung carcinoma A549 cells support the growth of El-deleted adenovirus vectors," Gene Ther. 3: 75-84, 1996.
Takayama et al., "VEGF promoter-based conditionally replicative adenovirus are useful for the treatment if lung cancer," Mol. Ther. 7(5, Part 2): S420, abstract 1089.
Curiel, D.T., "Strategies to improve the therapeutic utility of conditionally replicative adenoviruses (CRAds) for cancer therapy," Proc. Aner. Assoc. Cancer Res. Ann. Meet. 43: 662-663, abstract 3287, Mar. 2002.
Adachi Y, et al., Cancer Res. Nov. 1, 2001; 61(21); 7882-7888.

NCBI Reference Sequence: GenBank Accession No. AC_000008.1, Dec. 1, 2004.
Sussenbach, J, The Structure of the Genome, The Adenoviruses (1984), Chapter 3, pp. 35-124.
Barnes, MN et al. "Conditionally Replicative Adenoviruses for Ovarian Cancer Therapy". Mol. Cancer Thera. 1:435-439 (2002).
Fueyo, J. et al. "Preclinical Characterization of the Antiglioma Activity of a Tropism-Enhanced Adenovirus Targeted to the Retinoblastoma Pathway". Journal of the National Cancer Institute 95(9):652-660 (2003).
Suzuki, K., Fueyo, J. Krasnykh, V., Reynolds, P.N., Curiel, D.T., and Alemany, R.: A Conditionally Replicative Adenovirus with Enhanced Infectivity Shows Improved Oncolytic Potency, Clin. Cancer Res., 7:120-126 (2001).
Freytag, S.O., Rogulski, K.R., Paielli, D.L., Gilbert, J.D., and Kim, J.H.: A Novel Three-Pronged Approach to Kill Cancer Cells Selectively: Concomitant Viral, Double Suicide Gene, and Radiotherapy, Human Gene Ther., 9:1323-1333 (1998).
Takayama et al., "Conditionally replicative adenovirus, AdVEGFE1 has a possibility for universal application in various cancer treatments," Mol. Ther. 5(5, Part 2): S268, abstract 821, May 2002.
Blackwell, J., et al., "Retargeting to EGFR Enhances Adenovirus Infection Efficiency of Squamous Cell Carcinoma," Arch. Otolaryngol. Head Neck Surg., 125: 856-863, 1999.
Alemany et al., "CAR-binding ablation does not change biodistribution and toxicity of adenovirus vectors," 2001, Gene Therapy 8: 1347-1353.
Alemany, R., et al., "Gene Therapy for Gliomas: Molecular Targets, Adenoviral Vectors, and Oncolytic Adenoviruses," Exp. Cell. Res., 252: 1-12, 1999.
Amalfitano, A., et al., "Improved adenovirus packaging cell lines to support the growth of replication-defective gene-delivery vectors," Proc Natl Acad Sci USA, 93: 3352-6, 1996.
Anderson, W.F., "Human Gene Therapy," Nature, 392: p. 25-30, 1998.
Babiss et al., "Cellular Promoters Incorporated into the Adenovirus Genome," 1987, J. Mol. Biol., vol. 193: 643-650.
Bangma, C.H., et al., "Free Serum Prostate-Specific Antigen and Screening for Prostate Cancer," JAMA, 275(11): 837-8, 1996.
Bischoff, J. R., et al., "An Adenovirus Mutant That Replicates Selectively in p53-Deficient Human Tumor Cells," Science, 274: 373-376, 1996.
Curiel, "Strategies to Adapt Adenoviral Vectors for Targeted Delivery," Annals New York Academy of Sciences: 158-171, 1999.
Dachs et al., "Targeting gene therapy to cancer: A Review," Oncology Res., vol. 9: 313-325. Dmitriev, I., et al., "An Adenovirus Vector with Genetically Modified Fibers Demonstrates Expanded Tropism via Utilization of a Coxsackievirus and Adenovirus Receptor-Independent Cell Entry Mechanism," J. Virol., 72(12): 9706-13, 1998.
Dobner, T., et al., "Blockage by Adenovirus E4orf6 of Transcriptional Activation by the p53 Tumor Suppresssor," Science, 272:1470-3, 1996.
Eck et al., "Gene-based therapy," Goodman & Gilman's The Pharmacological Basis of Therapeutics-Ninth Edition, McGraw-Hill:77-101, 1996.

(Continued)

*Primary Examiner* — Maria Marvich

(57) ABSTRACT

A modified adenovirus capable of overcoming the problem of low level of coxsackie-adenovirus receptor (CAR) expression on tumor cells and methods of using such adenovirus are provided. The fiber protein of the adenovirus is modified by insertion or replacement so as to target the adenovirus to tumor cells, and the replication of the modified adenovirus is limited to tumor cells due to specific promoter control or mutations in E1a or E1b genes.

1 Claim, 29 Drawing Sheets

OTHER PUBLICATIONS

Fechner, H., et al., "Expression of Coxsackie adenovirus receptor and alphav-integrin does not correlate with adenovector targeting in vivo indicating anatomical vector barriers," Gene Therapy, 6: 1520-1535, 1999.

Ferrin, L.J., "Manipulating and Mapping DNA with RecA-Assisted Restriction Endonuclease (RARE) Cleavage," Genet. Eng., 17:21-30, 1995.

Fox, "Investigation of gene therapy begins" 2000, Nature Biotechnology, vol. 18: 143-144.

Fueyo, J., et al., "A mutant oncolytic adenovirus targeting the Rb pathway produces anti-glioma effect in vivo," Oncogene, 19:2-12, 2000.

Garver R., Jr., et al., "Strategy for achieving selective killing of carcinomas," Gene Therapy, 1:46-50, 1994.

Gotoh, A., et al., "Development Of Prostate-Specific Antigen Promoter-Based Gene Therapy For Androgen-Independent Human Prostate Cancer," J. Urol., 160: 220-9, 1998.

Hardy, S., et al, "Construction of Adenovirus Vectors through Cre-lox Recombination," J. Virol., 71(3): 1842-1849, 1997.

Heise, C., et al., "ONYX-015, and E1B gene-attenuated adenovirus, causes tumor-specific cytolysis and antitumoral efficacy that can be augmented by standard chemotherapeutic agents," Nat. Med., 3:639-645, 1997.

Heise, C.C., "Efficacy of a replication-competent adenovirus (ONYX-015) following intratumoral injection: Intratumoral spread and distribution effects," Cancer Gene Therapy, 6: 499-504, 1996.

Hofmann, C., et al., "Ovine Adenovirus Vectors Overcome Preexisting Humoral Immunity against Human Adenoviruses In Vivo," J. Virol., 73: 6930-36, 1999.

Kasono, K., et al., "Selective Gene Delivery to Head and Neck Cancer Cells via an Integrin Targeted Adenoviral Vector," Clin. Cancer Res., 5: 2571-2579, 1999.

Koivunen, E., et al., "Identification of Receptor Ligands with Phage Display Peptide Libraries," J. Nucl. Med., 40: 883-888, 1999.

Krasnykh, V., et al., "Characterization of an Adenovirus Vector Containing a Heterologous Peptide Epitope in the HI Loop of the Fiber Know," J. Virol., 72(3): 1844-52, 1998.

Krasnykh, V., et al., "Generation of Recombinant Adenovirus Vectors with Modified Fibers for Altering Viral Tropism," J. Virol., 70: 6839-6846, 1996.

Laquerre et al., "Recombinant Herpes Simplex Virus Type 1 Engineered for Targeted Binding to Erythropoietin Receptor-Bearing Cells," 1998, Journal of Virology, vol. 72, No. 12:9683-9697.

Leissner et al., "Influence of adenoviral fiber mutations on viral encapsidation, infectivity and in vivo tropism," 2001, Gene Therapy 8: 49-57.

Miller, C.R., et al., "Differential Susceptibility of Primary and Established Human Glioma Cells to Adenovirus Infection: Targeting via the Epidermal Growth Factor Receptor Achieves Fiber Receptor-independent Gene Transfer," Cancer Res., 58: 5738-48, 1998.

Moran, E., "Interaction of adenoviral proteins with pRB and p53," Faseb J, 7: 880-5, 1993.

O'Riordan, C., et al., "PEGylation of Adenovirus with Retention of Infectivity and Protection from Neutralizing Antibody in Vitro and in Vivo," Human Gene Therapy, 10: 1349-1358, 1999.

Pasqualini, R., et al., "αv Integrins as receptors for tumor targeting by circulating ligands," Nat. Biotechnol., 15: 542-6, 1997.

Peng et al., "Viral vector targeting," 1999, Current Opinion in Biotechnology, 10: 454-457.

Raben, D., et al., "Enhancement of radiolabeled antibody binding and tumor localization through adenoviral transduction of the human carcinoembryonic antigen gene," Gene Therapy, 3:567-80, 1996.

Rajotte, Molecular Heterogeneity of the Vascular Endothelium Revealed by in Vivo Phage Display, 1998, J. Clin. Invest. vol. 102: 430-437.

Roelvink, P. W., et al., "Identification of a Conserved Receptor-Binding Site on the Fiber Proteins of CAR-Recognizing Adenoviridae," Science, 286: 1568-1571, 1999.

Roelvink et al., "The coxsachievirus-adenovirus receptor protein can function as a cellular attachment protein for adenovirus serotypes from subgroups A, C, D, E, and F," J. Virol., vol. 72(10): 7909-7915.

Rokhlin, O.W., et al., "Expression of Cellular Adhesion Molecules on Human Prostate Tumor Cell Lines," Prostate, 26: 205-212, 1995.

Sandhu et al., "Human Gene Therapy," Critical Reviews in Biotechnol., vol. 17(4): 307-326.

Shi, Q., et al., "Modulation of the Specificity and Activity of a Cellular Promoter in an Adenoviral Vector," Human Gene Therapy, 8: 403-10, 1997.

Shinoura, N., et al., "Highly Augmented Cytopathic Effect of a Fiber-mutant E1B-defective Adenovirus for Gene Therapy of Gliomas," Cancer Res., 59: 3411-3406, 1999.

Stevenson, S., et al., "Human Adenovirus Serotypes 3 and 5 Bind to Two Different Cellular Receptors via the Fiber Head Domain," J. Virol., 69: 2850-2857, 1995.

Todo, T., et al., "Systemic Antitumor Immunity in Experimental Brain Tumor Therapy Using a Multimutated, Replication-Competent herpes Simplex Virus," Human Gene Therapy, 10: 2741-2755, 1999.

Vanderkwaak et al., "Adenovirus with RGD-modified fiber demonstrates improved gene transfer into ovarian carcinoma cell lines and ovarian primary tumors," Gynecologic Oncology, vol. 72(3):505, 1999.

Von Seggern et al., "Adenovirus Vector Pseudotyping in Fiber-Expressing Cell Lines: Improved Transduction of Epstein-Barr Virus-Transformed B Cells," J. Virol., 74: 354-362, 2000.

Wildner, O., et al., "Adenoviral vectors capable of replication improve the efficacy of HSVtk/GCV suicide gene therapy of cancer," Gene Therapy, 6: 57-62, 1999.

Wildner, O., et al., "Therapy of Colon Cancer with Oncolytic Adenovirus Is Enhanced by the Addition of Herpes Simplex Virus-thymidine kinase," Cancer Res., 59: 410-413, 1999.

Yang, Y., et al., "Recombinant IL-12 prevents formation of blocking IgA antibodies to recombinant adenovirus and allows repeated gene therapy to mouse lung," Nat. Med., 1: 890-893, 1995.

Yeh, P., et al., "M., Advances in adenoviral vectors: from genetic engineering to their biology," FASEB J, 11: 615-23, 1997.

Yu, D. C., et al., "Identification of the Transcriptional Regulatory Sequences of Human Kallikrein 2 and Their Use in the Construction of Calydon Virus 764, an Attenuated Replication Competent Adenovirus for Prostate Cancer Therapy", Cancer Res., 59: 1498-1504, 1999.

Yu, D., et al., "Enhanced c-erbB-2/neu Expression in Human Ovarian Cancer Cells Correlates with More Severe Malignancy that can be Suppressed by E1A", Cancer Res., 53: 891-8, 1993.

Zhang, J., et al., "Vectors For Cancer Gene Therapy," Cancer Metastasis Rev., 15: 385-401, 1996.

Forsythe JA, et al., "Activation of vascular endothelial growth factor gene transcription by hypoxia-inducible factor 1," Mol Cell Biol. Sep. 1996;16(9):4604-13.

He TC, et al., "A simplified system for generating recombinant adenoviruses," Proc Natl Acad Sci U S A. Mar. 3, 1998;95(5):2509-14.

Ohta Y, et al., "Significance of vascular endothelial growth factor messenger RNA expression in primary lung cancer," Clin Cancer Res. Aug. 1996;2(8):1411-6.

Takayama K, et al., "The levels of integrin alpha v beta 5 may predict the susceptibility to adenovirus-mediated gene transfer in human lung cancer cells," Gene Ther. Mar. 1998;5(3):361-8.

Takayama K, et al., "Suppression of tumor angiogenesis and growth by gene transfer of a soluble form of vascular endothelial growth factor receptor into a remote organ," Cancer Res. Apr. 15, 2000;60(8):2169-77.

* cited by examiner

SEQUENCE LISTING

<160> NUMBER OF SEQ ID NOS: 12

<210> SEQ ID NO 1

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Cys Asp Cys Arg Gly Asp Cys Phe Cys
1               5

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
caaacgctgt tggatttatg                                              20

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
gtgtaagagg atgtggcaaa t                                            21

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
attaccgaag aaatggccgc                                              20

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
ccatttaaca cgccatgca                                               19

<210> SEQ ID NO 6
<211> LENGTH: 24
<212> TYPE: DNA
<213> ORGANISM: Artificial Sequence
<220> FEATURE:
<223> OTHER INFORMATION: Synthetic primer

<400> SEQUENCE: 6
gaagtggtga agttcatgga tgtc                                         24

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
```

```
cgatcgttct gtatcagtct ttcc                                          24

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
ccttcattga cctcaacta                                                19

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ggaaggccat gccagtgagc                                               20

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
tgacacgcat actcggagct a                                             21

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tttgagcagc accttgcatt                                               20

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
cgccgcccat gcaacaagct t                                             21
```

INFECTIVITY-ENHANCED CONDITIONALLY-REPLICATIVE ADENOVIRUS AND USES THEREOF

CROSS-REFERENCE TO RELATED APPLICATION

This application is a continuation of prior application U.S. Ser. No. 10/697,535, filed on Oct. 30, 2003, now abandoned, which claims the benefit of priority to U.S. Ser. No. 09/569, 789, filed May 12, 2000, now U.S. Pat. No. 6,824,771, which claims benefit of provisional patent application Ser. No. 60/133,634, filed May 12, 1999, wherein each application is hereby incorporated by reference in its entirety.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to adenoviral vectors. More specifically, the present invention relates to infectivity-enhanced conditionally replicative adenovirus vectors.

2. Description of the Related Art

Surgery, chemotherapy and radiotherapy constitute the conventional therapies in clinical use to treat cancer. These therapies have produced a high rate of cure in early-stage cancer, but most late-stage cancers remain incurable because they cannot be resected or the dose of radiation or chemotherapy administered is limited by toxicity to normal tissues. An alternative promising approach is the transfer of genetic material to tumor or normal cells as a new therapy itself or to increase the therapeutic index of the existing conventional therapies. In this regard, three main strategies have been developed to accomplish cancer gene therapy: potentiating immune responses against tumors, eliciting direct toxicity to tumors, and compensating the molecular lesions of tumor cells.

To achieve the high level of gene transfer required in most cancer gene therapy applications, several viral and non-viral vectors have been designed. Adenoviral vectors have been used preferentially over other viral and non-viral vectors for several reasons, including infectivity of epithelial cells, high titers, in vivo stability, high levels of expression of the transgene, gene-carrying capability, expression in non-dividing cells, and lack of integration of the virus into the genome. In most of the adenoviral vectors used in cancer gene therapy, the transgene substitutes for the early 1 region (E1) of the virus. The E1 region contains the adenoviral genes expressed first in the infectious stage and controls expression of the other viral genes. The early region 3 (E3) gene codes for proteins that block a host's immune response to viral-infected cells and is also usually deleted in vectors used for cancer gene therapy, particularly in immunopotentiating strategies.

E1-substituted, E3-deleted vectors can carry up to 8 kb of non-viral DNA, which is sufficient for most gene therapy applications. E1-substituted, E3-deleted vectors are propagated in packaging cell lines that transcomplement their E1-defectiveness, with production yields of up to 10,000 virion particles per infected cell, depending upon the transgene and its level of expression in the packaging cell. Not all of the viral particles are able to transduce cells or to replicate in the packaging cell line, so bioactivity of a particular vector has been defined as the ratio of functional particles to total particles. This bioactivity varies from 1/10 to 1/1000, depending not only upon the vector, but also upon the methods of purification and quantification. The titer used is the concentration of functional particles, which can be as high as $10^{12}$ per milliliter.

One problem encountered when propagating these vectors to high titers is the recombination of vector sequences with the E1 sequences present in the packaging cell line, thereby producing replication-competent adenoviruses (RCA). This problem has been solved by using packaging cell lines where the E1 gene does not overlap with the vector sequences.

The current generation of adenoviral vectors are limited in their use for cancer gene therapy, primarily for three reasons: (1) the vectors are cleared by the reticuloendothelial system; (2) the vectors are immunogenic; and (3) the vectors infect normal cells. The problem of filtration by the reticuloendothelial system cells such as macrophages of the spleen or Kupffer cells of the liver affects adenoviral vectors as well as other viral and non-viral vectors and limits their utility in intravascular administration. The early and late viral genes that remain in E1-E3 deleted vectors may also be expressed at low, but sufficient enough levels such that the transduced cells are recognized and lysed by the activated cytotoxic T lymphocytes. Additionally, a higher viral dose must be injected to reach the entire tumor before a neutralizing immune response develops. The major limitation then becomes the amount of vector that can be safely administered, which will depend upon the capacity of the vector to affect tumor cells without affecting normal cells.

The limitations of adenoviral vectors at the level of infectivity is two-fold. On the one hand, human clinical trials with adenoviral vectors have demonstrated relatively inefficient gene transfer in vivo. This has been related to the paucity of the primary adenovirus receptor, coxsackie-adenovirus receptor (CAR), on tumor cells relative to their cell line counterparts. On this basis, it has been proposed that gene delivery via CAR-independent pathways may be required to circumvent this key aspect of tumor biology. On the other hand, adenoviral vectors efficiently infect normal cells of many epithelia. This results in the expression of the transgene in normal tissue cells with the consequent adverse effects. This problem has been addressed by targeting adenoviral vectors to tumor cells at the level of receptor interaction and transgene transcription.

Targeting adenoviral vectors to new receptors has been achieved by using conjugates of antibodies and ligands, in which the antibody portion of the conjugate blocks the interaction of the fiber with the CAR receptor and the ligand portion provides binding for a novel receptor. Receptor targeting has also been achieved by genetic modification of the fiber.

Transcriptional targeting of adenoviral vectors has been demonstrated using tumor-antigen promoters or tissue-specific promoters to control the expression of the transgene. However, these promoters can lose their specificity when inserted in the viral genome and, depending upon the level of toxicity of the transgene, even low levels of expression can be detrimental to normal cells. Thus, for cancer gene therapy, the major issues limiting the utility of adenoviral vectors are the efficiency and specificity of the transduction.

A major limitation found in the use of adenoviral vectors in the clinical setting is the number of tumor cells that remain unaffected by the transgene. A vector that propagates specifically in tumor cells, results in lysis and subsequently allows for transduction of neighbor cells by newly produced virions will increase the number of tumor cells affected by the transgene. A good replicative vector should be weakly pathogenic or non-pathogenic to humans and should be tumor-selective. Efforts have been aimed at improving the safety of replication-competent adenoviruses with the goal of being able to administer much higher doses. One strategy is to transcomplement the E1 defect with an E1-expression plasmid conjugated into the vector capsid, which allows a single round of replication thereby producing a new E1-substituted vector with the ability of local amplification and subsequent gene transduction.

Other strategies are designed to obtain vectors that replicate continuously and whose progeny are also able to replicate, but are incapable of propagating in normal cells. In this regard, two approaches have been described that render adenovirus propagation selective for tumor cells: (1) deletions, and (2) promoter regulation. Adenoviral mutants unable to inactivate p53 propagate poorly in cells expressing p53 but efficiently in tumor cells where p53 is already inactive. Based upon this strategy, an adenovirus mutant in which the E1b-55k viral protein was deleted and was unable to bind to p53 was effective in eliminating tumors in preclinical models and is in clinical trials. Controlling viral replication by substituting a viral promoter, such as the E1a promoter, with a tumor associated-antigen promoter, such as the alpha-fetoprotein promoter or the prostate antigen promoter, has been demonstrated, and specific lysis of tumors transfected with an adenovirus vector expressing either of the abovementioned promoters was demonstrated in murine models.

Both approaches have limitations, however. The fact that other viral proteins besides E1b-55K also interact with p53, and because p53 can be necessary for the active release of virus in the later stages of infection may affect the specificity of the vector. Another caveat results from using E1a as the only controlled viral gene since E1a-like activity has been found in many tumor cell lines. Furthermore, the actual specificity of the above-mentioned promoters for cancer cells, and the fact that promoters inserted in the viral genome can lose their expression specificity are factors that hindered clinical applications of this approach.

Therefore, new methods are clearly needed to achieve more selective therapeutic effects of replication-competent adenoviruses. For these vectors, in parallel to what has been achieved with non-replicative vectors, modification of viral tropism could enhance tumor transduction and tumor selectivity at the level of cell entry, and in this way realize the full potential of replicative vectors for cancer gene therapy.

The prior art is deficient in adenoviral vectors that are specific for a particular cell type (i.e., do not infect other cell types) and that replicate with high efficiency in only those particular cell types. The present invention fulfills this long-standing need in the art.

SUMMARY OF THE INVENTION

Adenoviral vectors have been widely employed in cancer gene therapy. Their high titers, structural stability, broad infectivity, high levels of transgene expression, and lack of integration have contributed to the utility of this vector. In this regard, adenoviral vectors have been used to transfer a variety of genes such as cytokines, tumor suppresser genes, pro-drug converting genes, antisense RNAs and ribozymes to inhibit the expression of oncogenes, antiangiogenic genes, etc. Despite the promise of adenoviral vectors, results from experimental models and clinical trials have been less than optimal.

Within this context, several specific limitations have been identified. One limitation lies in the poor infectability of primary tumors due to low levels of the primary adenovirus receptor CAR. A second limitation that particularly affects the efficiency of replicative vectors is related to the lack of tumor-specific replication achieved using promoters or mutations. The present invention describes methods to increase adenovirus infectivity based upon modification of the virus tropism. The present invention demonstrates that modification of the adenovirus fiber by genetic manipulation increases infectivity of primary tumors several orders of magnitude due to CAR-independent gene transfer. In addition, selective replication in tumors is described herein, and represents a safe and effective means to lyse and transduce tumors. The present invention further describes a strategy based upon control of the expression of one or more essential early viral genes using tumor-specific promoters.

It is a goal of the present invention to improve the infectivity and specificity of conditional replicative vectors, thereby improving their therapeutic utility and efficacy.

One object of the present invention is to provide adenoviral vectors that possess enhanced infectivity to a specific cell type (i.e., that are not limited to CAR-dependent cell entry) and that replicate with high efficiency in only those cell types.

In one embodiment of the present invention, there is provided an infectivity-enhanced conditionally-replicative adenovirus. This adenovirus possesses enhanced infectivity towards a specific cell type, which is accomplished by a modification or replacement of the fiber of the adenovirus. The modification is accomplished by introducing a fiber knob domain from a different subtype of adenovirus, introducing a ligand into the HI loop of the fiber knob, or replacing the fiber with a substitute protein which presents a targeting ligand. Additionally, the adenovirus has at least one conditionally regulated early gene, such that replication of the adenovirus is limited to the specific cell type.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1 shows that an anti-knob Fab-FGF2 conjugate enhances cell transduction.

FIG. 3 shows the HI loop of the fiber as a domain to insert ligand for retargeting adenoviruses.

FIG. 11 shows that six days post-infection, cells were lysed and the amount of virus in the lysates was measured by plaque assay in 293 cells (for WT and dl312) or W162 cells (for dl1014).

FIG. 12 shows the analyses of adenoviral DNA.

FIG. 14 shows cell viability analyzed with an XTT colorimetric assay. In both cell lines, Ad5-D24RGD had higher lytic potency than did its unmodified counterpart, as shown by the percentage of viable cells remaining in the corresponding treatment conditions.

FIG. 15 shows in vivo oncolysis by high and low doses of infectivity-enhanced CRAds.

DETAILED DESCRIPTION OF THE INVENTION

Figure 1A:
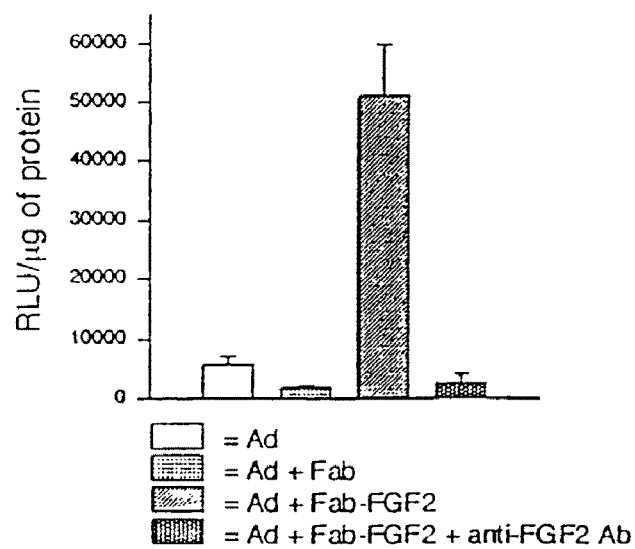
FIG. 1A shows that AdCMVluc ($5 \times 10^7$ pfu) was preincubated with 1.44 µg of Fab or 1.94 µg of Fab-FGF2. SKOV3 cells (24,000 cells per well in 24-well plates) were infected with control vector or with the vector complexes (MOI of 50) Inhibition was performed by adding a polyclonal anti-FGF2 to the complex before infection. Luciferase activity in cell lysates was assayed 24 h after infection. The mean of triplicate experiments is shown.

The present invention addresses the two major limitations of replicative adenoviral agents (viruses and vectors) in their application to cancer gene therapy, i.e., the efficacy of transduction and the specificity of replication. Adenovirus binds to the coxsackie-adenovirus receptor, CAR, in the cellular membrane using the C-terminal globular domain of the viral fiber, the knob. Since a limited amount of coxsackie-adenovirus receptor is present in tumors, one means to enhance infectivity would be to provide additional binding pathways. Therefore, two methods have been developed to modify adenovirus binding. The first method uses a Fab fragment of an anti-knob antibody conjugated to a ligand of a cellular receptor, while the second method comprises direct genetic modification of the knob sequence.

One important advantage of direct genetic modification is that the progeny will carry the modified fiber, thereby retaining the replicative virus, enhanced infectivity trait through the amplification cycles. Wickman et al. (1997) have generated adenoviruses with chimeric fibers in which the ligand is connected to the carboxyl terminal position of the fiber. This carboxyl terminal location is not always appropriate because the addition of more than 20-30 heterologous amino acid residues can result in the loss of fiber trimerization and binding to the capsid. Furthermore, the three-dimensional structure of the fiber indicates that the carboxyl terminal end points towards the virion, and therefore, away from the cell surface. For these reasons, the HI loop was used herein as an exposed and amenable site for the incorporation of exogenous sequences.

It has been recognized that the major limitation in several strategies of cancer gene therapy resides in the need to transduce the majority of cells of a tumor. With the exception of a limited bystander effect described in some strategies, the cells that are left untransduced will jeopardize and reduce any therapeutic effect. Adenoviral vectors are limited in this regard by the paucity of its receptor, CAR, in tumors. It is a goal of the present invention to improve the infectivity of adenoviral vectors by providing additional pathways to cell binding besides CAR. Previous data has shown that modification of the HI loop of the fiber is a feasible strategy to add new ligand motifs into the fiber. An RGD motif has already been incorporated into the fiber of regular E1-deleted vectors and been shown to enhance the therapeutic effects in vivo.

With regard to the efforts to increase the specificity at the level of virus replication, methods have been developed to confer regulated-replication or conditional-replication competency to adenoviral vectors based upon complementing, in trans, the essential early genes that are missing in the replication-defective vectors. In this way, E1-deleted and E4-deleted vectors have been transcomplemented by conjugating them to E1 or E4 expression plasmids. This method enables the vectors to replicate, thereby augmenting their transduction ability. Methods have also been explored that allow the continuous replication of the vector, such as using the E1a-like activity provided by interleukin 6 to enable replication of E1a-deleted vectors.

The present invention further describes methods to enhance the specificity of the replication of these replicative adenoviral vectors. The current methods of mutating E1, or regulation of E1 with tumor-specific promoters, are both very rational approaches, but may prove not selective enough for several reasons. In the case of E1 deletions, the main limitation lies in incomplete knowledge of the role of these proteins in the viral replicative cycle and in controlling the cell cycle. For example, adenovirus may use a p53-dependent mechanism to release the progeny from the infected cell. This would predicate a positive role for p53 in virus production and would reduce the yields of virus in p53-deficient cells. On the other hand, other viral proteins besides E1-55K may block p53 function, such as E4, and this would allow the 55K⁻ to replicate in p53+ cells. In any case the specificity of a 55K⁻ for p53-defective cells is controversial. Regarding to strategies based on regulation of E1 it is a concern that promoters can lose certain degree of specificity when inserted into the viral genome. The presence of E1-like activity in uninfected cells could also pose a problem for the specificity achieved with both vectors. In this regard, some replication of E1 vectors has been observed in many different cell lines.

Therefore, it is desirable to improve the replication selectivity of replicative adenoviral vectors for tumors by achieving tumor-selective regulation of key early genes other than E1, such as E2 or E4. An adenovirus-polylysine-DNA transcomplementation system has been developed as a means to evaluate replication. This replication-enabling system is used to analyze the efficacy and specificity of tumor-specific replication mechanisms based on the regulation of the E4 or E2 genes. In the transcomplementation system, plasmids encoding E2 or E4 under the control of different tumor-specific promoters are used to screen for mechanisms that confer selective replication. Ultimately, selective replication will involve the incorporation of the regulated E4 or E2 into the viral genome to achieve continuous replication. Accordingly, after the tumor-selective replication has been demonstrated, these regulatory mechanisms are incorporated into a single viral vector. Optimally, these regulatory mechanisms are combined with the fiber modification described herein to enhance infectivity.

Initial tumor models are based on cell lines with differential expression of the PSA protein: LNCaP and DU145. Tumors derived from lung adenocarcinoma cell lines and ovarian cell lines are used to evaluate viruses with promoters such as Carcinoembryonic antigen (CEA) or secretory leukoprotease inhibitor (SLPI). Therapeutic effects are only observed in tumors derived from the cell lines that allow the expression of the tumor-specific controlled E4 or E2, that is, replication of the virus. In these permissive cell lines, higher therapeutic advantage is observed for the RGD-modified virus relative to the unmodified virus.

The present invention is directed towards an infectivity-enhanced conditionally replicative adenovirus. This adenovirus possesses enhanced infectivity towards a specific cell type, which is accomplished by a modification or replacement of the fiber of a wildtype adenovirus and results in enhanced infectivity relative to the wildtype adenovirus. The adenovirus also has at least one conditionally regulated early gene, such that replication of the adenovirus is limited to the specific cell type. Preferably, the cell is a tumor cell.

Preferably, the modification or replacement of the fiber results in CAR-independent gene transfer. Generally, the modification is accomplished by introducing a fiber knob domain from a different subtype of adenovirus. The fiber can also be modified by introducing a ligand into the HI loop of the fiber knob, or replacing the fiber with a substitute protein which presents a targeting ligand. Representative ligands include physiological ligands, anti-receptor antibodies and cell-specific peptides. Additionally, the ligand may comprise a tripeptide having the sequence Arg-Gly-Asp (RGD), or more specifically, a peptide having the sequence CDCRGD-CFC (SEQ ID NO:1).

Generally, the fiber substitute protein associates with the penton base of the adenovirus. Structurally, the fiber substitute protein is preferably a rod-like, trimeric protein. It is desirable for the diameter of the rod-like, trimeric protein to be comparable to the native fiber protein of wild type adenovirus. It is important that the fiber substitute protein retain trimerism when a sequence encoding a targeting ligand is incorporated into the carboxy-terminus. In a preferred aspect, a representative example of a fiber substitute protein is T4 bacteriophage fibritin protein. In a preferred embodiment, the fiber substitute protein comprises: a) an amino-terminal portion comprising an adenoviral fiber tail domain; b) a chimeric fiber substitute protein; and c) a carboxy-terminal portion comprising a targeting ligand. More generally, the fiber substitute protein can be selected from the group consisting of trimeric structural proteins, trimeric viral proteins and trimeric transcription factors. Other representative examples of fiber substitute proteins include isoleucine trimerization motif and neck region peptide from human lung surfactant D.

Preferably, the fiber substitute protein has a coiled coil secondary structure. The secondary structure provides stability because of multiple interchain interactions. The fiber substitute protein does not have to be a natural protein. In fact, a person having ordinary skill in this art would be able to construct an artificial protein. Preferably, such an artificial fiber substitute protein would have a coiled coil secondary structure.

The early gene may be conditionally regulated by means consisting of a tissue-specific promoter operably linked to an early gene (e.g., E1, E2 and/or E4) and a mutation in an early gene (e.g., E1, E2 and/or E4). Representative tissue-specific promoters are derived from genes encoding proteins such as the prostate specific antigen (PSA), Carcinoembryonic antigen (CEA), secretory leukoprotease inhibitor (SLPI), alpha-fetoprotein (AFP), vascular endothelial growth factor, CXCR4 or survivin.

Additionally, the adenovirus may carry a therapeutic gene in its genome. In conjunction with the above-mentioned adenoviral vector, a method of providing gene therapy to an individual is disclosed herein, comprising the steps of: administering to the individual an effective amount of an infectivity-enhanced conditionally-replicative adenovirus. Representative routes of administration are intravenously, intraperitoneally, systemically, orally and intratumorally. Generally, the individual has cancer and the cell is a tumor cell. When the therapeutic gene carried by the adenovirus is, for instance, a herpes simplex virus thymidine kinase gene, the present invention further provides for a method of killing tumor cells in an individual, comprising the steps of: pretreating the individual with an effective amount of an infectivity-enhanced conditionally-replicative adenovirus expressing the TK gene; and administering ganciclovir to the individual. Generally, the individual has cancer.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "vector" is a replicon to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

As used herein, the terms "conditionally regulated" and "conditionally-replicative" refer to the expression of a viral gene or the replication of a virus or a vector, wherein the expression of replication is dependent (i.e., conditional) upon the presence or absence of specific factors in the target cell.

As used herein, the term "early genes" refers to those adenoviral genes expressed prior to the onset of adenoviral DNA replication.

As used herein, the term "CAR-independent infectivity" refers to the entry of adenovirus into a cell by receptors different from the coxsackie-adenovirus receptor (CAR).

As used herein, the term "RGD-integrin interaction" refers to binding of the arginine-glycine-aspartic acid (RGD) residues in a peptide to integrin receptor molecules.

As used herein, the term "replication-competent adenoviruses" refers to an adenovirus capable of replication (i.e., an adenovirus that yields progeny).

As used herein, the term "fiber substitute protein" is a protein that substitutes for fiber and provides three essential features: trimerizes like fiber, lacks adenoviral tropism and has novel tropism.

When used in vivo for therapy, the adenovirus of the present invention is administered to the patient or an animal in therapeutically effective amounts, i.e., amounts that eliminate or reduce the tumor burden. A person having ordinary skill in this art would readily be able to determine, without undue experimentation, the appropriate dosages and routes of administration of this adenovirus of the present invention. It may be administered parenterally, e.g. intravenously, but other routes of administration will be used as appropriate. The dose and dosage regimen will depend upon the nature of the cancer (primary or metastatic) and its population, the characteristics of the particular immunotoxin, e.g., its therapeutic index, the patient, the patient's history and other factors. The amount of adenovirus administered will typically be in the range of about $10^{10}$ to about $10^{11}$ viral particles per patient. The schedule will be continued to optimize effectiveness while balanced against negative effects of treatment. See Remington's Pharmaceutical Science, 17th Ed. (1990) Mark Publishing Co., Easton, Pa.; and Goodman and Gilman's: The Pharmacological Basis of Therapeutics 8th Ed (1990) Pergamon Press; which are incorporated herein by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Figure 1B:
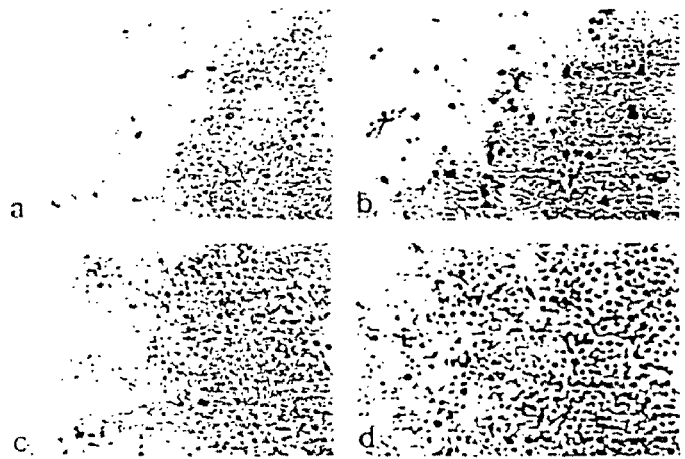
FIG. 1B shows that AdCMVLacZ was complexed with Fab-FGF2 conjugate as in FIG. 1A. SKOV3 cell were infected with control vector (a, c) or complexed vector (b, d) at MOI of 5 (a, b) or 50 (c, d) and stained with X-gal 24 h after infection.

Enhanced Tumor Transduction with Adenoviral Vectors Modified with an Antibody Conjugate As a first approach towards enhancing the infectivity of adenoviral vectors and to demonstrate the tumor transduction advantage of vectors with altered tropism over unmodified vectors, an anti-fiber antibody conjugated to fibroblast growth factor (FGF2) was used. The Fab portion of the anti-knob antibody, 1D6.14, which is capable of blocking the interaction of the fiber with its cognate cellular receptor, was chemically conjugated to FGF2. The resulting Fab-FGF2 conjugate was complexed with adenoviral vectors expressing luciferase or β-galactosidase reporter genes to compare the transduction efficiency of the modified and unmodified vectors. Vector modification increased the level of gene expression more than 9-fold, as measured by luciferase activity (FIG. 1A), largely due to transduction of a greater percentage of target cells as seen by β-galactosidase staining (FIG. 1B). This experiment clearly demonstrates that a retargeted adenoviral vector can overcome the inefficacious transduction observed in certain cell lines transduced poorly by adenoviral vectors.

Figure 2:
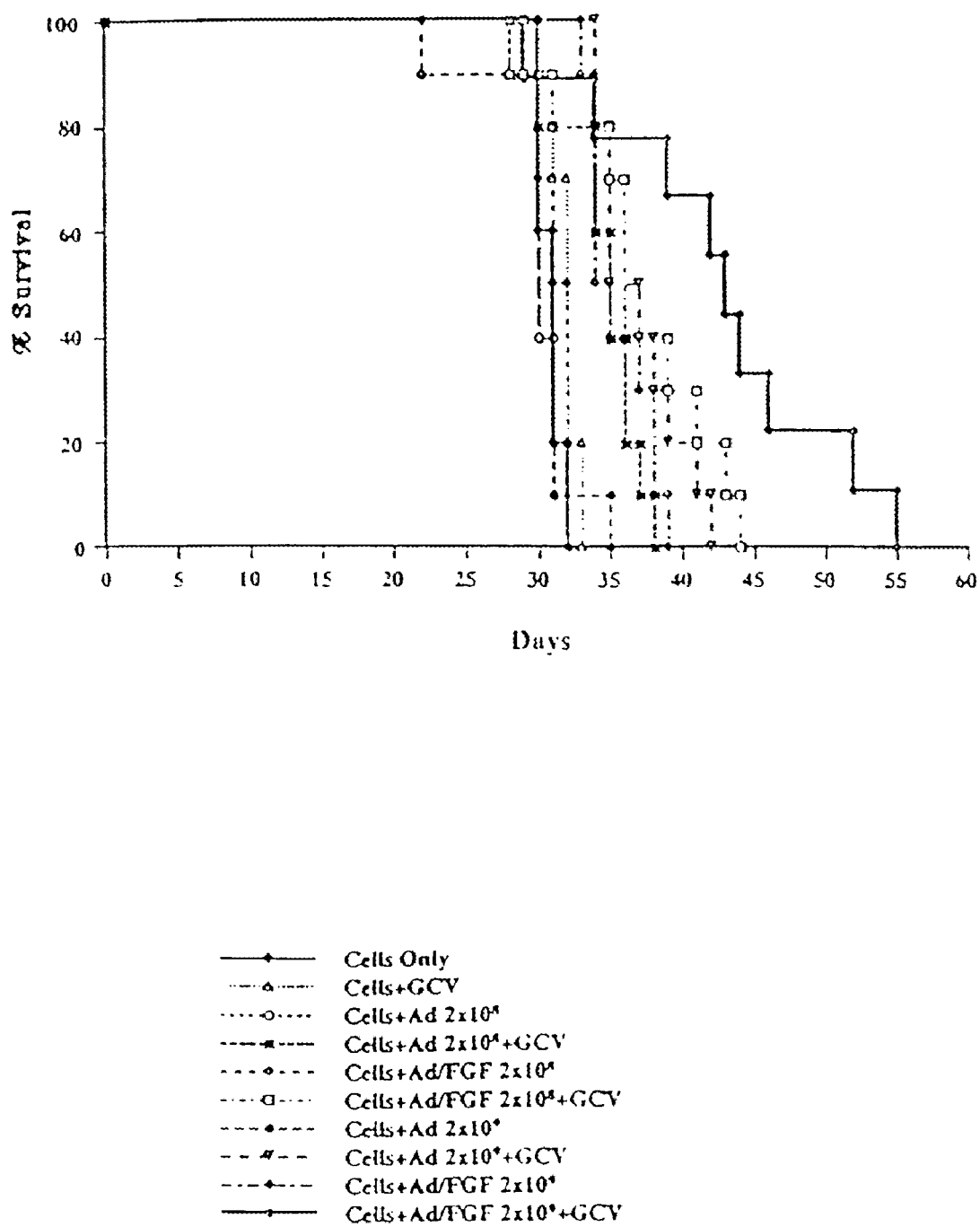
FIG. 2 shows that Fab-FGF2 retargeting augments in vivo therapeutic benefit of the AdCMVHSV-TK vector. Five days after i.p. inoculation of $2 \times 10^7$ SKOV3 cell in SCID mice, $2 \times 10^8$ or $2 \times 10^9$ pfu of AdCMVTK alone or complexed with FGF2 were injected i.p. Forty eight h later, half of the-mice were treated with GCV (50 mg/kg body weight) for 14 days. Survival was monitored daily.

To compare the therapeutic effect of an PGF2-modified vector to an unmodified vector in established tumors, the conjugate was then mixed with an adenovirus expressing HSV-TK (AdCMVHSV-TK). Treatment of SKOV3 ovarian carcinomas established in nude mice with the modified vector followed by administration of the prodrug, ganciclovir, resulted in a significant prolongation of survival when compared with the unmodified vector plus ganciclovir (FIG. 2). Thus, retargeting can increase the in vivo therapeutic effect of adenoviral vectors against tumors. It is clear that the infectivity of tumors by unmodified adenovirus is not optimal and modification of the capsid to alter the tropism of the virus is a direct approach to increase this infectivity.

Example 2

Figure 3A:
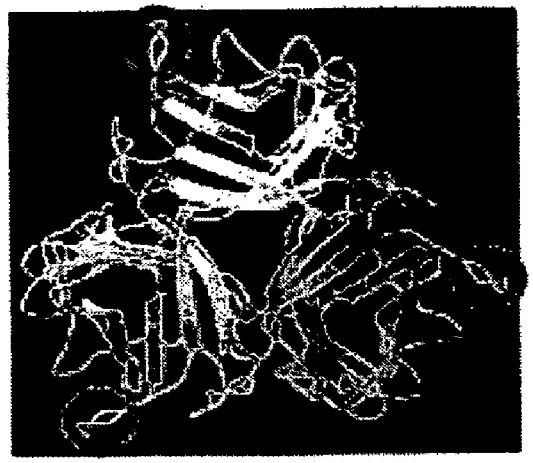
FIG. 3A shows the knob trimer viewed along the three-fold symmetry axis (Reproduced from Xia et al. [42]).
Figure 3B:
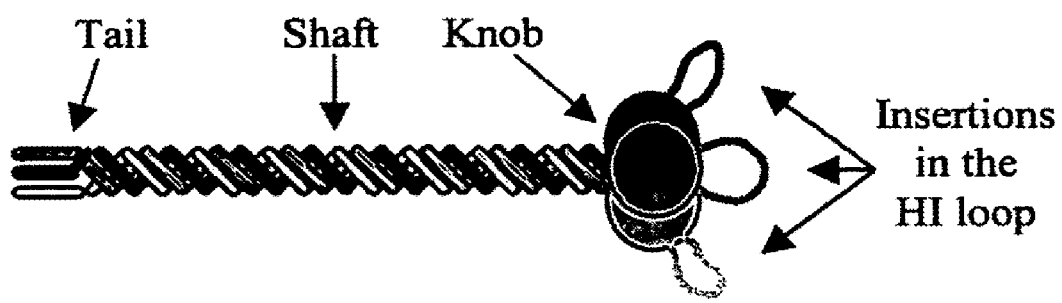
FIG. 3B shows the localization of targeting ligands within the fiber molecule.

Genetic Modification of the HI Loop of the Fiber Provides Enhanced Infectivity to Adenoviral Vectors The Fab-ligand conjugation method described in Example 1 only modifies the tropism of the vector prepared for inoculation. In the context of a replicative vector, it is advantageous to modify the tropism of the vector that replicates in the tumor as well. With this rationale, a genetic modification of the fiber is necessary for replicative vectors because it is carried over to the progeny. As a simple and potent strategy for retargeting, the sequence of the fiber was genetically modified. Based on the three-dimensional model of the fiber knob, targeting ligands were inserted into the HI loop of the fiber (FIG. 3). This loop is flexible, exposed on the outside of the knob, is not involved in fiber trimerization and its variable length in different Ad serotypes suggests that insertions or substitutions would not affect the fiber stability.

As a ligand to introduce into the HI loop of the fiber knob, the sequence coding for an RGD peptide, CDCRGDCFC (SEQ ID NO:1), was chosen. This RGD sequence is known to target tumors by binding with high affinity to several types of integrins. It was hypothesized that an adenoviral vector able to bind via fiber-RGD/integrin interaction would not depend upon the presence of the CAR receptor in tumors to be effective, and would therefore target tumors more efficiently than the unmodified vector counterpart.

The DNA sequence encoding the peptide was cloned into the EcoRV site of the knob domain in a plasmid containing the fiber sequence. The wild type fiber of an E1,E3-deleted adenoviral vector expressing the luciferase gene, AdCMV-Luc, was replaced with the RGD-modified fiber by homologous recombination in bacteria. After homologous recombination, the genome of the new adenoviral vector was released from the plasmid backbone by digestion with PacI. To use the firefly luciferase gene, the internal PacI site of this gene was eliminated by introducing a silent mutation. The plasmid obtained as a result of these DNA recombinations was then utilized for transfection of 293 cells to rescue Ad5IucRGD. The presence of RGD in the virus was confirmed by PCR as well as by cycle sequencing of viral DNA isolated from CsCl-purified virions of Ad5lucRGD.

To demonstrate that the genetic modification of the fiber was able to confer CAR-independent infectivity to the modified vector, the unmodified AdCMVLuc and the modified Ad5lucRGD vectors were used to transduce 293, HUVEC, and RD cell lines, which express high, moderate, and low levels of CAR respectively. The CAR-independent infection was further analyzed using competitive inhibition by recombinant Ad5 fiber knob protein known to efficiently block virus binding to CAR receptor. Luciferase expression in 293 cells mediated by the unmodified virus, AdCMVLuc, was efficiently blocked by recombinant knob protein. Depending on the multiplicity of infection (MOI) used, knob protein blocked 85% to 93% of luciferase activity in AdCMVLuc-transduced cells. In contrast, the same concentration of knob was able to block only 40% to 60% of Ad5lucRGD-mediated gene expression in 293 cells, indicating that in addition to the fiber-CAR interaction utilized by the wild type Ad5, Ad5lucRGD is capable of using an alternative, CAR-independent, cell entry pathway. Of note, the contribution of that alternative mechanism of cell binding was quite significant, providing 40% to 60% of overall gene transfer to 293 cells. Luciferase expression in HUVEC cells transduced with Ad5lucRGD was about 30-fold higher than with AdCMV-Luc. The effect of Ad5 fiber knob on AdCMVluc-mediated transduction was less dramatic than in 293 cells, consistent with a relative lack of CAR in the HUVEC. Most importantly, recombinant knob protein did not inhibit the levels of luciferase expression directed by Ad5lucRGD. The luciferase activity detected in RD cells transduced with AdCMVluc was extremely low: at an MOI of one pfu/cell, it was almost equal to the background level of mock-infected cells. In contrast, the level of transgene expression achieved with Ad5lucRGD was 16- to 47-fold higher than with AdCMVLuc, and expression was not inhibited by the fiber knob.

These experiments clearly showed that incorporation of the RGD peptide into the fiber of Ad5lucRGD resulted in dramatic changes in virus-to-cell interaction by providing an alternative CAR-independent cell attachment pathway. Of note, the insertion of the RGD sequence in the HI loop did not abrogate the CAR-mediated entry pathway, so the modified vector has a two independent mechanism to bind to the cells.

As the present invention shows, this contributes to the enhanced infectivity of the modified vector in all cell lines and tumors tested.

Example 3

Enhanced Tumor Transduction Via RDG-Fiber Modification

To determine if the RGD sequence incorporated into the HI loop of the fiber could increase the infectivity of tumors, the ability of the modified vector to deliver genes to cultured human ovarian cancer cells was examined. Characterization of two cell lines, SKOV3.ip1 and OV-4, by flow cytometry showed that they both express moderate-to-high levels of $\alpha v \beta 3$ and $\alpha v \beta 5$ integrins. SKOV3.ip1 also expresses a high level of CAR, whereas OV-4 only modestly expresses CAR.

Figure 4A:
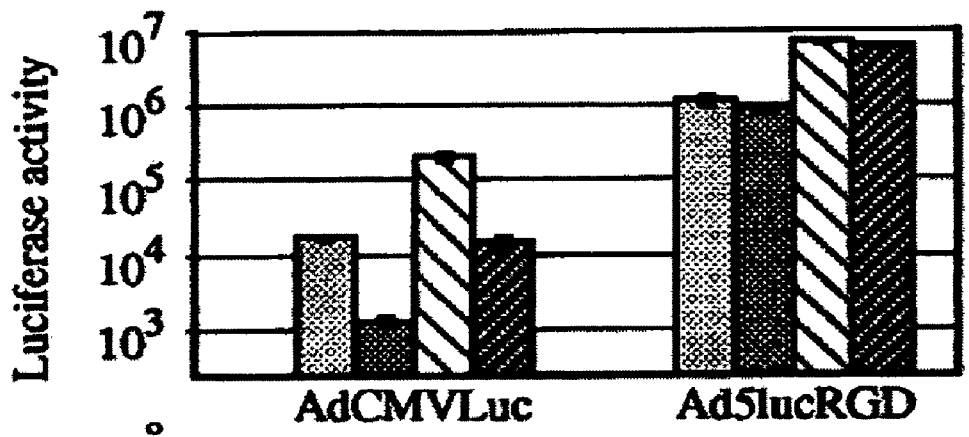
FIG. 4 shows a comparison of the gene transfer efficiencies to cultured ovarian cancer cells mediated by AdCMVLuc and Ad5lucRGD. Human ovarian cancer cells SKOV3.ipl (FIG. 4A) and OV-4 (FIG. 4B) were transduced with AdCMVLuc or Ad5lucRGD at an MOI of 1 or 10 pfu/cell essentially as described in for 293, HUVEC and RD cells. Recombinant Ad5 fiber knob protein was added to cells prior to infection with the virus. Each data point is the average of three independent measurements obtained in one experiment.
Figure 4B:
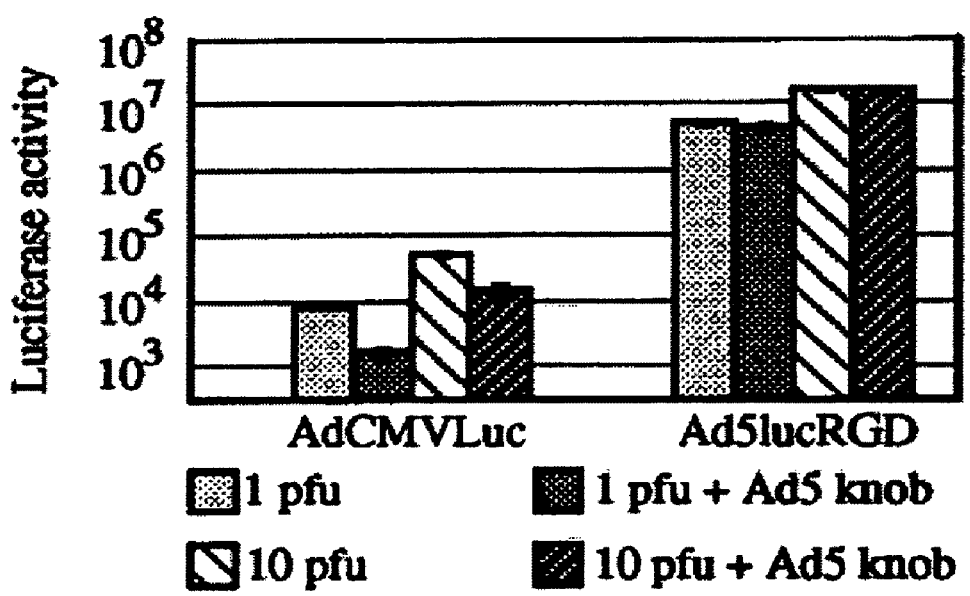

The incorporation of recombinant RGD-containing fiber protein in the Ad5lucRGD vector dramatically improved the ability of the virus to efficiently transduce these cells (FIG. 4A). At different MOIs tested, Ad5lucRGD-transduced cultures of SKOV3.ip1 cells showed 30-fold to 60-fold increase in luciferase activity compared to cells transduced with control virus. Interestingly, while the purified fiber knob blocked over 90% of AdCMVLuc-mediated gene transfer, it could only block 20% of luciferase activity in Ad5lucRGD-treated cells, indicating a significant CAR-independent entry mechanisms for Ad5lucRGD. In OV-4 cells, the transduction efficiency achieved with the RGD-modified vector was 300- to 600-fold higher than the unmodified one (FIG. 4B). Again, when the fiber knob was used as an inhibitor of CAR-mediated cell entry, it did not have any significant effect on Ad5lucRGD-mediated gene delivery, strongly suggesting that this virus primarily utilizes RGD-integrin interaction to bind to target cells.

The utility of the Ad5lucRGD vector was next evaluated in the context of primary tumor cells. In this regard, recent human clinical trials have pointed out the disparity between the efficacy of adenoviral vectors in various model systems and in the clinical context, where rather low transduction efficiencies have been noted. As integrins have been shown to be frequently overexpressed by various epithelial tumors, vector targeting to these cell surface receptors provides a means to achieve CAR-independent gene transfer.

Figure 5A:
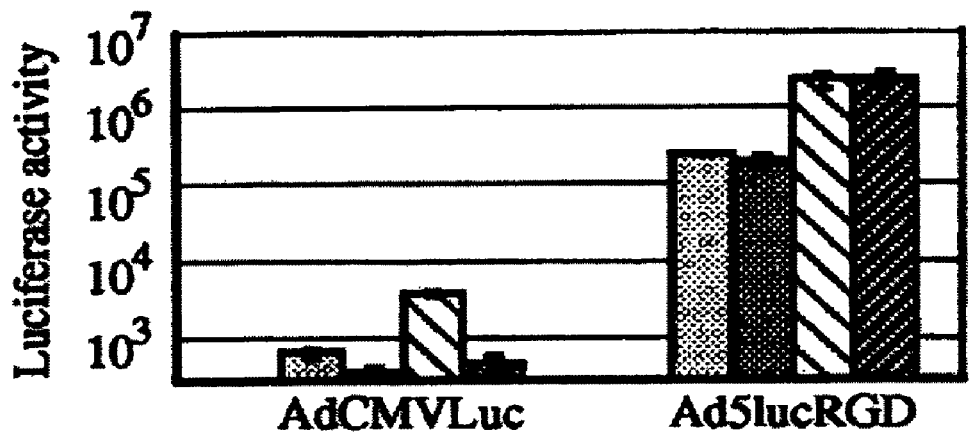
FIG. 5 shows transduction of primary cells isolated from ascites obtained from ovarian cancer patients. Cells isolated from ascites of two (FIGS. 5A and B) ovarian cancer patients were transduced with AdCMVLuc or Ad5lucRGD at MOI of 1 or 10 in the presence or absence of blocking Ad5 fiber knob protein. The data points represent the mean of three independent determinations.
Figure 5B:
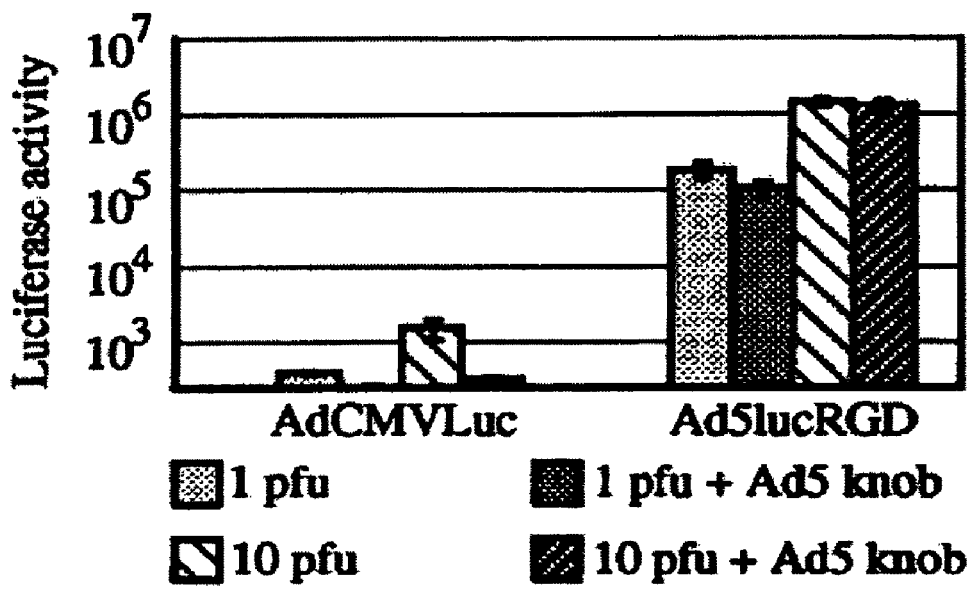

Ovarian cancer cells obtained from two patients were treated with either Ad5lucRGD or AdCMVLuc in the presence or absence of blocking knob protein. Luciferase expression in cells treated with AdCMVLuc was extremely low (FIG. 5), thereby indicating inability of adenoviral vectors containing unmodified fibers to efficiently infect ovarian cancer cells. Strong inhibition by the fiber knob on AdCMVLuc-mediated luciferase expression suggests that the fiber-CAR interaction is the only pathway this virus can use to infect this type of cell. In contrast, Ad5lucRGD directed levels of transgene expression two- to three-orders of magnitude higher than those detected in AdCMVLuc-transduced cells. The knob protein blocked 20% of the gene transfer at an MOI of 1 pfu/cell, and no effect was observed at an MOI of 10 pfu/cell.

The observations of enhanced infectivity have been extended to other tumor cell types besides ovarian carcinoma. In six human non-small cell lung adenocarcinoma cell lines, one 25 human mesothelioma cell line, and one rat mesothelioma cell line, the luciferase expression level achieved with the RGD-modified vectors was always higher than the level achieved with the non-modified vector at a variety of different MOIs.

Figure 6A:
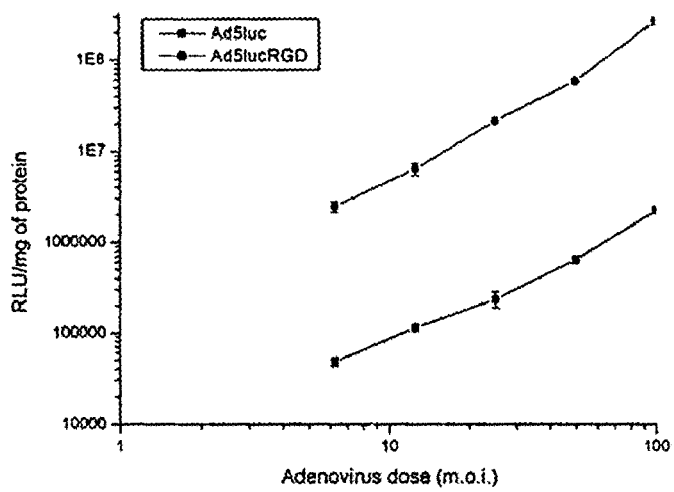
FIG. 6 shows enhancement of adenovirus infectivity by RGD modification of the fiber knob. Triplicates of A549 cells (panel A) and LNCaP cells (panel B) were transduced with increasing doses of either Ad5luc or Ad5lucRGD. After 36 h, cell transduction was determined by luciferase assay. The data are presented as relative light units (RLU) normalized to mg of cellular protein. The results show an infectivity advantage of the RGD modified vector over the non-modified one in both cell lines.
Figure 6B:
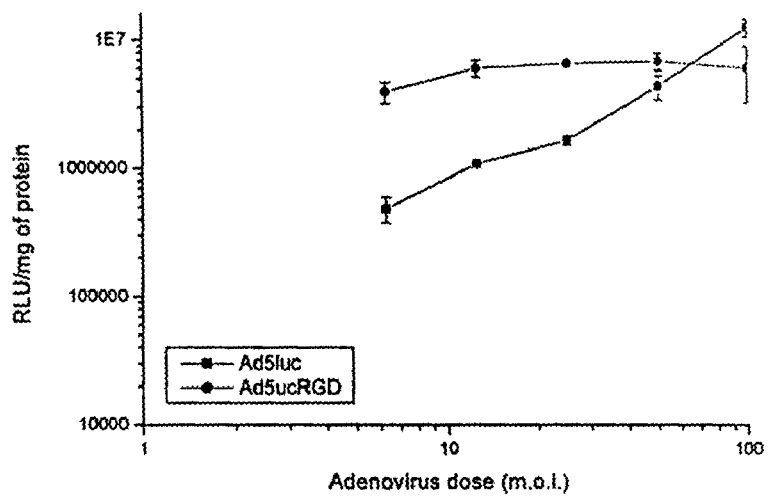

The increase in transduction was also observed in A549 lung adenocarcinoma cells and LNCaP prostate carcinoma cells (FIG. 6). In both cell lines the RGD modified vector showed an infectivity advantage over the non-modified counterpart. The major difference was observed in A549 cells, showing a 100-fold increase in infection, whereas LNCaP cells showed 10-fold increase. In LNCaP, the major differences were observed at lower multiplicities of infection, likely indicating that the integrin-mediated pathway was saturated.

The increased efficacy of infection of the RGD-modified vector was also measured in time course experiments in which the incubation time of the virus with the cells was limited. The transduction efficiency was always better with the modified vector and the differences were more marked at shorter times of infection, i.e. the RGD-modified vector produced a 1000-fold greater luciferase expression when only 7 minutes of adsorption were allowed. At longer adsorption times, the differences between the modified and non-modified vectors were reduced to 10-fold. This difference could have important implications in adenoviral-mediated gene therapy because the time of exposure of the vector to the tumor target cells is expected to be limited by the intratumoral high pressure.

Overall, this data points out the importance of providing an alternative entry pathway to adenoviral vectors for the infectivity of tumors. In all cell lines and tumor types analyzed, a vector that can use the natural entry pathway via primary binding to CAR and an additional entry pathway via binding to integrins transduces more efficiently than a vector that only can use the natural CAR receptor.

Example 4

Replication-Competent, E1-Transcomplementation Vectors

Most replication-defective adenovirus vectors in preclinical and clinical use have deleted E1A and E1B genes. These deletions render the vector unable to replicate, or replication-incompetent, and these vectors can replicate only when E1 proteins are supplied in trans. These replication-incompetent vectors transduce the cells that they infect but they do not produce any progeny.

Figure 7:
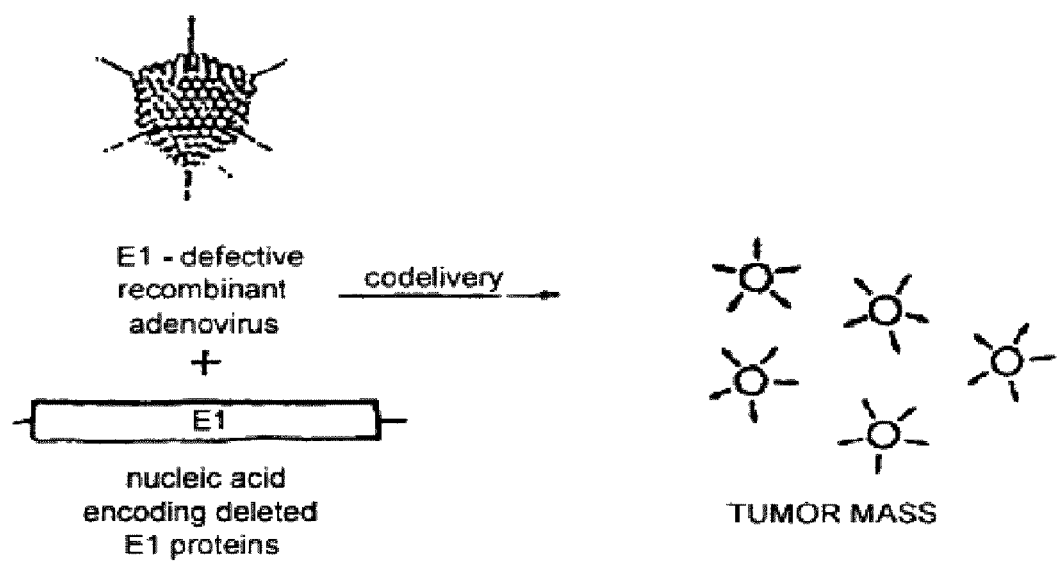
FIG. 7 shows a conceptual representation of the conditional replication enablement system for adenovirus. The initial introduction of recombinant virus into the tumor mass infects the cells shown as circles. The replication enabling plasmid converts these cells in vector-producing cells. The produced vector can infect adjacent cells (arrows).

A conditional replication enablement system for adenovirus has been developed in which the E1 genes are supplied in trans to cells infected with E1-deleted vectors (FIG. 7). The replication-enabling system has been developed primarily as a means of amplifying transduction in tumor nodules. In order to achieve a more extensive amplification of the vector and lysis of tumor cells, the secondarily produced vector should propagate continuously in tumor cells. Replication-enabling has been achieved by linking plasmids encoding the E1 proteins to the exterior of the capsid or separately introducing the plasmid using cationic lipids. These experiments provided evidence that replication-enabling systems could achieve amplification of the in vivo therapeutic response of an adenoviral vector carrying HSV-TK. E4-deleted adenoviruses have also been transcomplemented with a plasmid containing the E4 open reading frame 6 gene or the complete E4 region. E4 transcomplementation is important in the context of reducing immunogenicity and increasing long-term gene transfer.

Figure 8:
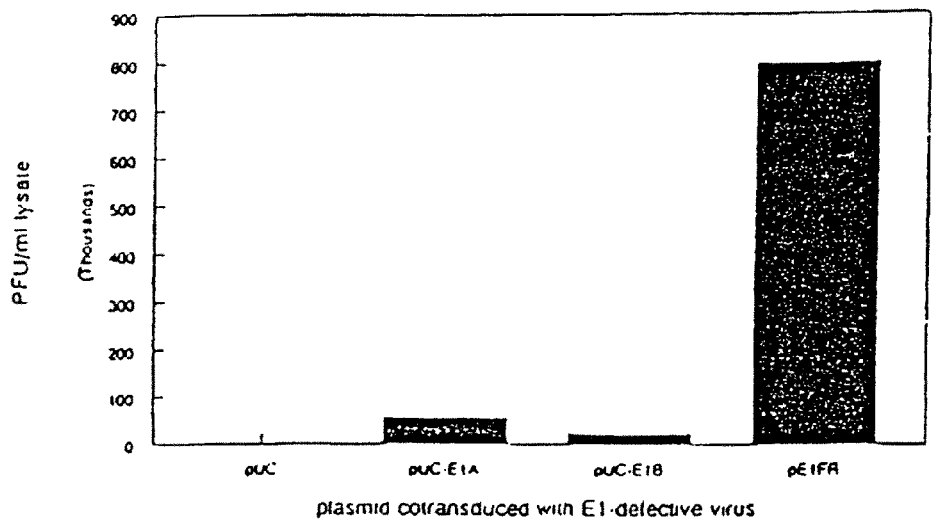
FIG. 8 shows functional analysis of pE1FR. LS174T cells were cotransduced with the plasmid indicated in the abscissa as a liposomic complex (0.5 µg DNA/1.0 µg DOTAP:DOPE) and AdCMVluc (MOI=1). Forty eight hours after transduction, the amount of virus present in the lysate of cells was measured by a plaque assay in 293 cells.
Figure 9:
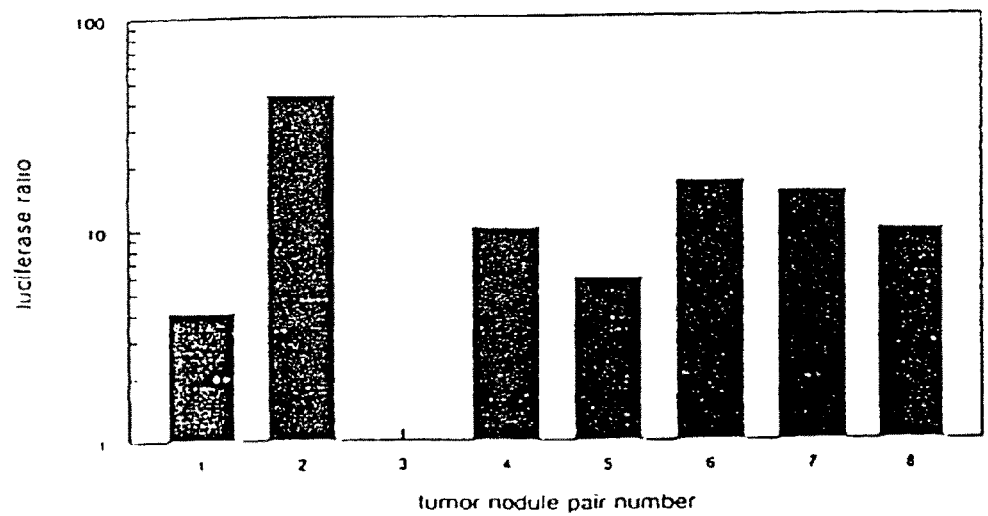
FIG. 9 shows enhancement of E1-defective adenoviral transgene expression by pE1FR administration. Nude mice engrafted with human lung adenocarcinoma tumors (A549 cell line) received an intratumoral injection of E1-defective virus AdCMVluc ($10^8$ pfu per 8-10 mm diameter tumor) mixed with plasmid pE1FR or pUC13 (3 µg). One week later, luciferase expression in tumors was measured. Each bar represents one mouse with a pair of tumors, one treated with AdCMVluc and pE1FR and the other one with AdCMVluc and pUC13. The ratio of luciferase expression in the tumor treated with pEIFR versus the one treated with pUCI3 is shown.

In order to further enhance the utility of the replication-enabling system, it is a goal of the present invention to reduce the possibilities of recombination between the E1-deleted vector and the transcomplementing plasmid. This recombination would generate replication competent adenoviruses (RCA). Therefore, an E1 expressing plasmid has been constructed, pE1FR, in which E1a and E1b sequences are in tandem but oriented in opposite 5' to 3' direction. Cells co-transduced with this plasmid and an E1-defective adenoviral vector using cationic liposomes resulted in replication-defective adenovirus production levels comparable to that achieved by co-transduction of the virus and pE1 (FIG. 8). Comparable results were obtained with HeLa, A549 and SKOV3-ip1 cell lines.

This demonstrates that pE1FR can transcomplement E1-deleted vectors and convert the infected cells into vector-producing cells. To demonstrate that this vector could also enhance the tumor transduction achieved with an E1-deleted vector in vivo, tumors were injected with E1-defective virus mixed with pE1FR, or a plasmid control. Assessment of the luciferase content showed that 6 out of 8 tumors had increased luciferase activity in the pE1FR group relative to the controls (FIG. 8).

This data indicates that E1-expression vectors, such as pE1FR, represent a feasible way to increase the in vivo transduction efficiency of E1-deleted vectors in tumors. The amplification of the transduction efficiency achieved with a system such as the replication enabling system is limited, however, by the inability of the vector progeny to keep replicating. The replication-enabling function needs to be carried over in the vectors produced by the tumor cells to allow repeated cycles of replication.

Example 5

Replication Competent Vectors Dependent Upon IL-6

As shown in the data above, the replication-enabling system has been developed primarily as a means of amplifying transduction in tumor nodules. Methods have also been explored to achieve a more extensive amplification of the vector and subsequent lysis of tumor cells. To fulfill this goal, the secondarily produced vector should propagate continuously in tumor cells and incorporate a regulatory mechanism that confines this propagation to the tumor. E1a 12s and 13s adenoviral proteins are necessary to induce the expression of other viral genes, and therefore, an E1a-deleted vector is impaired in its replication. It has been reported that interleukin 6 can induce transcription factors that are able to substitute for the E1a activity of adenovirus.

Figure 10:
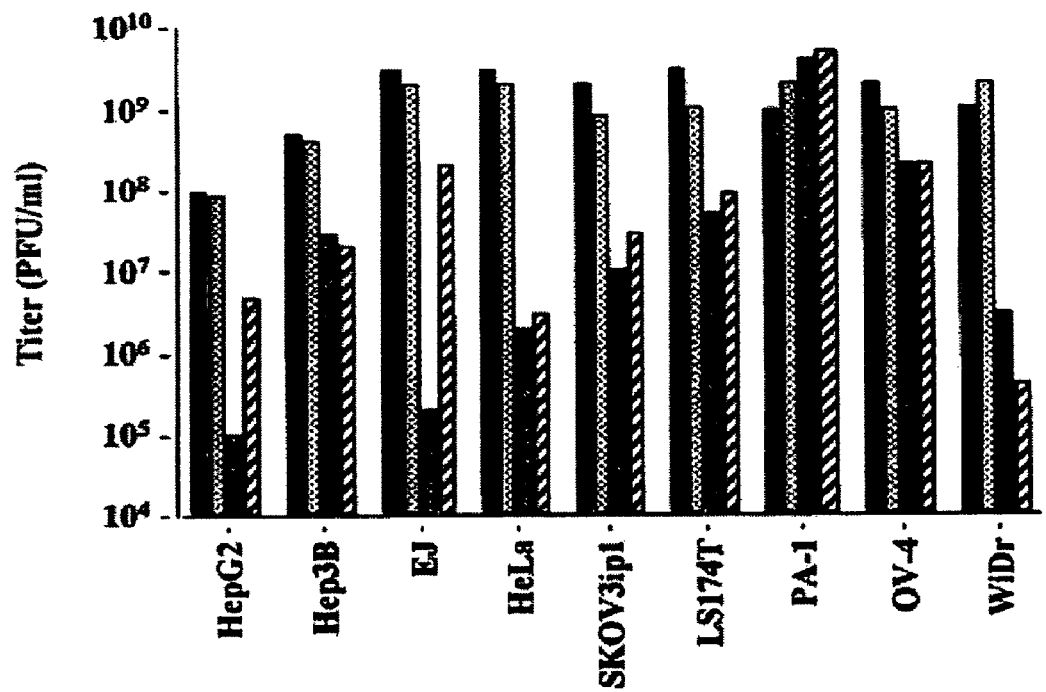
FIG. 10 shows the E1A-like activity of IL-6 can be exploited to produce Ad312 virions in HepG2 cells and in a variety of cell lines responsible to IL-6. Cells (1 to $4\times10^5$) were infected with wild type adenovirus or Ad5dl312 at an MOI of 10 in the absence or presence of 100 units/ml of rhIL-6. Six days later, cells were lysed and the amount of virus in the lysates was quantitated by plaque assay in 293 cells. For each cell line, bar from left to right represent wild type, wild type+IL-6, dl312, and dl312+IL-6.

To explore whether an E1a-deleted vector such as Ad5dl312 could replicate in the presence of IL-6 in different cancer cell lines, cells were infected with dl312 in the presence of IL-6 and the progeny were examined (FIG. 10). In all cell lines, infectious virions were produced to a certain extent in the presence and absence of IL-6, although in lower amounts than the wild type adenovirus. The effects of IL-6 in dl312 production were markedly seen in two cell lines: HepG2 and EJ. In HepG2 cells, IL-6 resulted in a 1.5 log increase of viral production.

Figure 11:
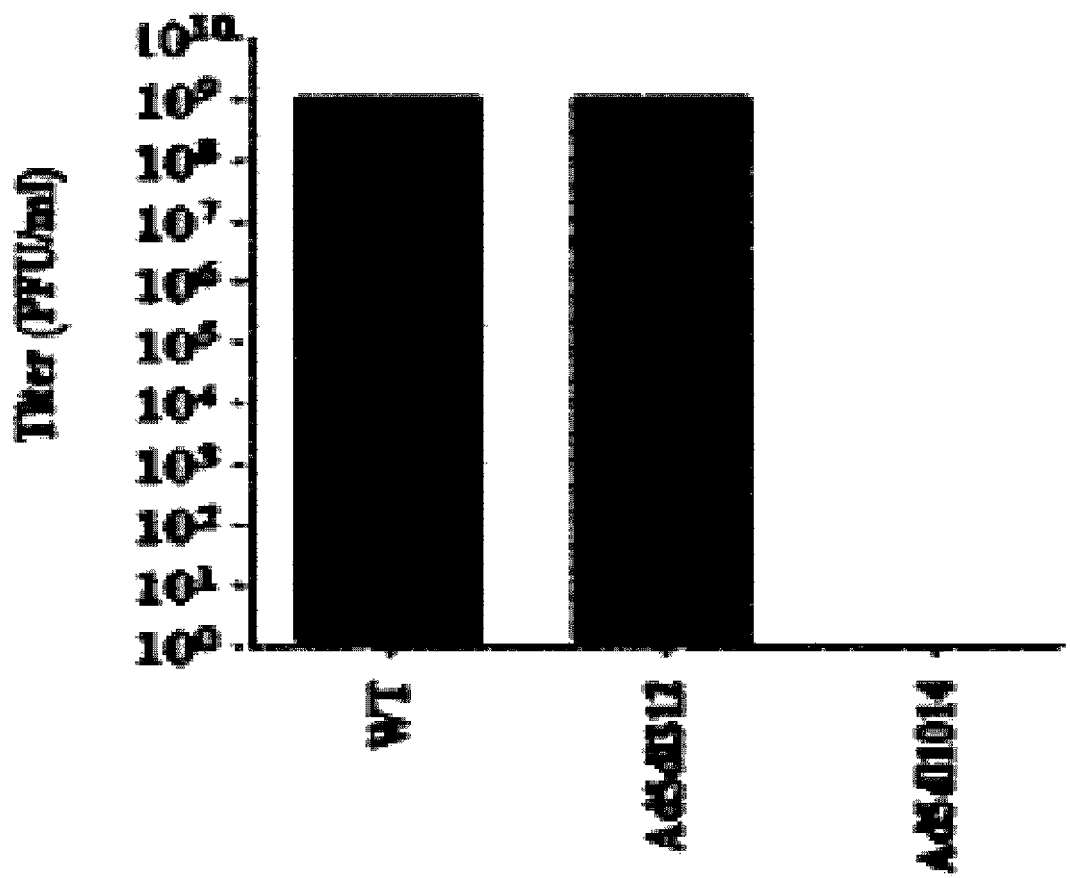
FIG. 11 shows replication of Ad5dl312 and oncolytic effect in tumor cells without IL-6 addition. Ovarian carcinoma cells (OVCAR-3) were infected with E1-a deleted AD5dl312, wild type or E4-deleted AdSdl1014 (MOI=10).

These experiments demonstrate that the IL-6-inducible E1a-like activity can complement the E1a deletion during infection of HepG2 and EJ cells. To overcome the requirement of exogenous IL-6, carcinomas, e.g., cervical, chorio, and ovarian, that have an IL-6 autocrine loop were infected with the E1A-deleted virus, dl312. OVCAR-3 and SW626 cells have a functional IL-6 autocrine loop. Upon infection of OVCAR-3 cells with Ad5dl312, or wild type or E4-deleted control viruses, Ad5dl312 was produced to levels similar to levels produced by the wild type control, even in the absence of IL-6 (FIG. 11). This IL-6 independent replication of E1a-deleted virus was also demonstrated in SW626 cells and primary cultures of ovarian tumors (FIG. 11).

These results indicate that cells with an autocrine loop of IL-6 can selectively support the replication of Ad5dl312 without the addition of exogenous IL-6, and that these cells are lysed by the E1a-deleted virus. The effects of the E1a-deleted virus in normal cells were examined. To test the ability of this virus to propagate in normal cells adjacent to ovarian tumors, human mesothelial cells isolated from peritoneal lining tissue were infected. Contrary to the wildtype virus control, Ad5dl312 did not replicate in these cells even in the presence of IL-6.

Overall, this data indicates that E1a-deleted adenovirus can be complemented by the IL-6-induced E1a-like activity found in several tumors. E1a-deleted vectors are, however, limited by the fact that E1a intrinsic activity has been noted in normal cells. IL-6 production, in the other hand, could result from the injection of the vector in an immunocompetent host and this natural inflammatory response would result in non-specific complementation. Clearly, new mechanisms of tumor-specificity need to be incorporated to control the replication of adenoviral vectors.

The clinical benefits of cancer gene therapy achieved with non-replicative adenoviral vectors have been hampered by the significant number of cells in a tumor which have been left unaffected by the direct or indirect effects of the transgenes. Conditional replicative adenoviruses may represent a significant improvement to solve this problem, but efficient infectivity and tumor-selective replication need to be achieved to realize their full potential.

The importance of the modification of the adenoviral capsid to increase the binding of the vector to the tumor cells has been demonstrated herein. An integrin-binding RGD motif inserted in the HI loop of the adenoviral fiber confers an additional binding pathway besides the natural coxsackie-adenovirus receptor, and this dramatically increases the infectivity of the vector. The data herein also indicates that transduction efficiency can also be enhanced if the vector is able to replicate in the tumor. A transcomplementation system has been developed as a means to evaluate the effects of replication on the transduction efficiency. This replication-enabling system also provides the opportunity to analyze the efficacy and specificity of different tumor-specific replication mechanisms before incorporating these mechanisms into a single viral vector in a cis-complementation strategy that will allow continuous replication. In this regard, continuous tumor-selective replication has been shown using E1a-deletion mutants that propagate in tumors due to an E1a-like activity.

Example 6

Incorporation of RGD-Fiber into Currently Defined Conditional Replicative Mutant Viruses As an initial approach towards comparing the therapeutic potential of an RGD-modified versus an unmodified replicative adenovirus, conditional replicative mutants that have been previously described were chosen. Deletion of the E1b-55K protein was designed to confer selective replication to adenoviruses in cells lacking functional p53. In a similar way, deletion of the Rb-binding sites of E1a has been proposed to achieve selective replication in cells lacking Rb. These deletion mutants are used as established models of selective replication-competent viruses.

The initial plasmid to construct these deletions is pXC1, which contains adenoviral sequences from basepair 22 to 5790 (Microbix, Hamilton, Canada). For the E1b55K deletion, the region from Sau3AI (Ad5#2426) to BglII (Ad5#3328) is removed by ligation of the 1 kb XbaI-Sau3AI DNA fragment with the 7.9 kb XbaI-BglII DNA fragment to yield plasmid pXC-55K–. For an E1a deletion construct that abrogates binding to Rb, a derivative of pXC1 (pXC1 D24) is obtained with E1a deleted in residues 122 to 129 (Dr. Juan Fueyo, MDACC). This deletion affects the residues of the conserved region 1 of E1a necessary to bind Rb. These E1b and E1a deletions are incorporated into the viral genome by homologous recombination with plasmid pVK503, containing either an unmodified fiber or an RGD modified fiber. From the plasmids obtained by homologous recombination, the unmodified 55k– and D24 mutants are generated by releasing the viral genome with PacI and transfecting into 293 cells. Viruses are amplified and purified by double CsCl gradient, and titered in 293 cells for in vitro and in vivo experiments. The presence of mutated E1, altered fiber, and contaminating wild type E1, is analyzed by PCR as well as by sequencing of viral DNA isolated from CsCl-purified virions.

Figure 12A:
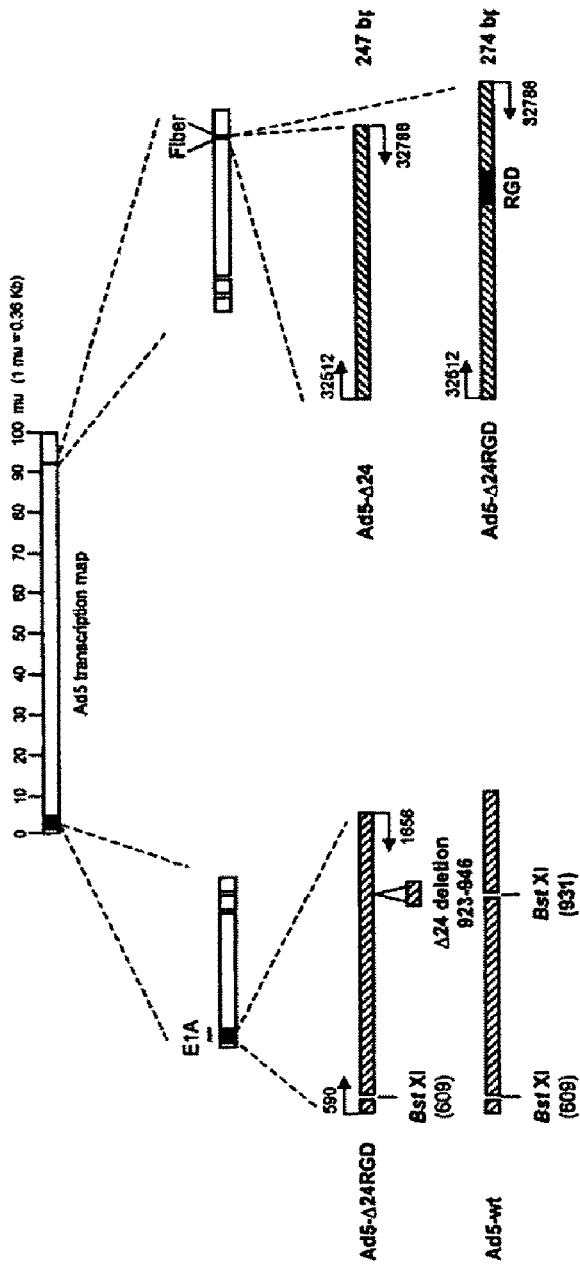
FIG. 12A shows the map of E1A and fiber encoding regions of Ad5-D24RGD amplified by PCR, showing the 24-bp deletion and the introduced RGD encoding sequence.
Figure 12B:
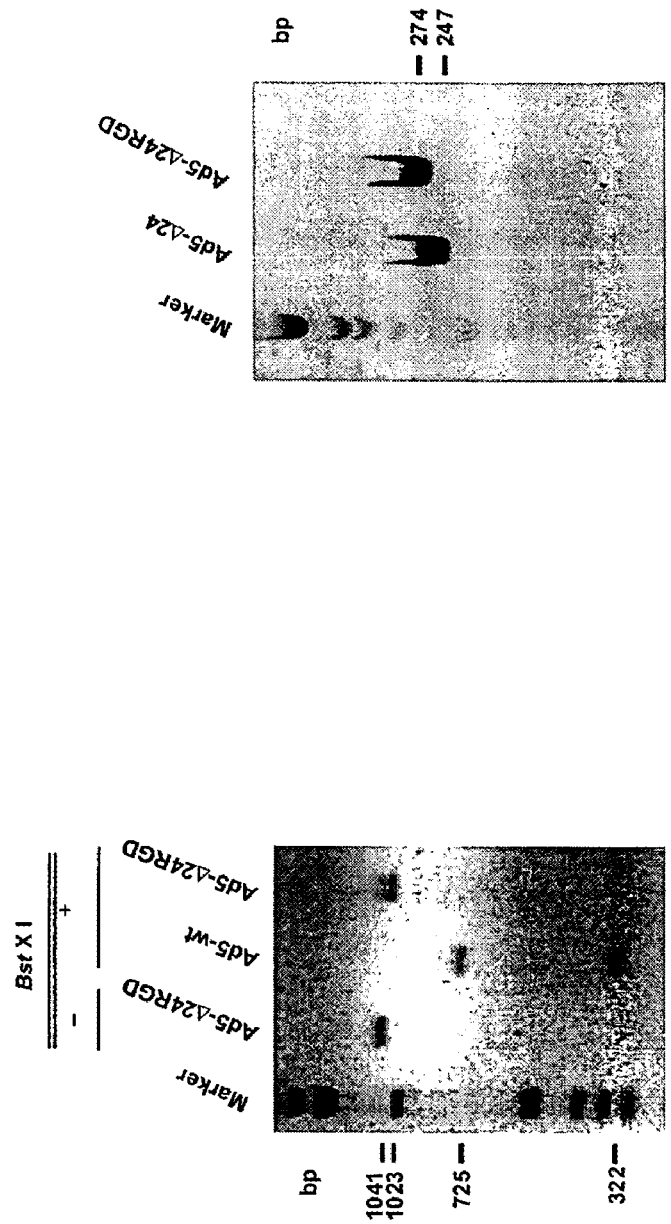
FIG. 12B shows restriction analysis of Ad5-D24RGD. The presence of the 24-bp deletion was confirmed by BstX I digestion of the PCR product of the E1A region. The fragments were resolved on a 2% agarose gel, and visualized by UV fluorescence. Marker: Gibco 1 Kb DNA ladder. The presence of uncleaved PCR product verified the presence of the deletion (left). PCR amplification products of the region encoding the fiber from Ad5-D24 and Ad5-D24RGD were resolved on a 6% acrylamide gel. Marker: Gibco 100 bp DNA ladder. The bigger size (27 bp) of Ad5-D24RGD band indicates the presence of the sequence encoding RGD (right).

The 24-bp deletion in the E1A gene and the RGD encoding sequence in the fiber were verified by PCR (FIG. 12). The presence of the RGD motif in the modified fiber was confirmed by PCR employing fiber primers FiberUp (5'-CAAACGCTGTTGGATTTATG-3') (SEQ ID NO:2) and FiberDown (5'-GTGTAAGAGGATGTGGCAAAT-3') (SEQ ID NO:3). The 24-bp deletion was analyzed by PCR with primers E1a-1 (5'ATTACCGAAGAAATGGCCGC-3') (SEQ ID NO:4) and E1a-2 (5'CCATTTAACACGCCATGCA-3') (SEQ ID NO:5) followed by BstXI digestion. Of note, no adenoviruses having wild-type E1 or wild-type fiber appeared throughout the propagation of Ad5-D24RGD, a finding that confirms the lack of endogenous adenoviral sequences in A549 cells.

Example 7

Evaluation of Infectivity of RGD-Modified Conditional Replicative Viruses

Procedures described above are used to demonstrate that the RGD-modified 55K– and D24 virions bind to integrins. ELISAs are performed with immobilized virions incubated with purified αvβ3 integrins and anti-α subunit monoclonal antibody, VNR139. The modified replicative viruses are examined to determine if they are able to bind cells via a CAR-independent pathway. 293, HUVEC, and RD cells are used, as enhanced RGD-mediated transduction of these cell lines has already been demonstrated. For binding analysis, virions are labeled with $^{125}$I and incubated with cells. Recombinant knob protein is used as an inhibitor to measure CAR-independent binding. Infectivity of modified and unmodified 55K and D24 mutants in ovarian, lung and other tumor cell lines, as well as in primary tumors, are compared. These experiments indicate that the RGD-modified viruses infect tumor cells more efficiently than the non-modified vectors.

Example 8

Evaluation of Oncolytic Potential of RGD-Modified Conditional Replicative Viruses This example demonstrates that the genetic introduction of an RGD sequence in the fiber of a CRAd allows CAR-independent infection that leads to the enhancement of viral propagation and oncolytic effect in vitro and in vivo.

Cell Lines

A549 human lung adenocarcinoma and LNCaP human prostate cancer cell lines were obtained from the American Type Culture Collection (Manassas, Va.). The cells were cultured in Dulbecco's modified Eagle's medium (DMEM) supplemented with 5% heat-inactivated fetal bovine serum (PBS), 100 I.U./ml penicillin, and 100 mg/ml streptomycin.

Virus DNA Replication

A549 cells cultured at 90% confluence in 6-well plates were infected with Ad5-D24 or Ad5-D24RGD at a dose of 0.01 viral particles/cell. After 2 h, the cells were washed and maintained in DMEM-5% FBS with 1 mCi/ml bromodeoxyuridine (BrdU) (Amersham Pharmacia Biotech Inc., Piscataway, N.J.). Attached and detached cells were harvested at 2, 4, 6, and 8 days after infection, and encapsidated viral DNA was purified by the spermine-HCl method (Hardy et al., 1997). One third of the total purified viral DNA (corresponding to $6 \times 10^5$ cells) was digested with HindIII and resolved in 1% agarose gel. The fragments were transferred to a nylon membrane (Amersham Pharmacia Biotech), fixed, blocked in blocking buffer (50 mM Tris-HCl, pH 7.5, 150 mM NaCl, 5% dry milk, 2% Tween 20), and incubated with mouse anti-BrdU IgG (DAKO, Carpinteria, Calif.) at 4° C. overnight. The membrane was washed next day, incubated with peroxidase-labeled anti-mouse antibody (Amersham), and processed by Western blotting analysis with the ECL system (Amersham). The membrane was exposed to Kodak Biomax ML film for 3 seconds at room temperature and developed in an automated processor.

Adenovirus Yield Assay

A549 cells cultured at 90% confluence in 6-well plates were infected with 0.01 particles/cell of Ad5lucRGD, Ad5-D24, or Ad5-D24RGD for 2 h. The cells were then washed thoroughly with PBS to remove all non-adsorbed viruses, and maintained in DMEM 5% FBS. After 8 days, cells and media were harvested, freeze-thawed 3 times, centrifuged, and the titer was determined by plaque assay with A549 cells as targets.

Oncolysis Assay

A549 and LNCaP cells cultured in triplicate in 6-well plates were infected with one of the three types of adenovirus at doses of 0.001 or 0.01 viral particles/cell when 90% confluence was reached. Eight or ten days after infection, the cell monolayers were washed with PBS, fixed with 10% fresh buffered formaldehyde for 10 min, and stained with crystal violet solution (1% crystal violet [w/v], 70% ethanol). After 1 h staining, the plates were rinsed with tap water and dried.

In Vitro Cytotoxicity Assay (XTT)

A549 and LNCaP cells were seeded and infected in parallel with the ones used for the oncolysis assay described above. Eight or ten days after infection, the media was carefully removed, and fresh media containing 200 μg/ml of 2,3-bis[2-methoxy-4-nitro-5-sulfophenyl]2H-tetrazolium-5-carboxyanilide (XTT) (Sigma, St. Louis, Mo.) was added. Cells were then incubated for 3 h at 37° C. The content of each well was transferred to a microwell plate, and the light absorbance was read at 450 nm in a microplate reader (Molecular Devices Corp., Sunnyvale, Calif.). The number of living cells was calculated from non infected cells cultured and treated with XTT in the same way as were the experimental groups.

Subcutaneous Tumor Xenograft Model in Nude Mice

Female athymic nu/nu mice (Frederick Cancer Research, MD) 8-10 weeks old were used to grow A549 s.c. nodules. Eight million cells were xenografted under the skin of each flank in anesthetized mice. When the nodules reached 60-100 mm³ a single dose of $10^9$ viral particles (high-dose experiment, n=5) or $10^7$ viral particles (low-dose experiment, n=4) of Ad5lucRGD, Ad5-D24, Ad5-D24RGD, Ad5-wt or PBS was administered intratumorally (i.t.). Tumor size was monitored twice a week, and fractional volume was calculated from the formula: (length×width×depth)×½. The mice were euthanized 35 days after the treatment because of the size of the tumors in the control group. Statistical differences among groups were assessed with student's t tests.

Adenovirus Hexon Immunodetection

The presence of adenovirus hexon in the treated tumor xenografts was assessed by immunofluorescence at the end of the experiment. Frozen A549 nodule specimens were sections, fixed in 3% formaldehyde, and blocked with normal donkey serum for 30 min at room temperature. Then goat anti-hexon antibody (Chemicon Inc., Temecula, Calif.) was applied for 2 h at room temperature, followed by PBS rinse and incubation with Alexa Fluor 488-labeled donkey anti-goat antibody (Molecular Probes, Eugene, Oreg.) for 30 min at room temperature. The slides were then rinsed and counterstained with Hoechst 33342 (Molecular Probe) for 10 min, and analyzed under a fluorescent microscope (Leitz Orthoplan).

Figure 13:
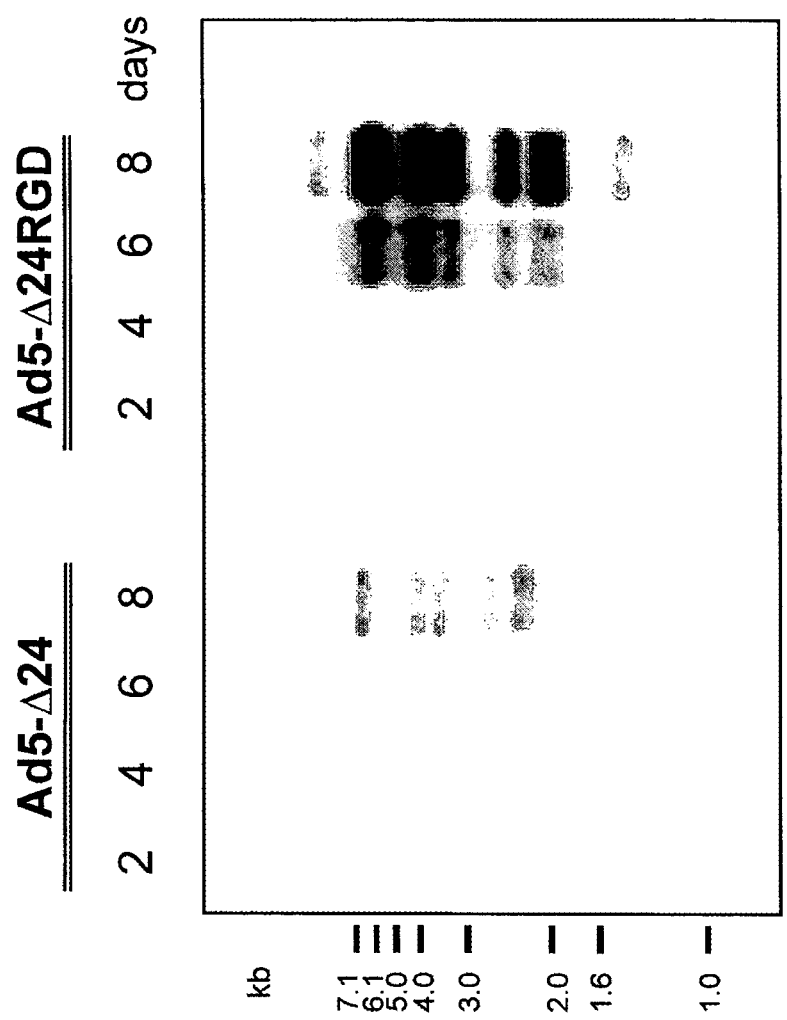
FIG. 13 shows propagation efficiency of Ad5-D24 versus Ad5-D24RGD. A549 cells were infected with 0.01 particles/cell of Ad5-D24 or Ad5-D24RGD and incubated in medium containing 1 mCi/ml of BrdU. At the indicated times after infection, the cells were harvested, and the encapsidated DNA was purified by the spermine-Hcl method. Viral DNA from $6\times10^5$ infected cells was digested with HindIII, electrophoresed, and the resulting fragments were blotted into a membrane that was processed with a mouse anti-BrdU antibody. The amount of BrdU incorporated into viral DNA indicated that Ad5-D24RGD propagation is more efficient than that of Ad5-D24.

After structural confirmation, the replication capacity of Ad5-D24RGD and Ad5D24 were compared in A549 cells. Cell monolayers were infected with low dose of each virus (0.01 viral particles/cell), and were maintained in media with BrdU throughout the 8-day incubation period. The encapsidated viral DNA was purified on days 2, 4, 6, and 8 postinfection. Viral DNA corresponding to $6 \times 10^5$ cells was analyzed by Southwestern blot using anti-BrdU antibody. As indicated by the BrdU incorporated into replicating viral DNA, Ad5-D24RGD propagation was more efficient than that of Ad5-D24 (FIG. 13). The Ad5D24RGD DNA can be detected not only sooner (day 6) compared to Ad5-D24 DNA (day 8), but in greater amounts. Thus, the infectivity advantage conferred by RGD incorporation into the fiber knob increased adenovirus propagation in target cells. As this tropism modification would not be anticipated to alter fundamental aspects of the viral replication cycle, this effect was likely achieved exclusively on the basis of the infectivity enhancement allowed by routing the virus through CAR-independent pathways.

Based on the previous experiment, the actual amount of infectious virus produced by Ad5lucRGD, Ad5-D24, or Ad5-D24RGD in A549 cells at 8 days after infection were quantified by plaque assay. Ad5-D24RGD produced a viral yield of $3.75 \times 10^9$ pfu/ml, which was 43 times higher than that of its unmodified Ad5-D24 counterpart ($8.75 \times 10^7$ pfu/ml). No virus was obtained from the nonreplicative control Ad5lucRGD infected cells. These results are consistent with the fact that modifying the fiber knob with an RGD motif led to enhancement of viral infectivity and an increase in the production of infectious adenovirus.

Figure 14:
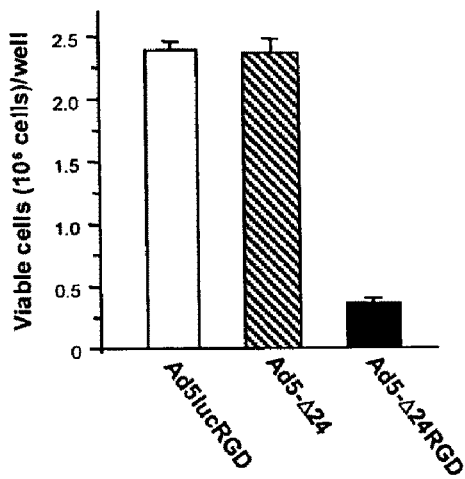
FIG. 14 shows oncolytic potency of the RGD-modified virus.
Figure 14:
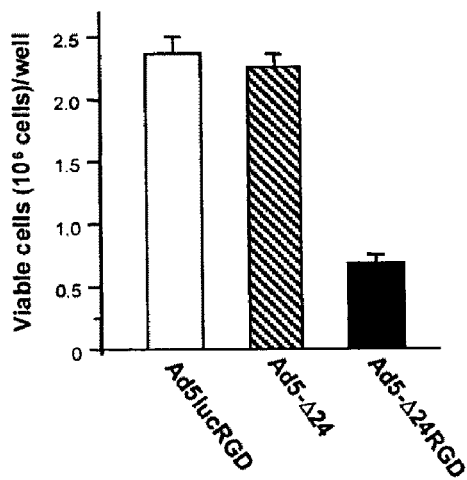

To demonstrate the increased lytic potency of Ad5-D24RGD, A549 and LNCaP cells were infected with small amounts of each virus to allow multiple cycles of viral replication over the ensuing 8 days, then stained the attached cells with crystal violet and counted viable cells by XTT assay. In both cell lines, the fewest viable cells were detected in the Ad5-D24RGD-infected group (FIG. 14). The cell lysis capacity of Ad5-D24RGD is 7 times higher in A549, and 3.5 times higher in LNCaP compared to Ad5-D24. These results demonstrate that the fiber knob modification enhanced adenoviral lytic potency over that of the Ad5-D24 virus.

Figure 15A:
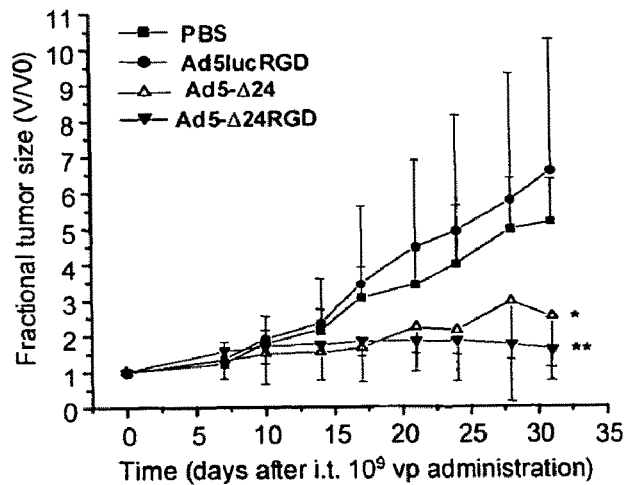
FIG. 15A shows subcutaneous A549 xenografts in nude mice treated with a single i.t. injection of $10^9$ viral particles of Ad5lucRGD, Ad5-D24, Ad5-D24RGD, or with PBS alone.
Figure 15B:
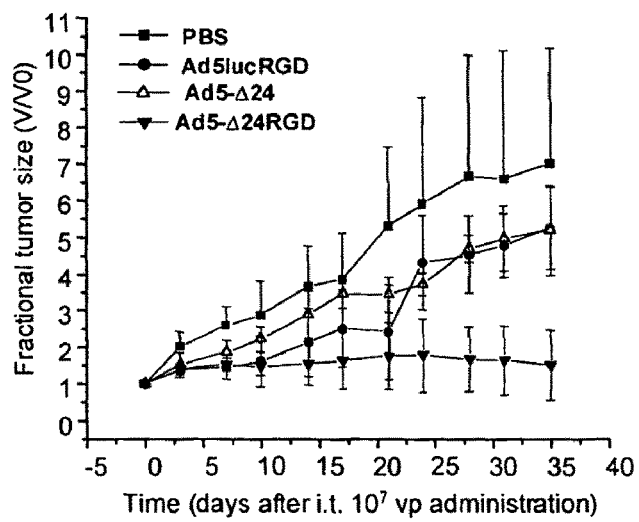
FIG. 15B shows subcutaneous A549 xenografts in nude mice treated with a single i.t. injection of $10^7$ viral particles of Ad5IucRGD, Ad5-D24, Ad5-D24RGD, or with PBS alone. Tumor size was measured twice a week. Results are shown as fractional tumor volumes (V/V0, where V=volume at each time point; V0=volume at adenovirus injection), and each line represents the mean of 5 tumors (±SD) in the high-dose group, and 4 tumors (±SD) in the low-dose group. In the high-dose experiment, both CRAds show a similar oncolytic effect that results in smaller tumors compared to PBS treated groups (*Ad5-D24 p<0.05; **Ad5-D24RGD p<0.01). However, in the low-dose experiment, tumors treated with Ad5-D24 followed a growth curve similar to that of tumors treated with non-replicative Ad5lucRGD; tumors treated with Ad5-D24RGD did not grow (p<0.01 compared to PBS).

A goal of this study was to support the oncolytic superiority of infectivity enhanced conditionally replicative adenovirus (CRAd) over that of unmodified adenoviruses in vivo. Since low doses of virus allow several cycles of replication along with destruction of tumor cells, even a single dose would produce an exponential rise in the number of killed cells, which would extend to the entire tumor. In order to demonstrate this hypothesis, A549 xenografts in nude mice were treated with a single i.t. injection ($10^9$ viral particles) of one of the three viruses or with PBS. At 32 days after injection, both CRAds demonstrated to have an oncolytic effect in the tumors opposite to those treated with nonreplicative virus or with PBS (Ad5-D24, $p<0.05$; Ad5-D24RGD, $p<0.01$ compared to PBS group) (FIG. 15A). Given these results, another experiment was performed in which a 100-fold lower dose ($10^7$ viral particles) of the viruses were administered. This low-dose treatment demonstrated that the oncolytic effect of Ad5-D24RGD was superior to that of Ad5-D24 ($p<0.05$). These differences observed between high-dose and low-dose experiments suggest that a threshold dose over $10^7$ viral particles of Ad5-D24 is required to obtain an oncolytic effect in tumor nodules (FIG. 15B).

Figure 15C:
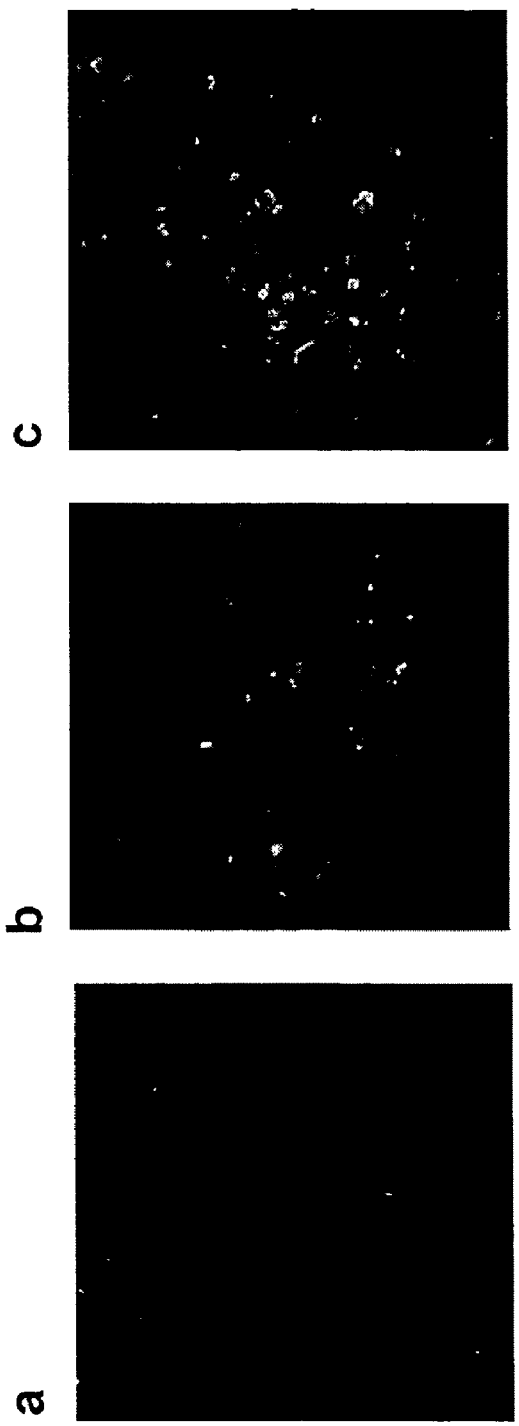
FIG. 15C shows the detection of adenovirus hexon in tumor xenografts by immunofluorescence. Frozen sections of tumor specimens injected with (a) Ad5lucRGD, (b) Ad5-D24, and (c) Ad5-D24RGD were treated with goat anti-hexon antibody and Alexa Fluor 488-labeled donkey anti-goat antibody, and nuclei were counterstained with Hoechst 33342. Images were captured from Leitz fluorescence microscope (100× magnification) with a double filter. Sections taken from tumors treated with CRAds were positive for adenovirus presence (green dots in b and c), being Ad5-D24RGD signal stronger than that of Ad5-D24. Samples taken from tumors treated with PBS (not shown) or Ad5lucRGD exhibited no hexon signal (a). i.t., intratumoral; vp, viral particles; Ad, adenovirus.

To confirm that the CRAds were present in the tumor tissue, immunofluorescence assays were used to detect the virus hexon in tumor samples collected after the low-dose experiment (35 days postinjection). Ad5-D24RGD was present in the tumor nodules, as was Ad5-D24 to a lesser extent. PBS and Ad5lucRGD treated nodules showed no hexon signal (FIG. 15C). These results corroborate that the partial reduction of tumor mass was due to virus replication and that the RGD modification of the fiber knob conferred infectivity and oncolysis advantage to a CRAd in vivo.

Figure 16:
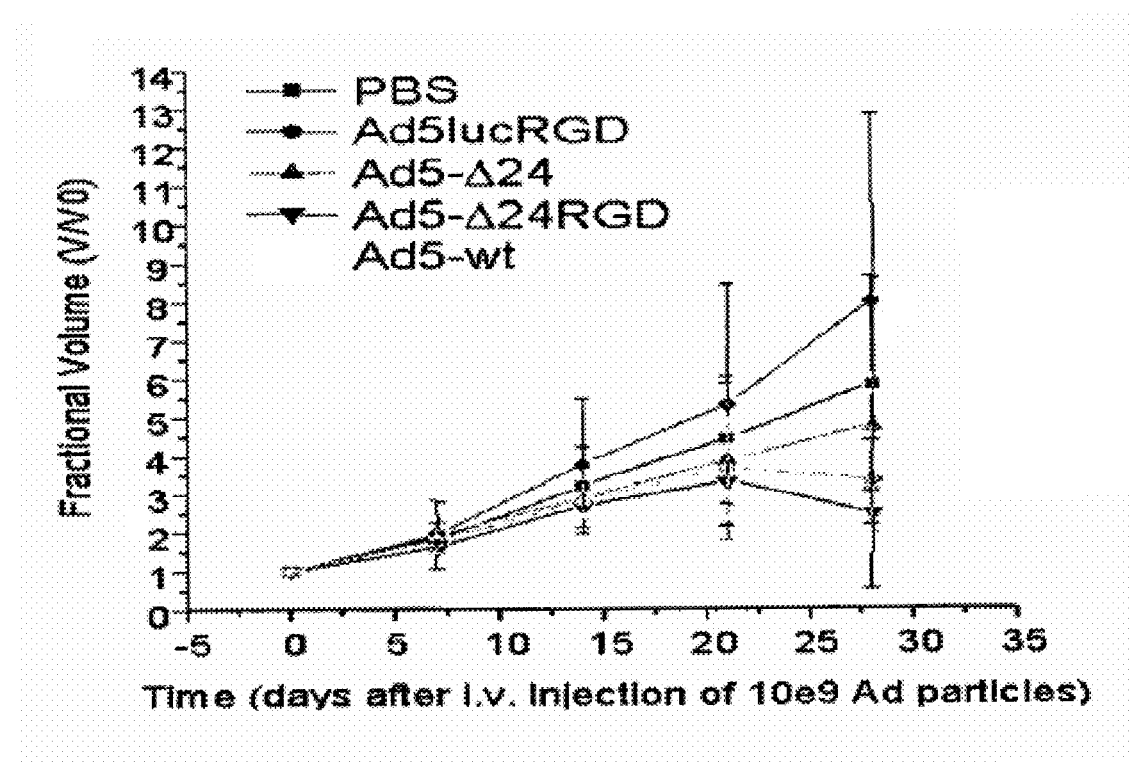
FIG. 16 shows in vivo oncolysis by systemic delivery of infectivity-enhanced CRAds. A total dose of $10^9$ viral particles divided into two consecutive doses of $5 \times 10^8$/day of either Ad5lucRGD, Ad5-D24, Ad5-D24RGD, Ad5-wt, or PBS were injected in the tail vein of nude mice bearing s.c. A549 xenografts. Tumor size was measured weekly. Results are shown as fractional tumor volumes (V/V0, where V=volume at each time point; V0=volume at adenovirus injection), and each line represents the mean of 4 tumors (±SD). The data show that modification of the fiber to broaden the tropism of a replicative adenovirus improves the oncolytic potential in a systemic delivery context.

Enhanced oncolytic potential was also demonstrated in a systemic context. A total dose of $10^9$ viral particles divided into two consecutive doses of $5 \times 10^8$/day of either Ad5IucRGD, Ad5-D24, Ad5-D24RGD, Ad5-wt, or PBS were injected in the tail vein of nude mice bearing s.c. A549 xenografts. FIG. 16 shows that modification of the fiber to broaden the tropism of a replicative adenovirus improves the oncolytic potential in a systemic delivery context.

Conditionally replicative adenoviruses (CRAds) are novel and promising agents for cancer therapy. However, their efficacy is predicated upon efficient tumor infection, specific replication, and lateral spread. The deficiency of coxsackie-adenovirus receptor (CAR) in a variety of tumor targets is a limitation to adenovirus infection. In a previous report, it was demonstrated that the insertion of an RGD motif into the HI loop of the fiber knob of non-replicative adenoviruses enhances tumor infection, indicating that CAR-independent entry represent a viable way to circumvent CAR deficiency in some tumor types.

In this example, it was demonstrated that the genetic introduction of an RGD sequence in the fiber of a CRAd allows CAR-independent infection that leads to the enhancement of viral propagation and oncolytic effect in vitro and in vivo. The increased initial virus entry into the cells rendered by the RGD-modification results in sooner detection and augmented yields of encapsidated DNA of Ad5-D24RGD compared to the unmodified Ad5-D24 (FIG. 13). As this tropism modification is not anticipated to alter fundamental aspects of the viral replication cycle, this effect was likely due to the infectivity enhancement allowed by delivering the virus through CAR-independent pathways. Subsequently, studies of the oncolytic potency of CRAds in two cell lines conclude that Ad5-D24RGD potency is higher than that of the unmodified virus. Although the XTT assay was not sensitive enough to demonstrate the lytic effect of Ad5-D24 compared to the non-replicative Ad5lucRGD, the crystal violet showed early comet-like cytopathic areas in Ad5-D24-treated A549 and LNCaP cells, indicating the presence of an incipient lytic effect, whereas Ad5lucRGD treated cells were intact (FIG. 14). The less notable difference between Ad5-D24RGD and Ad5-D24 seen in LNCaP cells is explained by the absence of the $\alpha v \beta 3$ integrins, compensated by the presence of other types of RGD-binding integrins ($a_3b_1$ and $a_5b_1$) that were rapidly saturated (FIG. 14).

Another object of the present invention was to demonstrate the superior oncolytic effect of Ad5-D24RGD in an in vivo model. To this end, A549 cells xenografted in nude mice were treated with single, high dose ($10^9$ viral particles) i.t. injections of Ad5lucRGD, Ad5-D24, Ad5-D24RGD, or PBS, and the results showed that both CRAds (modified and unmodified) yielded similar oncolysis (FIG. 15A). However, when a 100-fold lower dose ($10^7$ viral particles) was administered, it became clear that the oncolytic effect of Ad5D24RGD was higher than that of Ad5-D24 ($p<0.05$) (FIG. 15B). Furthermore, the observed oncolytic effects were correlated with the presence of virus progeny in the tumor samples by immunofluorescent detection of adenoviral hexon. Hexon was not detected in PBS (not shown) and Ad5lucRGD treated nodules (FIG. 15C, a), whereas it was detected throughout the tumors treated with CRAds. The comparison between the two CRAds showed that fluorescence in Ad5-D24RGD treated tumors was stronger than the one observed in Ad5D24 treated tumors (FIGS. 15C, b and c). The lack of fluorescent staining in tumors treated with the non-replicative control Ad5lucRGD indicates that the detected hexon belongs to the viral progeny of Ad5-D24 and Ad5-D24RGD, and not to the initial inoculum. As regards to the high divergence of the volumes of PBS and Ad5lucRGD treated tumors, factors such as highly heterogeneous cell replication rates and hypoxic and necrotic areas are known to affect individual tumor volume after a critical size is reached. These differences have been noted before when using oncolytic viruses. Nevertheless, total resolution of the tumors in the s.c. xenograft model was seen only in some nodules treated with Ad5-D24RGD, indicating that administration volume and schema adjustments, such as the ones suggested recently by Heise and co-workers (1999), might be necessary to achieve complete oncolysis.

As presented here and elsewhere, the efficacy of replication-competent viruses employed as oncolytic agents can be improved at the level of infectivity. As other tumor binding peptides are isolated (Shinoura et al., 1999; Koivunen et al., 1999), modifications in addition to the RGD insertion can be considered as well. Of note, the RGD-modification described here does not preclude the binding of the fiber to CAR, and the modified virus can enter the cells through $a_v$ integrins and CAR.

One approach to improve specific tumor infection/transduction would be the combination of CAR-ablation and tumor-specific ligands to redirect the virus tropism. Recently, the adenovirus fiber amino acids crucial for CAR-binding abrogation and new tumor-selective peptides have been defined (Koivunen et al., 1999; Roelvink et al., 1999). This combination will generate truly targeted viruses, and the efficiency of their propagation will depend on the amount of the targeted receptor in the same way as the propagation of the unmodified virus depends on CAR. This strategy could be very valuable when the population to be targeted is homogeneous, such as endothelial cells of tumor vasculature.

Other aspects of adenovirus biology that can be improved are replication specificity, tumor cell killing, and evasion from host immune responses. Tumor selectivity has been the major area of research with the design of CRAds based on deletions of adenoviral early genes and utilization of tumor-specific promoters. With regard to cell killing capacity, the combination of oncolysis with suicide genes such as cytosine deaminase and herpes simplex: virus thymidine kinase has demonstrated to be superior to either treatment alone. In a similar way, the combination of oncolysis with radiotherapy and chemotherapy has also proved to have better efficacy. Immune responses will play an important role in the ultimate outcome of oncolytic virotherapy, an ideal scenario would favor a response that can destroy tumor cells, and yet allow viral spread. The manipulation of the immune response against adenovirus towards a Th1 type could lead in this direction. The use of immunocompetent animals will be needed for the study of immune response to adenovirus, and also ovine and canine adenovirus could be useful for this purpose.

Specifically targeted CRAds have theoretical attributes that could make them effective via systemic administration: low toxicity due to lack of adsorption and replication in normal cells and low effective dose due to their amplification. To ascertain whether these agents have enough targeting/amplification potency to be efficacious through systemic administration, the oncolytic efficiency of enhanced infectivity CRAds administered via tail vein in mice would be determined. It seems that not only the presence of CAR and $a_v$ integrin are important for adenovirus infection, but anatomical and immunological barriers are also crucial when considering this route of administration. In particular, vector clearance by liver macrophages is a major obstacle that has to be overcome. This can be attempted with targeting or other strategies that change the physico-chemical properties of the virion such as PEGylation. The emerging picture is that of a targeted adenovirus that remains in circulation for a sufficient period to achieve specific recognition of the target. In such a scenario, the infectivity enhancement maneuvers described herein will clearly improve the therapeutic gain achievable via CRAds.

Example 9

Targeting Endogenous Receptors with Chimeric Replication-Competent Adenovirus Vectors Squamous cell carcinoma of the head and neck (SCCHN) expresses relatively low levels of the primary adenovirus type 5 (Ad5) receptor, coxsackie-adenovirus receptor (CAR). This relative deficiency of CAR has predicated the development of CAR-independent transduction strategies to make adenovirus-mediated cancer gene therapy more efficient for this disease. CAR-independent transduction strategies have been made by a number of methods including the development of adenovirus vectors containing chimeric knob domains that alter the virus target cell tropism. Recently it has been suggested that the receptor for adenovirus type 3 (Ad3) is more highly expressed in SCCHN compared to the Ad5 receptor, thereby making the Ad3 receptor as excellent alternative target for SCCHN. Therefore, it is hypothesized that a chimeric Ad5 vector containing Ad3 knob domains would have preferential targeting to SCCHN compared to an Ad5 vector containing only Ad5 knob domain.

SCCHN cells were infected with equal amount of two oncolytic Ad5 vectors, Ad5luc3 or Ad5/3Luc3. Ad5Luc3 contains an Ad5 knob domain that necessitates CAR-dependent transduction. Alternatively, Ad5/3Luc3 contains an Ad3 knob domain that utilizes a CAR-independent pathway. The apparent disproportion of Ad5 receptors and Ad3 receptors on this tumor type resulted in more efficient infection and replication of Ad5/3Luc3 compared to Ad5Luc3. The ability of Ad5/3Luc3 to more efficiently infect and replicate resulted in a dramatic increase in the oncolytic effect of this virus. Thus, infectivity-enhancement via knob chimerism also improves the oncolytic potency of the CRAd therapy.

Example 10

Evaluation of Tumor-Selective E2 and E4 Functions

One goal of the present invention is to demonstrate that tumor-selective regulation of E4 and E2 can confer tumor-selective replication to adenovirus. It has previously been shown that E4-deleted adenoviruses can be transcomplemented by conjugating an E4 expression plasmid into their capsid. In this regard, plasmids such as pCEP-ORF6, that contain the E4 ORF6 under a constitutive promoter, can be used to transcomplement E4 deleted viruses, such as dl1014. In order to achieve tumor-selective expression of E4-ORF6, tumor-specific promoters are substituted for the CMV promoter. Among several tumor or tissue selective promoters that have been used in restricting expression of genes to tumor cells, the promoter of the prostate specific antigen (PSA) is used initially. PSA is expressed in prostate cells and has been used to direct expression of TK to prostate tumors. This promoter was chosen to control E4 and E2 in the context of replicative adenoviruses because it has already been used to control E1 in this context (obtained from Dr. Chris Baigma). The promoter is subcloned in front of the E4ORF6 in plasmid pCEPORF6 to obtain a pPSA-ORF6 expression plasmid. To evaluate the conditional replicative phenotype of a PSA-ORF6-regulated virus, this plasmid is conjugated with the E4-deleted virus, dl1014. Conjugates with pCEP-ORF6 or irrelevant plasmids are used as positive and negative controls, respectively. These Ad5dl1014 adenovirus-polylysine-plasmid conjugates are used to infect tumor cell lines that express prostate specific antigen, such as LNCaP, and cell lines that do not express prostate specific antigen, such as DU145 or PC3. In time course experiments, viral replication is measured at the DNA level by Southern blot. The amount of virus produced from the molecular conjugates is measured by plaque assays in W162 cells. dl1014 DNA replication and virus production is observed in all cell lines when using pCEP-ORF6, but only in the PSA-expressing cell line, LNCaP, when using pPSA-ORF6. These results indicate that the E4 can be used to control the replication of E4-deleted adenoviruses and the PSA promoter restricts this replication to cells expressing PSA.

As a reference background and for comparison purposes, a PSA-E1 plasmid is constructed as a derivative of the E1 constructs used in the replication-enabling system, such as pE1FR. An E1-deleted vector and 293 cells are used to evaluate the selective replication conditional to the expression of prostate specific antigen. The differential propagation and the levels of virus production obtained with PSA-E4 and PSA-E1 regulation indicates which of these regulatory mechanism renders better selectivity of replication when used independently.

A similar strategy is followed to achieve selective expression of E2. E2-expression plasmids transcomplement E2-defective viruses using the replication-enabling system. The function of the three open reading frames of E2 (DNA binding protein, terminal protein, and polymerase) are subcloned into separate plasmids. These open reading frames of E2 are then placed under the regulation of the PSA promoter. Appropriate E2-defective mutant viruses, such as Ad5ts125 which contains a temperature-sensitive mutation of E2-DBP, are used to construct the corresponding adenovirus-polylysine-DNA conjugates. As above, these conjugates are used to infect LNCaP, DU145 and PC3 cell lines. Viral DNA replication is measured by Southern blot. Cell lines expressing E2 are used to measure the amount of E2-deleted viruses produced by plaque assays.

Example 11

Construction of RGD-Fiber Adenoviruses with Tumor-Selective E4 or E2 Transcriptional Units It is a goal of the present invention to combine the fiber modification with the replication-regulatory mechanisms. Towards this direction, the E4 and/or E2 construct(s) that demonstrated conditional regulation in the replication-enabling system replace the endogenous viral E4 and/or E2 transcriptional unit. For this, the region that is to be modified is subcloned into a small plasmid to facilitate its manipulation. This region is then removed from the plasmid and co-transformed into competent bacteria with a plasmid containing the complete viral genome. The recombination between the viral sequences flanking the modified region and the homologous sequences in the larger plasmid results in the incorporation of the modified region into the adenoviral genome. Before the co-transformation step, it is necessary to cut the large plasmid in a unique site located in the middle of the homology region to avoid the presence of colonies derived from the large plasmid. As there are no available unique sites in the E4 or E2 promoter region, the RecA-assisted cleavage method will be used to restrict in the proper site.

This method involves three steps: first, an oligonucleotide spanning the site to be cut in the E2 or E4 promoter region is annealed to the large plasmid in the presence of RecA protein (New England Biolabs, Beverly, Mass.) to form a three-stranded segment. Second, a methylase recognizing this site is then used to methylate all the sites in the large plasmid except the one protected by the oligonucleotide. Finally, the oligonucleotide is removed by heat and the corresponding restriction endonuclease is used to cut the unique non-methylated site. Common site-specific methylases, such as AluI, HaeIII, HhaI, HpaII, etc, and the corresponding restriction endonucleases are purchased from New England Biolabs. Plasmids containing the wild type fiber and plasmids with the modified RGD fiber are used. After the homologous recombination step, the larger plasmids containing the viral genomes with the substituted E4 or E2 regions are cut with PacI release the viral genome. Finally, the viruses are obtained by transfection into E4 or E2 complementing cell lines. Viruses are amplified and purified by double CsCl gradient, and titered in these cell lines for in vitro and in vivo experiments. The presence of the E4 or E2 transcription unit regulated with the tumor-specific promoter and of the mutated fiber is analyzed by PCR as well as by sequencing of viral DNA isolated from CsCl-purified virions.

Example 12

Testing of Adenoviruses with Enhanced Infectivity and Tumor-Selective Replication Mice containing human tumors can be used to evaluate the therapeutic potential of adenoviruses with enhanced infectivity and tumor-selective replication. Three types of models can be used: subcutaneous engrafted cell lines (e.g. prostate LNCaP and DUI45), diffuse intraperitoneal engraftments (e.g. ovarian SKOV3-ipl), and liver metastases (e.g. colorectal carcinoma cell line LS174T). Adult (6-8 week old) athymic nu/nu mice can be used in the subcutaneous and metastatic models whereas SCID mice can be used in the intraperitoneal model. Except for the prostate cell lines, female mice are used. Treatments include the RGD-modified, non-modified and vehicle control in a single injection for each dose. Intratumoral, intraperitoneal or intravenous administration of the viruses (according to the model used) is performed with unsedated mice using gentle physical restraint. All mice are euthanized at the conclusion of all experiments by $CO_2$ vapor sedation followed by Phenobarbital overdose.

Localized Models

Subcutaneous tumor nodules can be established using the LNCaP and DU145 cell lines. Cells ($10^7$) are mixed 1:1 with Matrigel (Collaborative Bioproducts), loaded into syringes and injected subcutaneously in a total volume of 200 µl into the front flanks of athymic nude mice ($2 \times 10^6$ cells per engraftment site). Initially, three pairs of viruses are compared: PSAE4-RGD versus PSAE4; PSA-E2 versus RGD-PSAE2; and PSA-E1 versus RGD-PSAE1. Viruses with double E1/E4 or E1/E2 controlled transcriptional units can also be analyzed. Tumor nodules are injected with the appropriate adenovirus or vehicle control (PBS/10% glycerol) when their volume (length×width $2 \times \frac{1}{2}$) reaches 0.2 mm$^3$. Injections are with a Hamilton syringe in a volume of 20 µl ($\frac{1}{10}$ of tumor volume). The amount of virus injected per tumor is adjusted from $10^4$ pfus (plaque forming units) to $10^8$ pfus by serial dilution. A series of experiments are done to measure the tumor volume until regression or a maximum of 1 cm$^3$. Another series of experiment are performed to measure the intratumoral amount of virus in a time course. This amount is measured by resecting the tumors and staining sections with anti-hexon antibody (Chemicon) and by extracting the virus from the tumors and measuring the viable virus in a plaque assay. In DU145 tumors, no therapeutic effect is observed with the PSA-controlled viruses. In LNCaP tumors, smaller tumors or complete tumor regressions is observed, and more intratumoral virus in tumors treated with the PSA-controlled replicative viruses is observed when compared to the non-replicative and vehicle control treated tumors. Smaller tumors or more frequent complete regressions are observed, likely due to higher amounts of intratumoral virus with the ROD-modified vector. These results demonstrate that the tumor-specific regulation of adenoviral genes, such as E4, allows replication in vivo in permissive tumors and also demonstrates the therapeutic advantage of the RGD modification for a replicative adenovirus.

Local-Regional and Disseminated Models

A murine model for ovarian cancer and liver metastases of colon cancer has been developed. These models have been useful in demonstrating the utility of the RGD modification for non-replicative adenoviral vectors, and therefore, are used herein in the context of replicative adenoviruses containing tumor-specific promoters. The ovarian cancer model is a local-regional model that uses the human ovarian cancer cell line, SKOV3.ipl. As these cells express SLPI, this model is useful to evaluate viruses in which the E4 or E2 gene is regulated by the SLPI promoter. This cell line has been serially passaged in SCID mice and selected for its ability to grow aggressively in the peritoneum. Female SCID mice receive an i.p. injection of $2 \times 10^7$ cells in 0.5 ml of serum-free medium. Five days after injection, tumors start to form at the peritoneum surface and the progression of the disease mimics the human disease. One week after injection, the viruses (RGD-modified or the unmodified control) will be injected i.p. in a volume of 100 µl. The therapeutic viruses are also intravenously injected. Virus dosages range from $10^4$ pfus to $10^8$ pfus. The therapeutic effect is measured by surviving cells. The amount of replicating virus is measured in peritoneal lavages in time course experiments.

The model of colon cancer liver metastases uses LS174T human colon cancer cells and allows for expression of genes under the CEA promoter. In a surgical operation, cells ($5 \times 10^8$) are injected along the long axis of the spleen. Five minutes after the injection, the splenic vessels are tied off and the spleen is cut and removed. After the abdominal wall and skin are sutured, extensive liver metastases form in 7-10 days. Tail vein injection of RGD-modified and unmodified replicative adenoviruses to demonstrate systemic treatment using this model. Liver metastases are counted in a time course experiment after virus injection.

These experiments provide in vivo data demonstrating selective replication and oncolytic potency of replicative vectors with restricted replication and enhanced infectivity. The RGD modification in the fiber of replicative adenoviruses, along with tumor-selective expression of E4 or E2 in addition to E1, increases the virus' propagation efficacy and ultimately its therapeutic efficacy.

Example 13

VEGF Promoter-Based Conditionally Replicative Adenovirus

In this example, the inventors exploited the expression of vascular endothelial growth factor (VEGF) in tumors for therapeutic advantage. Several studies have shown that angiogenesis is one of the key control factors in the growth, progression, and metastasis of solid tumors. Among the many known angiogenic factors, such as bFGF, angiogenin, IL-8, PD-ECGF, VEGF is now believed to play a pivotal role in tumor-associated angiogenesis in a number of solid tumors.

A conditionally replication-competent adenovirus (CRAd) was constructed in which the expression of the adenoviral E1 gene was controlled by the human VEGF promoter. This virus achieved high levels of viral replication in lung cancer cells and induced a substantial anti-tumor effect in vitro and in vivo. Further enhancement of the anti-cancer cell killing effect was achieved with tropism modification of the virus via serotype chimerism of the adenoviral fiber knob. These infectivity-enhanced VEGF promoter-based CRAds also showed a significant cell killing effect for various types of cancer cells other than lung cancer. In this regard, a dysregulated VEGF axis is characteristic of many carcinomas. On this basis, this current CRAd agent may be useful as a "pan-carcinoma" therapeutic agent.

Cell Culture

The NCI-H82, NCI-H460, NCI-H157, NCI-H322, NCI-H522, NCI-H1299, NCI-H358, NCI-N417, A427, A549 lung cancer cell lines; BEAS-2B, normal human bronchial epithelial cell line; Panc-I, pancreas cancer cell line; and HEK293 adenoviral transformed human embryonic kidney cell line were obtained from ATCC (American Type Culture Collection, Manassas, Va.). QG56 and QG90 were provided by National Kyushu Cancer Center, Fukuoka, Japan. Human ovarian adenocarcinoma cell line SKOV3.ipl was obtained from Dr. Janet Price (M.D. Anderson Cancer Center, Houston, Tex.). The MeWo cell line was obtained from Dr. Ian R. Hart (St. Thomas Hospital, London, UK). Cells were cultured in the media recommended by each provider and incubated at 37° C. and 5% $CO_2$.

Adenovirus Vectors

The recombinant adenoviral vectors that express firefly luciferase were constructed through homologous recombination in *Esherichia coli* using the AdEasy system (He et al., 1998). The 2.6 kb human VEGF promoter region derived from pVEGF-kpnI (Forsythe et al., 1996) was placed in front of the firefly luciferase gene in an Ad E1 shuttle vector, recombined with the E1- and E3-deleted adenoviral backbone vector pAdEasy 1, then transfected into 293 cells by standard techniques to form Ad5VEGFLuc. The luciferase gene and simian virus 40-polyadenylation signal were derived from pGL3 Basic (Promega, Madison, Wis.). As a control, a vector containing the ubiquitously active cytomegalovirus (CMV) immediate early promoter (derived from plasmid pCEP4; Invitrogen, Carlsbad, Calif.) instead of the VEGF promoter was also constructed and named Ad5CMVLuc.

The replication competent adenovirus, Ad5VEGFE1 was also generated from the same E1- and E3-deleted adenoviral backbone vector. Briefly, the fragment corresponding 489 bp to 3533 bp from the left end of the type 5 adenoviral genome was amplified by PCR and inserted in the E1 deleted region of the backbone vector. This fragment contains the transcriptional start site of the E1A gene but not the native E1A promoter. The 2.6 kb VEGF promoter region was placed upstream of this fragment. A control vector was also constructed in which the CMV promoter was placed in the same position upstream of E1A. The strategy for these constructs is summarized in FIG. 17. Fiber modified CRAd, Ad5/3VEGFE1 was generated in similar manner as Ad5VEGFE1 but using Ad5/3E1-E3-deleted backbone vector derived from Ad5/3luc1 containing Ad3 knob in place of Ad5 wild-type knob gene as described previously (Krasnykh et al., 1996). To compare the differences in infectivity between the Ad5 and Ad5/3 chimeric vectors on the target cells, an Ad vector (Ad5/3luc1) that contains a CMV driven luciferase gene in E1 was compared to AdCMVLuc. Wild type p53 protein expressing adenovirus, Ad5p53 which contains CMV driven p53 cDNA was provided from Dr. Ueno (University of Occupational and Environmental Health, Kitakyusyu, Japan) (Takayama et al., 1998)

The viruses were propagated in the adenovirus packaging cell line, 293HEK, and purified by double CsCl density gradient centrifugation, followed by dialysis against phosphate-buffered saline with 10% glycerol. The viral particle (VP) concentration was determined spectrophotometrically, using a conversion factor of $1.1 \times 10^{12}$ viral particles per absorbance unit at 260 nm, and standard plaque assays on 293 cells were performed to determine infectious particles.

Analysis of VEGF RNA Expression

The VEGF RNA status of cell lines was analyzed by reverse transcription and polymerase chain reaction (RT-PCR) as described previously (Ohta et al., 1996). Total cellular RNA was extracted from $1 \times 10^7$ cells using the RNeasy kit (Qiagen, Valencia, Calif.) and analyzed for VEGF and glyceraldehydes-3-phosphate dehydrogenase (GAPDH) RNA with the GeneAmp RNA PCR core kit (Applied Biosystems) as described by manufacturer. Briefly, 500 ng of total RNA was reverse-transcribed with the random hexamer and murine leukemia virus reverse transcriptase (50° C., 30 min) and amplified by PCR with 50 nM of primer pairs described below using a cycling program (initial step of 95° C. for 15 min, 27 cycles of 95° C. for 1 min and 60° C. for 1 min and 72° C. for 1 min, final step of 72° C. for 10 min). The primers used for the analyses were as follows: VEGF sense, 5'GAAGTGGTGAAGTTCATGGATGTC3', SEQ ID NO:6; VEGF antisense, 5'CGATCGTTCTGTATCAGTCTTTCC3', SEQ ID NO:7; GAPDH sense, 5'CCTTCATTGACCTCAACTA3', SEQ ID NO:8; GAPDH antisense, 5'GGAAGGCCATGCCAGTGAGC3', SEQ ID NO:9.

Measurement of VEGF Protein in Culture Media

The VEGF protein expression was evaluated as described previously. Briefly, $1 \times 10^5$ cancer cells were cultured for 24 h in serum free media, and then the medium was collected. After centrifugation, the supernatant was stored at −80° C. until the assay. The VEGF protein in the culture medium was determined using an ELISA kit (Quantikine Human VEGF Immunoassay, R&D Systems, Minneapolis, Minn.) according to the manufacturer's instructions. Each of the values given here is the mean of triplicate determination with respect to standardized cell numbers, $1 \times 10^5$ cells.

In Vitro Analysis of VEGF Promoter Activation

The activity of the VEGF promoter in an adenovirus context was analyzed by infection of cells with luciferase expression vectors as reported previously (Adachi et al., 2001). Briefly, cells were plated in 12-well plates in triplicate at a density of $1 \times 10^5$ cells/well. The next day, the cells were infected with Ad5VEGFLuc or Ad5CMVLuc at a MOI of 10 pfu/cell in DMEM with 2% FCS for 3 h and then maintained in complete medium. The infected cells were harvested and treated with 100 ml of lysis buffer (Promega, cat #E153A) after 2 days culture. A luciferase assay (Luciferase Assay System; Promega) and a FB12 luminometer (Zyluc corporation) were used for the evaluation of luciferase activities of Ad-infected cells. Luciferase activities were normalized by the protein concentration in cell lysate (Bio-Rad DC Protein Assay kit).

In Vivo Analysis of VEGF Promoter Activation

For determination of luciferase gene expression in mouse organs, nude mice (Charles Rivers) received $1 \times 10^9$ pfu of Ad5CMVLuc or Ad5VEGFLuc by tail vein injection as described previously (Adachi et al., 2001). Two days later, mice were sacrificed, and the livers, kidneys, lungs, spleens were resected to measure the luciferase gene expression. The resected organs were placed in the polypropylene tubes, and immediately frozen in ethanol/dry ice. Frozen tissues ground to a fine powder was lysed using a tissue lysis buffer (Promega), and then luciferase activity was determined using a luciferase assay kit (Promega). The luciferase activity was normalized by protein concentration in the tissue lysate.

Analysis of Viral Genome Amplification

Viral DNA amplification was assessed as reported previously (Adachi et al., 2001). Cells were plated in a 12-well culture plate in triplicate at the density of $1 \times 10^5$ cells/well. After overnight culture, cells were infected with replication-competent Ads (Ad5VEGFE1, Ad5CMVE1 or Ad5 wt) or non-replicative Ad (Ad5CMVLuc) at the MOI of 10 for 3 h and then cultured for 24 h. The harvest of infected cells was followed by viral DNA isolation using Blood DNA kit (Qiagen, Valencia, Calif.). Viral DNA was eluted with 100 ml of elution buffer [10 mM TrisCl (pH 8.5)]. Eluted samples (1 ml) were analyzed by real-time PCR analysis to evaluate Adenoviral E4 copy number using a LightCycler (Roche). Oligonucleotides corresponding to the sense strand of Ad E4 region (5'-TGACACGCATACTCGGAGCTA-3', 34885-34905 nt, SEQ ID NO:10), the antisense strand of E4 region (5'-TTTGAGCAGCACCTTGCATT-3', 34977-34958 nt, SEQ ID NO:11), and a probe (5'-CGCCGCCCATGCAACAAGCTT-3', 34930-34951 nt, SEQ ID NO:12) were used as primers and probe for real-time PCR analysis. The PCR conditions were as follows: 35 cycles of denaturation (94° C., 20 s), annealing (55° C., 20 s), and extension (72° C., 30 s). Adenovirus backbone vector pTG3602 (Chartier; Transgene, Strasbourg, France) was available for making a standard curve for Ad E4 DNA copy number. E4 copy numbers were normalized by the b-actin DNA copy number.

In Vitro Cytotoxicity Assay

For determination of virus-mediated cytotoxicity, $5\times10^3$ cells were plated in 96-well plates in triplicate. After overnight culture, cells were infected with each Ads at various MOI for 3 h. The infection medium was then replaced with RPMI1640 containing 10% FCS. Viable cells using MTS assay (CellTiter 96 Aqueous Non-Radioactive Cell Proliferation Assay; Promega) were evaluated every 3 days. The MTS color development was quantified as optical density at 490 nm by an EL 800 Universal Microplate Reader (Biotec Instruments Inc.)

To visualize the cytotoxic effect, crystal violet staining was also performed. Cells ($2\times10^5$) were plated in 12-well plates and infected with each Ad at various MOI for 3 h. The infection medium was replaced with growth medium the next day. When cell lysis was observed, cells were fixed and stained with 1% crystal violet in 70% ethanol for 45 min, followed by washing with tap water to remove excess color. The plates were dried, and images were captured with a Kodak DC260 digital camera (Eastman Kodak, Rochester N.Y.). All experiments were performed in duplicate wells.

In Vivo Studies—Tumor Formation in Nude Mice

Tumor suppressive effect in vivo was analyzed as described previously (Takayama et al., 2000). Briefly, H157 cells ($5\times10^6$) were injected s.c. into the dorsal skin of nude mice, and tumor growth was monitored for 25 days. Tumor volume was calculated according to the formula $a^2 \times b$, where a and b are the smallest and largest diameters, respectively as described previously. When tumor formation was seen 10 days after inoculation, $1\times10^8$ pfu of each virus was injected into the tumor directly. Student's t test was used to compare tumor volumes, with $p<0.05$ being considered significant.

VEGF mRNA and Protein Expression in Various Cell Lines

Figure 18A:
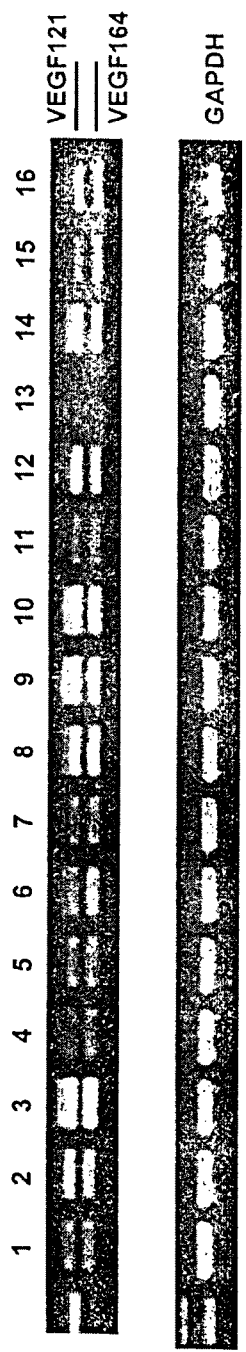
FIG. 18A shows VEGF mRNA expression in various cell lines. The RT-PCR product for VEGF121 (408 bp), VEGF165 (541 bp) or GAPDH (574 bp) is shown in upper or lower panel respectively. Lane 1, H82; lane 2, H460; lane 3, H157; lane 4, H322; lane 5, H522; lane 6, H1299; lane 7, QG56; lane 8, QG90; lane 9, A427; lane 10, H358; lane 11, A549; lane 12, N417 (lanes 1-12 are lung cancer cell lines); lane 13, BEAS-2B, a normal bronchial epithelial cell line; lane 14, SKOV3.ipl, ovarian cancer cells; lane 15, MeWo, melanoma cells and lane 16, Panc-I, pancreatic cancer cells.

The inventors first investigated a panel of twelve non-small cell lung cancer cell lines, one bronchial epithelial cell line (BEAS-2B) as a normal cell control, one ovarian cancer cell line (SKOV3.ipl), one gastric cancer cell line (MKN28), and a pancreatic cancer cell line (Panc-I) for VEGF mRNA expression using a RT-PCR method. In this regard, there are four structural variants of VEGF (VEGF121, VEGF165, VEGF189, and VEGF206) resulting from alternative mRNA splicing in the regions encoding the cytoplasmic domains. FIG. 18A shows amplification of a 408 bp fragment (representing VEGF121 cDNA) and a 541 bp fragment (representing VEGF165 cDNA) in all cell lines tested. The intensity of each band (VEGF121 and VEGF165) was similar in all cancer cells tested. The PCR bands corresponding to VEGF189 (615 bp) and VEGF206 (666 bp) were minimal or not detected, indicating VEGF121 and VEGF165 were the dominant isoforms in these cell lines. These results are consistent with those of previous similar studies of primary lung cancer tissues. Of the cells tested, H157, A427, N417, H358 and SKOV3.ipl showed relatively high expression of VEGF mRNA, while the control normal cell line BEAS-2B showed a less intense band than the cancer cell lines, although the band corresponding to VEGF121 was detected at very low levels.

Figure 18B:
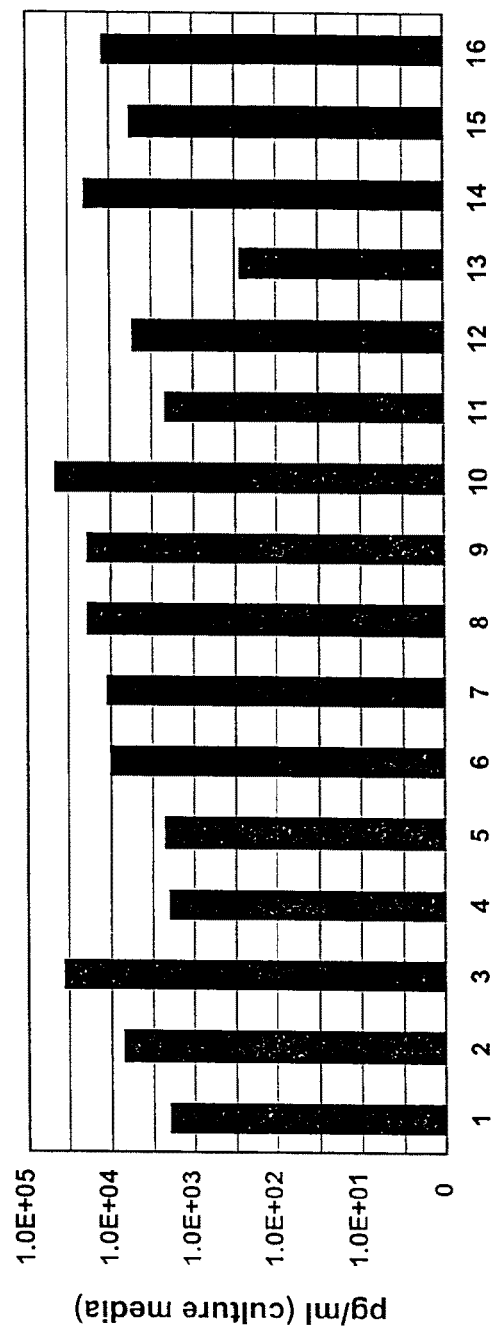
FIG. 18B shows VEGF protein expression in the same cell lines. $1 \times 10^5$ cancer cells were cultured for 24 h in the serum free media. The VEGF protein concentration in the media was measured by ELISA. Mean+SE of triplicate determination is shown.

The correlation between mRNA expression and protein expression for VEGF was also investigated. As shown in FIG. 18B, the VEGF protein expression levels also varied between cell lines. H157 secreted the highest amount of VEGF protein into the culture media, and the concentration was over 100 times higher than that of BEAS-2B. Comparison between FIGS. 18A and 18B revealed that the VEGF mRNA expression level positively correlated with VEGF protein expression level. These results thus suggested the VEGF promoter activity can be predicated from the VEGF protein concentration of tumor cellular substrates.

Transgene Expression by VEGF Promoter in the Ad Context In Vitro

Candidate tumor-specific promoters may lose their specificity when placed in the context of the Ad genome. Thus, the VEGF promoter activity was assessed in an Ad vector (Ad5VEGFluc) containing the luciferase gene as a reporter. This was examined in several cell lines that represented the range of VEGF levels detected in FIG. 18. In all of the cells lines tested, luciferase expression was achieved using the positive control Ad5CMVLuc, which contains the luciferase gene driven by the non-selective viral CMV promoter. These results demonstrate that the A247 and H157 cells were most susceptible to Ad5 infection, exhibiting luciferase levels over 100 times higher than these of H460 as shown in upper panel of FIG. 19. To standardize the differential susceptibility to Ad5 infection between cell lines, VEGF promoter activity is thus shown as the percentage of luciferase activity of Ad5VEGFLuc relative to Ad5CMVLuc. As shown in the lower panel in FIG. 19, H157 cells showed the strongest VEGF promoter activity which was 28% of CMV promoter activity. In contrast, BEAS-2B cells, which presented the lowest VEGF promoter activity, was less than 0.1% of CMV. This low transgene expression seen with the VEGF promoter in the adenoviral context with BEAS-2B was consistent with other recent reports. Other cell lines demonstrated various VEGF promoter activities which correlated with the mRNA expression level for each cell lines tested (FIG. 18A). Based on these data, it is concluded that the VEGF promoter was able to induce transgene expression in VEGF producing cells and, importantly, that the promoter retained its specificity when configured in the Ad genome context.

Transgene Expression by VEGF Promoter in the Ad Context In Vivo

A key limitation of adenovirus-mediated cancer gene therapy is the potential for toxicity to non-target organs. Because Ad exhibits a marked tropism for the liver, it is important to determine whether the VEGF promoter would have low activity in the liver in vivo. Such a "liver off" phenotype would be critical to avoid any toxic effects of VEGF promoter CRAd therapy. Normal liver was reported to exhibit minimal VEGF expression.

Figure 20:
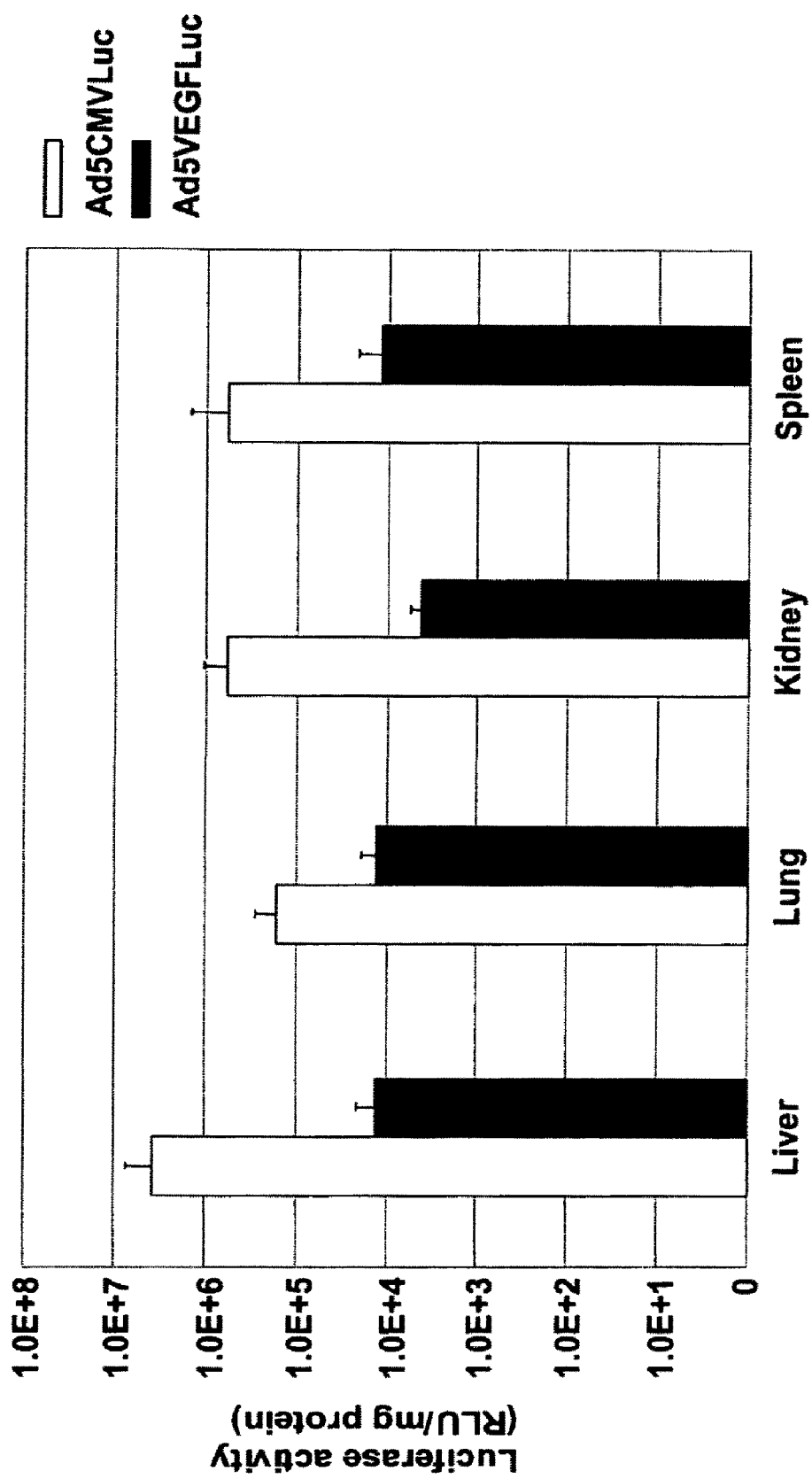
FIG. 20 shows tissue specificity of the VEGF promoter in the adenoviral context. Mice received $1 \times 10^9$ pfu of Ad5VEGFLuc or Ad5CMVLuc via tail vein injection (three per group). Two days after virus injection, mice were sacrificed to obtain the organ samples. Each organ lysate was assayed for luciferase activity and normalized for protein concentration. Mean+SE of triplicate determination is shown.

On this basis, Ad5VEGFLuc or Ad5CMVLuc (as a positive control) were injected i.v. via the tail vein into mice and the level of transgene expression at day 2 was determined (FIG. 20). In this assay, transgene expression in the liver induced by the VEGF promoter was a mean 270-fold less than that seen with the CMV promoter. These results thus confirm the key property of VEGF promoter fidelity in vivo in the context of the Ad vector used. Furthermore, the "liver off" phenotype of the VEGF promoter makes the use of a VEGF promoter CRAd feasible in a systemic delivery context.

VEGF Promoter Driven CRAd Shows Replication Specificity

Figure 17:
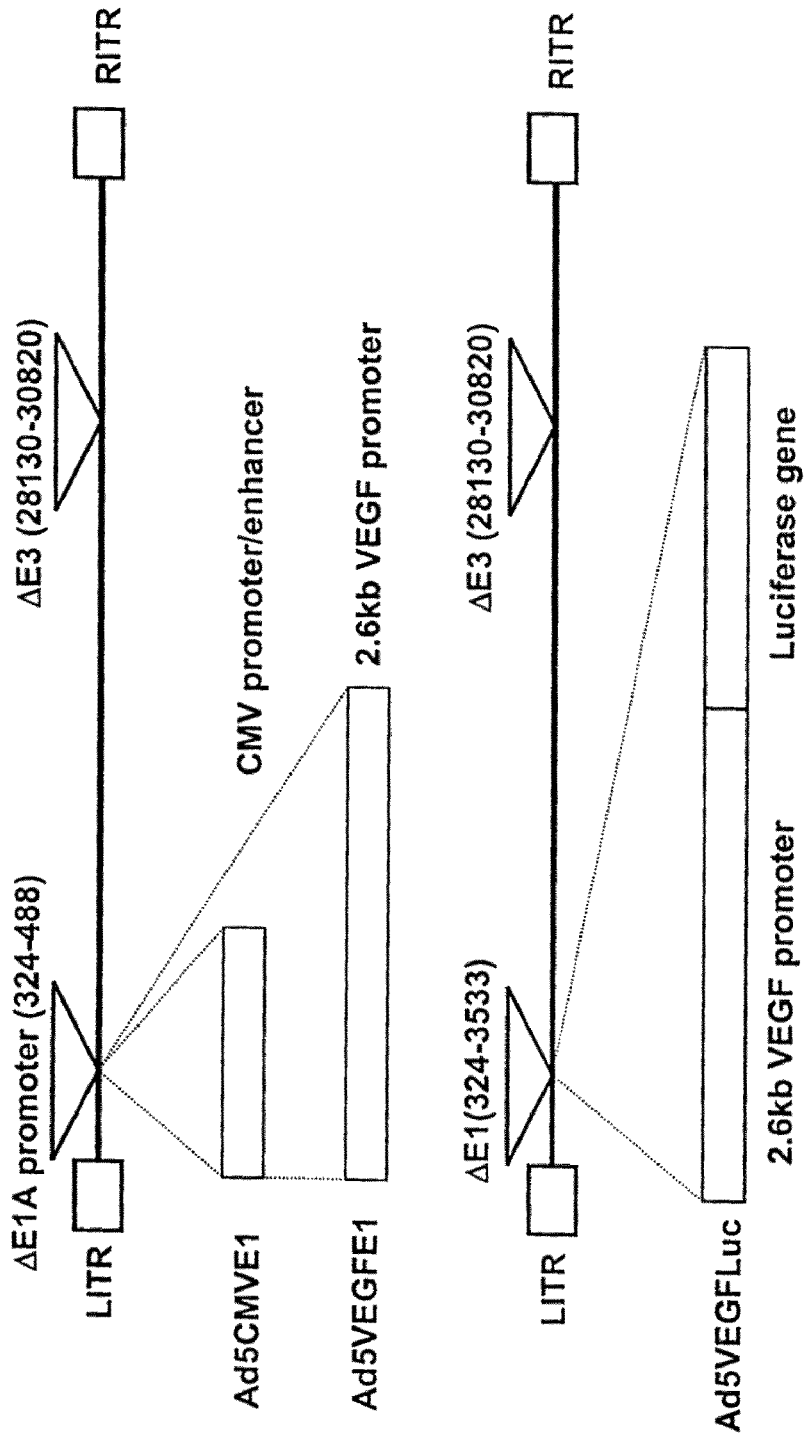
FIG. 17 shows schematic diagrams of Ad vectors containing VEGF promoter. These vectors are constructed from an E3 region-deleted Ad5 backbone and do not contain the Ad E1A promoter region (from nucleotides 324 to 488 of the Ad genome). Deletion of the E3 region was necessary due to the length of the 2.6 kb VEGF. AdCMVE1 and AdVEGFE1 differ in the promoter driving E1A expression.

To exploit the cell specificity of the VEGF promoter in a CRAd context, the inventors then constructed a recombinant Ad (Ad5VEGFE1) in which the native E1 promoter was replaced with the 2.6 kb human VEGF promoter. The genomic structures of replication competent Ads used in this study are depicted in FIG. 17. An Ad in which E1 expression is controlled by the non-selective viral CMV (Ad5CMVE1) promoter was used as control. These viruses are deleted in the E3 region to accommodate the large VEGF promoter and the E1A gene region. The deleted E1A promoter region, containing the native E1A TATA box, was replaced with either the VEGF promoter or CMV enhancer/promoter to produce the viruses Ad5VEGFE1 or Ad5CMVE1, respectively.

Figure 21:
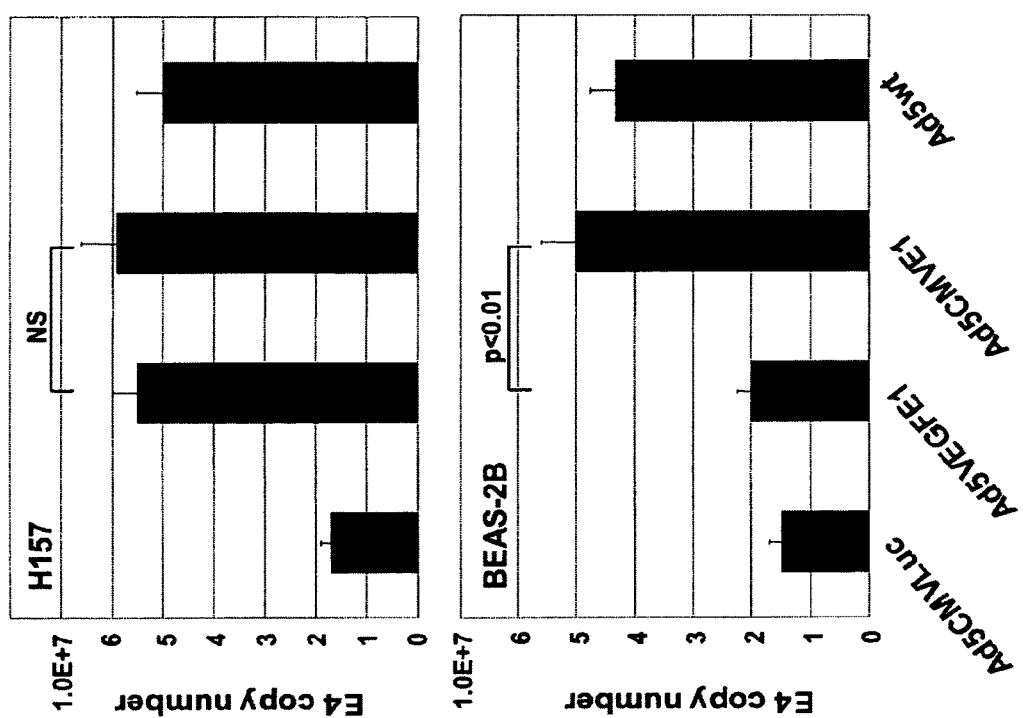
FIG. 21 shows viral DNA replication 24 h after infection. $1 \times 10^5$ cells were infected with replication-competent Ads (Ad5VEGFE1, AdSCMVE1 or Ad5wt) or non-replicative Ad (Ad5VEGFLuc) at an MOI of 10 for 3 h and then cultured for 24 h. Viral DNA was isolated from the cells and analyzed by real-time PCR analysis to evaluate adenoviral E4 copy number. E4 copy numbers were normalized by the b-actin DNA copy number. Mean+SE of triplicate determination is shown.
Figure 22A:
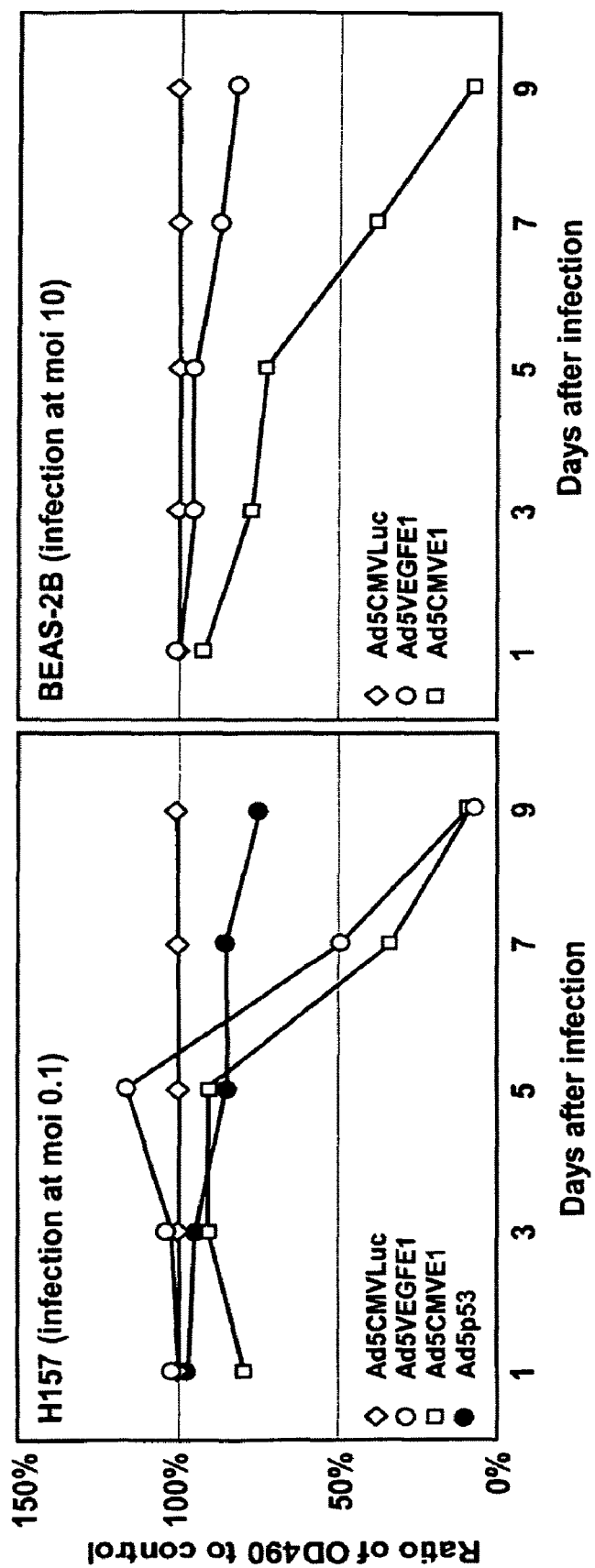
FIG. 22A shows the cell killing effect of AdVEGFE1 evaluated by MTS assay. $5 \times 10^3$ H157 cells were infected with Ad5CMVLuc (negative control), Ad5CMVE1 (positive control), or Ad5VEGFE1 at MOI of 0.1. After infection cell viability in each well was quantified by MTS assay every three days. The cell viability of cells infected with Ad5VEGFE1 or Ad5CMVE1 is expressed as the percentage of the OD490 value to control cells infected with Ad5CMVLuc (100%). BEAS-2B cells were infected with each Ad at MOI 10 and evaluated by MTS assay in the same manner.
Figure 22B:
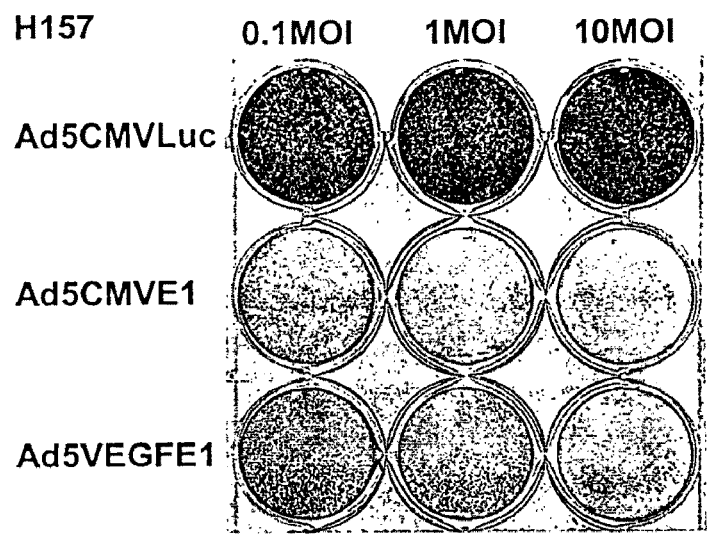
FIG. 22B shows the cell killing effect of AdVEGFE1 evaluated by crystal violet staining $2 \times 10^5$ H157 cells and BEAS-2B cells were infected with each Ad at MOI 0.1, 1.0 or 10. All wells were stained by crystal violet 9 days after infection to visualize viable cells.
Figure 22B:
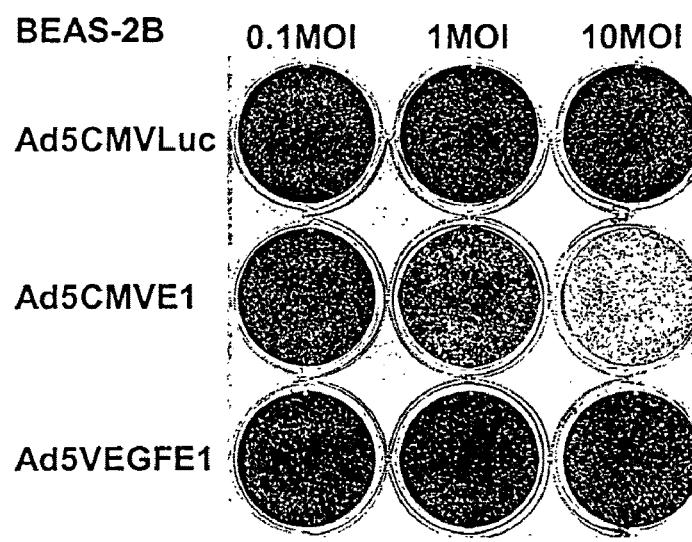

To determine the specificity of replication of the AdVEGFE1, the high VEGF expressing cell line (H157) and low expressing cell line (BEAS-2B) were infected with the Ad vectors, and then quantitative real-time PCR was used to determine the level of amplification of viral DNA. The nonreplicative Ad5CMVLuc and wild-type Ad5 virus (Ad5 wt) were used as negative and positive controls, respectively. Since all viruses tested contained the Ad E4 region, viral DNA was quantified by E4 copy number via real-time PCR. As shown in the upper panel of FIG. 21. the Ad5VEGFE1 viral genome replicated in the high VEGF producing cancer cells H157 to a similar extent as did the Ad5CMVE1 genome. The nonreplicative Ad5CMVLuc showed a background level of E4 signal, indicating no replication in this cell line. Importantly the replicative capacity of Ad5VEGFE1 decreased in the low VEGF expressing BEAS-2B cells, with values 3-logs lower than that for Ad5CMVE1 (lower panel in FIG. 21). These results indicate that the VEGF promoter retains fidelity in the replication competent adenoviral context and mediates tumor-specific adenoviral replication.

Specific Cell Killing Efficacy of VEGF Promoter-Driven CRAd

The ability of Ad5VEGFE1 to achieve cell killing in the VEGF-positive cell lines was determined using a MTS assay. The viability of the high VEGF expressing H157 cells and the low VEGF expressing BEAS-2B cells was quantified every three days after virus infection as shown in FIG. 21A. For the H157 cells. Ad5VEGFE1 showed cytotoxic effect as strong as that of the Ad5CMVE1 positive control virus. All cancer cells were killed by day 9 with infection at a low MOI. The relatively steep fall in the survival curve after day 5 suggested a minimal temporal requirement before sufficient replication occurred to induce toxicity.

To reconcile these results with an alternative gene-based approach to cancer treatment which has been proposed, the Ad5VEGFE1 cytotoxic effect was compared with that of Ad5p53, which encodes the wild-type p53 gene and has been employed in human clinical trials. In this regard, it has previously been shown that H157 cells, which have a mutated p53 gene, undergo apoptosis when infected with Ad5p53. Ad5p53 infection of H157 cells at MOI 0.1 showed a weak cytotoxic effect compared with Ad5VEGFE1. Similar results were obtained with A427 cells (data not shown). In contrast to the effect in the cancer cells, BEAS2B cells were resistant to Ad5VEGFE1 toxicity even with infection at a high MOI of 10. These data were consistent with the crystal violet staining appearance as shown in FIG. 21B.

Tumor Growth Suppression by Ad5VEGFE1 In Vivo

Figure 23:
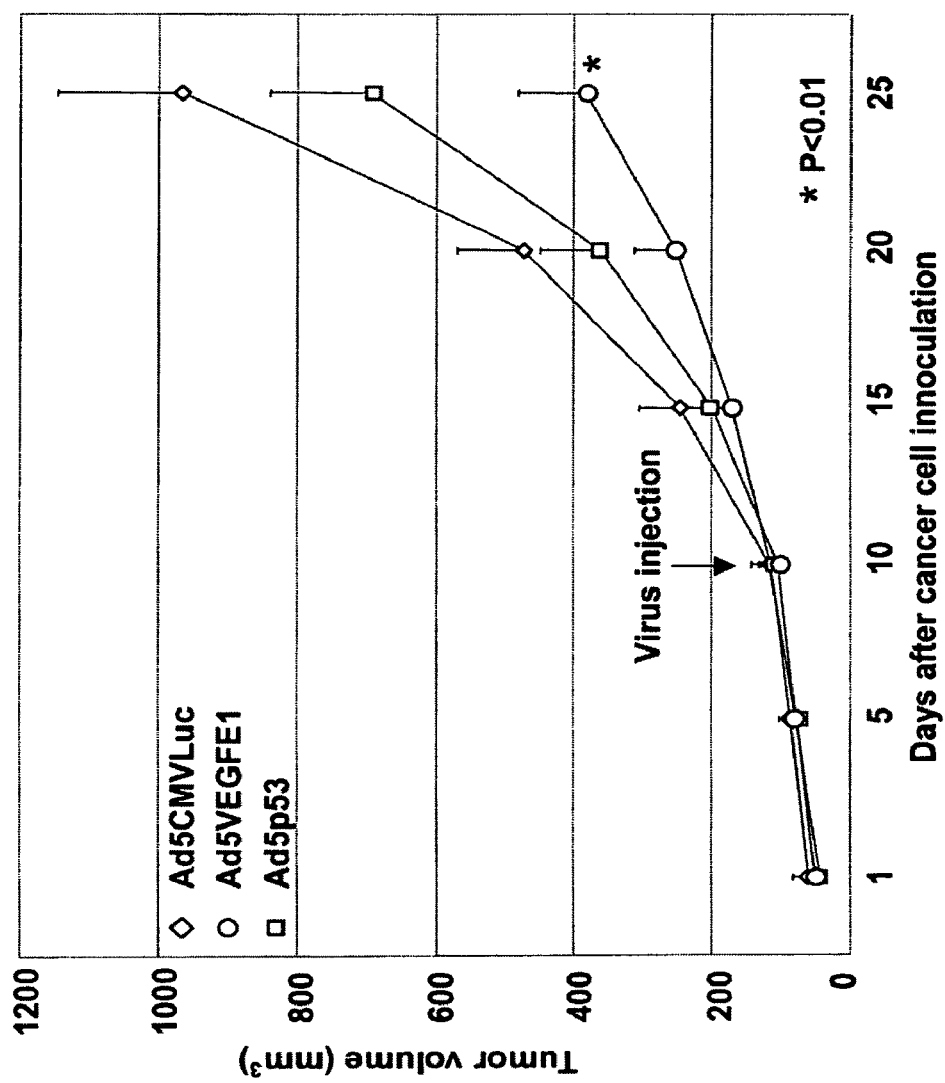
FIG. 23 shows Ad5VEGFE1 suppressed tumor growth in vivo. Intact H157 cells ($5 \times 10^6$) were injected s.c. into nude mice. When tumor formation was seen 10 days after inoculation, $1 \times 10^8$ pfu of each virus (diamond, Ad5CMVLuc; circle, Ad5VEGFE1; square, Ad5p53) was injected into the tumor directly. Three similar sized tumors were injected with each virus, and the mean volume+SE is shown.

The inventors next investigated whether Ad5VEGFE1 could suppress tumor growth in vivo. To this end, subcutaneous tumors established in nude mice were directly injected with either Ad5CMVLuc, Ad5VEGFEI or Ad5p53. Tumors become visible and injectable 10 days after subcutaneous inoculation. Previous work revealed that the inoculated H157 cells have completed angiogenesis at this time, and in this regard resemble advanced human tumors (Takayama et al., 2000). For these studies, $1 \times 10^8$ pfu of each virus was injected into the tumor directly and each tumor was observed for 2 weeks. As shown in FIG. 23, tumor injected with Ad5CMVLuc increased in size. Ad5p53 suppressed tumor growth partially; however, the suppressive effect was minimal. In contrast, Ad5VEGFE1 suppressed the tumor growth to a significantly greater degree than Ad5p53. These findings suggested that CRAd may be a more efficacious agent than non-replicative virus-based gene therapy approaches such as Ad5p53.

Improvement of CRAd Potency Via Fiber Modification

Figure 19:
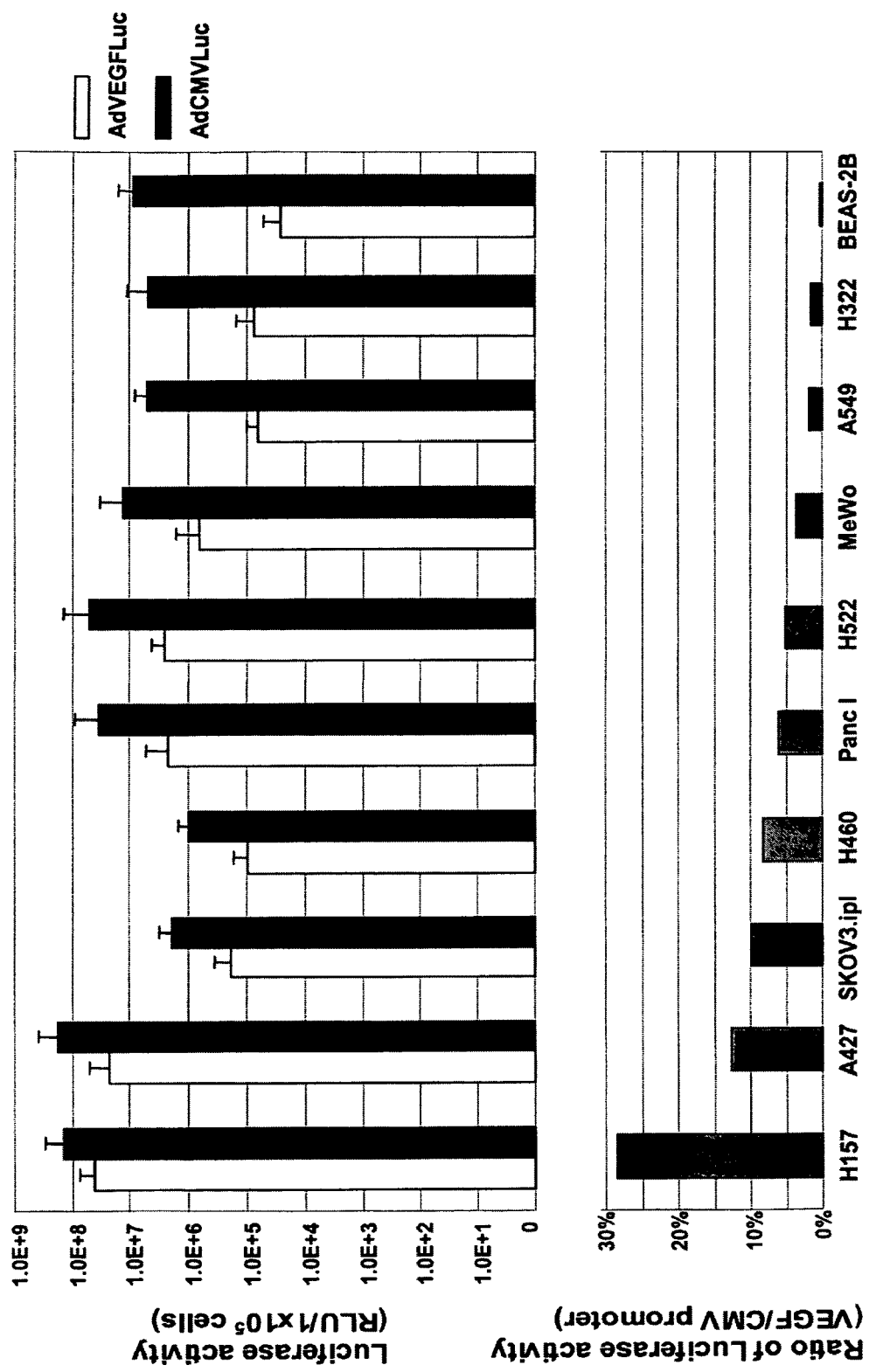
FIG. 19 shows transgene expression by VEGF promoter in the Ad context in vitro. Upper panel shows luciferase activities in various cell lines infected by Ad5CMVLuc or Ad5VEGFLuc. $1 \times 10^5$ cells of each cell line were infected with Ad5CMVLuc or Ad5VEGFLuc for 3 h at MOI 10. Cells were harvested 48 h after infection and lysed in 100 ml of lysis buffer. Ten ml of each lysate was used for luciferase assay. Mean+SE of triplicate determination is shown. Lower panel shows the ratio of VEGF promoter activity to CMV promoter activity. To standardize the VEGF promoter activity in each cell line, the luciferase activity with Ad5VEGFLuc was expressed as the percentage of luciferase activity with Ad5CMVLuc.

The oncolytic effect of any CRAd is dependant on the infectivity of the cancer cells as well as promoter activation specificity. Based on these concepts, the inventors endeavored to achieve improvement of adenovirus infectivity as a means to enhance the anticancer effect achieved via the CRAd agent. In this study, it is noted that adenovirus infectivity for H460 lung cancer cells and SKOV3.ipl ovarian cancer cells was almost 2 orders of magnitude lower than that of H157 and A427 lung cancer cells (FIG. 19). This differential infectivity is likely the basis of differential CRAd efficacy noted in these contexts. In this regard, it has been previously reported that infectivity of serotype 5 adenovirus can be improved by fiber modifications. For example, a modified adenovirus with a chimeric fiber which expresses Ad3 knob instead of Ad5 knob. (Ad5/3) showed enhanced infectivity for various tumor cells that was otherwise Ad refractory.

Figure 24:
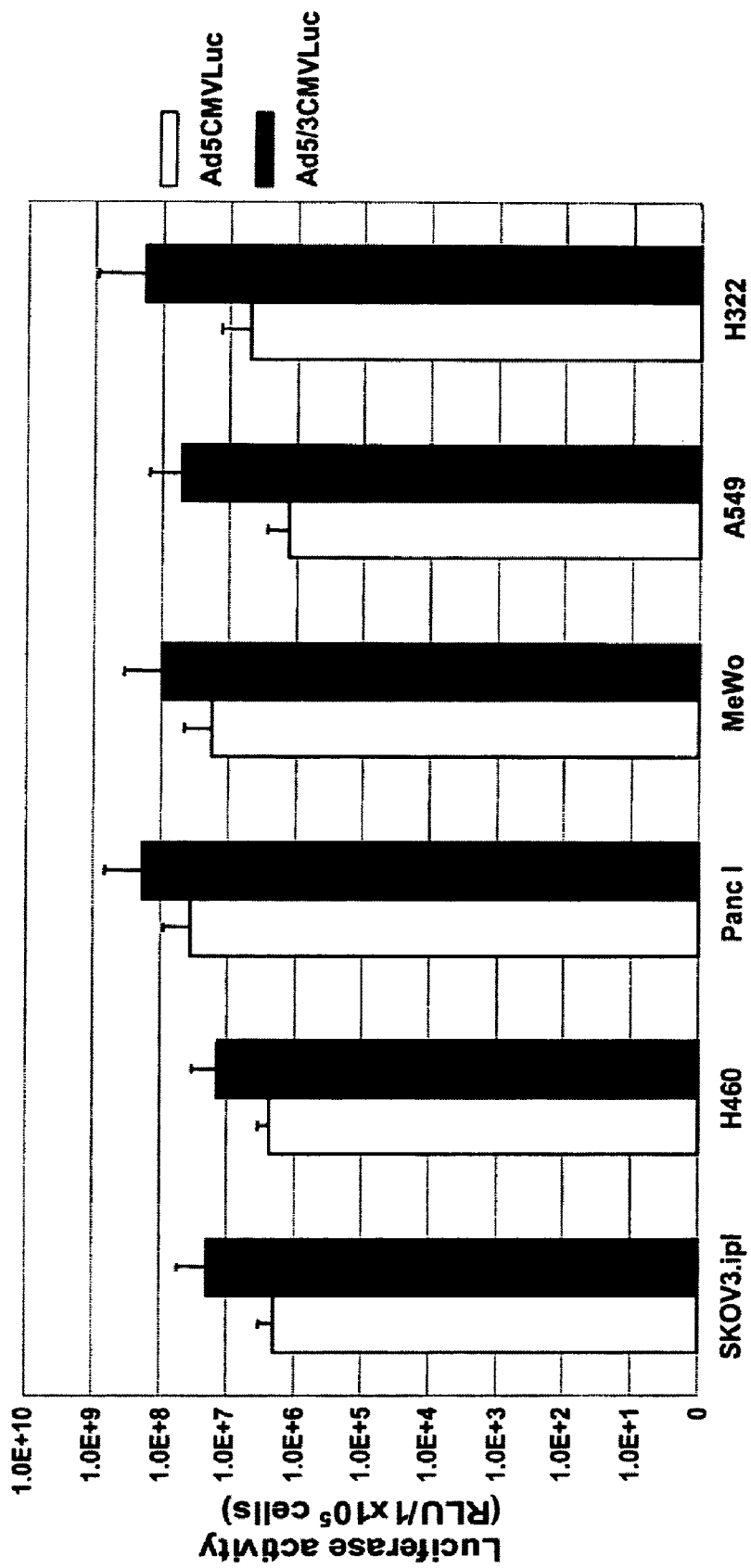
FIG. 24 shows enhancement of infectivity to cancer cells with Ad5/3 chimeric vector. $1 \times 10^5$ cells of each cell line were infected by Ad5CMVLuc or Ad5/3luc1 at MOi 10. Infected cells were harvested 48 h after infection and lysed in 100 ml of lysis buffer. Ten ml of each lysate was used for luciferase assay. Mean+SE of triplicate determination is shown.
Figure 25:
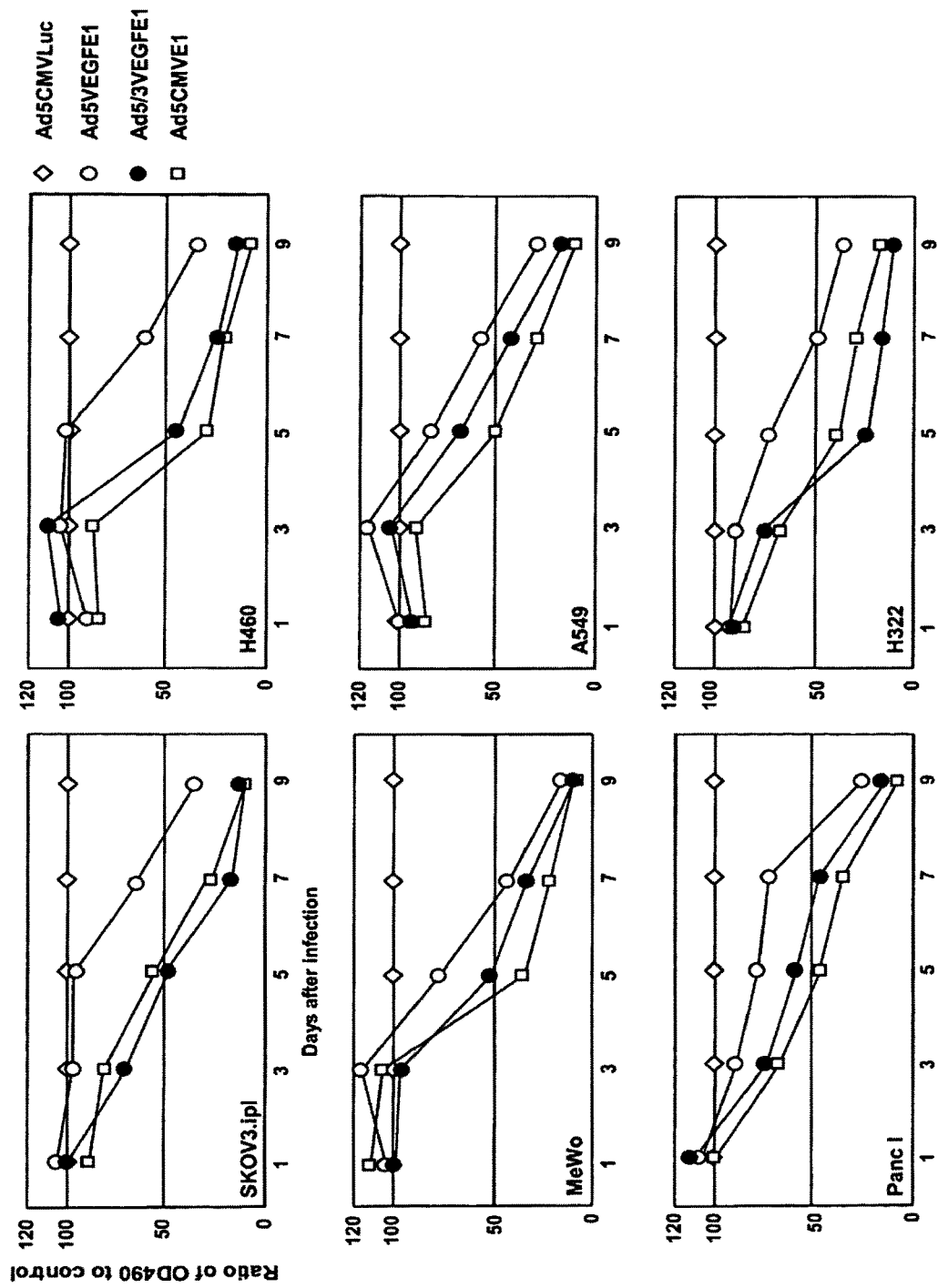
FIG. 25 shows enhancement of cell killing with Ad5/3 chimeric CRAd. Cell killing effect was evaluated by MTS assay. $5 \times 10^3$ cells of each cell line were infected with Ad5CMVLuc (negative control), Ad5CMVE1 (positive control), Ad5VEGFE1 or Ad5/3VEGFE1 at MOI of 1.0. After infection cell viability in each well was quantified using OD490 by MTS assay every three days. The viability of cells infected with Ad5CMVE1, Ad5VEGFE1 or Ad5/3VEGFE1 was expressed as a percentage of cells infected with Ad5CMVLuc (100%).

The inventors therefore analyzed the effect of infectivity enhancement via knob serotype chimerism for the cell lines tested in this study. As shown in FIG. 24, the luciferase activities with the Ad5/3 vector increased in all 6 cell lines tested. The increases observed were between 5.1 times in Panc I cells and 39.4 times in A549 cells. These findings led the inventors to construct an Ad5/3VEGFE1 in which the Ad5 knob is replaced with Ad3 knob. Ad5/3VEGFE1 was generated and propagated as described in Materials and Methods. The oncolytic effect of Ad5/3VEGFE1 relative to Ad5VEGFE1 for the various cancer cells was evaluated using infection at 1 MOI (FIG. 25). Cytopathic effect with Ad5/3VEGFE1 infection was seen rapidly. almost 2 days earlier than that with Ad5VEGFE1 in all cell lines. In this experiment, complete cell death was seen for all lines infected with Ad5/3VEGFE1 nine days after infection whereas a significant number of cells survived with Ad5VEGFE1 infection. Moreover. Ad5/3VEGFE1 showed a stronger cell killing effect for H322 cells and SKOV3.ipl cells compared with Ad5CMVE1. These results suggested that infectivity enhancement with modified adenovirus fiber could improve the cell killing effect of the VEGF promoter CRAd.

Conditionally replicative adenovirus (CRAd) represents a promising new therapeutic approach for malignancies resistant to conventional treatments. The current example demonstrates a strategy based on the use of a replication-competent Ad controlled by a VEGF promoter. Furthermore, it is demonstrated that AdVFEGFE1 is applicable for the treatment of a wide spectrum of tumors. With regard to gene therapy of lung cancer, replication incompetent Ad expressing wild-type p53 is currently being employed in human clinical trials. While replication-incompetent viral vectors have demonstrated great promise as anticancer agents in preclinical studies, this has not been translated into patient benefit in the clinical setting. The poor anticancer effect with replication-incompetent Ad is partly due to limited penetration of the vector into the tumor mass. In this regard, CRAd agents are designed to achieve intratumoral spread and penetration by virtue of their replicative capacity.

For clinical application, prevention of hepatic toxicity by adenoviral agents is an important consideration. Tumor cells infected with replication-competent Ad may release new viruses in vivo. Such dissemination could predicate treatment related toxicity, especially in the context of the liver as this is the predominant site of Ad vector localization after systemic injection. In this regard, the present example shows that the VEGF promoter exhibits extremely limited promoter activity in the liver and thus may avoid untoward hepatic injury. Since AdVEGFE1 exhibited a high degree of specificity in both replication and cytotoxicity which correlated with target cell VEGF expression, it would be predicated to be less toxic to the liver compared with AdCMVE1 or wild-type Ad. Results of a phase I clinical trial with VEGF inhibitors showed that these agents were well tolerated, indicating a marginal role for VEGF signaling in normal organs under physiological conditions except the ovary during the menstrual cycle.

An emerging strategy for cancer therapy is the use of conditionally replicative adenoviruses (CRAds) that are designed to exploit key differences between tumor cells and normal cells to allow tumor-selective viral replication and oncolysis. Two basic strategies have been employed to generate CRAds. A type I approach, such as Ad-dl1520 (ONYX-015) or AdD24, involves directly mutating Ad genes such as E1 to take advantage of the disordered cell cycle regulation in tumor cells with functionally deficient p53 or RB signaling, respectively. The type II approach involves replacement of wild-type Ad promoters with tumor-specific promoters to drive the expression of genes essential for Ad replication.

A consideration for the clinical employment of type II CRAd is that the relevant promoter activity in each tumor should be confirmed before treatment. In this regard, it is clear that tumors with low promoter activity are resistant to type II CRAds containing that promoter. Therefore it is important to evaluate the promoter activity a priori to avoid potentially non-indicated therapy. Analysis for RNA status requires tissue obtained from the patient to prepare RNA samples for RT-PCR or northern blotting. Precise evaluation of promoter activity with a reporter gene such as luciferase is more difficult in the clinical setting generally. Considered in this context, it is clear that the VEGF promoter has an advantage for its activity evaluation. Results in FIGS. 18 and 19 demonstrated that there is a positive correlation between VEGF mRNA expression level, VEGF protein expression level, and transgene activation by the VEGF promoter. Taken together these data suggest that the VEGF promoter activity within a tumor can be predicted from VEGF protein expression levels. Of note, VEGF protein is easily detectable in clinical samples by ELISA evaluation of fluid samples and immunohistochemical staining of tissue samples. Thus these tests can potentially be employed to prospectively select the most appropriate patients for consideration of VEGF promoter CRAd therapy in the clinical setting.

VEGF production is an important mechanism for the development of tumor-associated angiogenesis in many types of tumors. In fact, many types of cancer are already known to express VEGF protein at significant levels and this VEGF expression is associated with poor prognosis in several disease contexts including leukemia, breast cancer, colorectal cancer, hepatocellular carcinoma, ovarian cancer and non-small cell lung cancer. It appears that more advanced stage tumors actually express higher levels of VEGF protein. Of note, VEGF gene expression is known to be regulated transcriptionally. Although several transcription factors bind to the cis-elements on the promoter, hypoxia inducible factor (HIF) is the key factor for activation of the promoter. In this regard, the central regions of tumors are often hypoxic and necrotic due to decreased blood flow. Immunohistochemical analysis of primary tumor samples shows that VEGF protein expression is enhanced in the tumor tissue adjacent to necrotic regions. On the other hand, some types of cancer are known to express the HIF protein constitutively despite the oxygen tension, leading to an increase VEGF promoter activation. Taken together these findings suggest that the antitumor effect of AdVEGFE1 may be even more efficacious in large in vivo tumors than under the normoxic conditions under which the above in vitro experiments were performed.

The cell killing effect of a type II CRAd may be improved by several mechanisms such as promoter induction, infectivity enhancement, or an armed CRAd strategy. A major obstacle to be overcome in Ad5-based cancer gene therapy has been the paucity of the primary receptor, CAR, which frequently characterizes human primary tumor cells. Furthermore, down regulation of CAR may be associated with a more malignant phenotype. Due to variable expression of CAR on human primary cancer cells, the utility of Ad5 as a cancer gene therapy vector may be compromised, limiting the overall efficacy of any Ad-based cancer gene therapy, including the use of CRAds agents. On this basis, approaches to circumvent tumor-associated CAR deficiency are required. In this regard, the native Ad5 tropism can be modified to enhance Ad infectivity. One approach is pseudotyping, i.e., retargeting Ad by creating chimeric fibers possessing knob domains derived from alternate serotypes which bind to receptors other than CAR. To this end, nonreplicating Ads containing chimeric fibers with the tail and shaft domains of Ad serotype 5 and the knob domain of serotype 3 have been constructed (Krasnykh et al., 1996). Previous work has revealed that a distinct Ad3 receptor exists in ovarian cancer cells, and that the Ad5/3 chimeric vector is retargeted to the Ad3 receptor. Based on these findings, a CRAd exploiting the Ad5/3 chimeric approach was constructed in this study. Results presented above indicate that Ad5/3VEGFE1 showed a stronger cell killing effect than that of the Ad5-based CRAd, likely on this basis of conferred infectivity enhancement.

In conclusion, the data presented here provide a basis for the advancement of replication-competent adenovirus strategies based on the VEGF promoter for the therapy of various cancers. Furthermore, a CRAd based on the Ad5/3 chimeric vector is a promising way to enhance the anti-tumor potency via infectivity enhancement for cancer cells. Given the relevance of a dysregulated VEGF axis in a broad spectrum of tumor types, as well as the frequency of deficient adenoviral receptor CAR in the context of epithelial neoplasms, the current infectivity enhanced VEGF promoter CRAd may represent a "pan-carcinoma" CRAd with broad potential utilities.

Example 14

CXCR-4 or Survivin Promoter-Based Conditionally Replicative Adenovirus

The enormous promise of CRAd vectors for cancer gene therapy has been established and has resulted in the rapid clinical translation of this approach. The present example provides a CAR-independent vector that was rendered selectively replicative via the CXCR4 or survivin promoter. These vectors have improved transductional efficiency and specificity required for human clinical trials and allow full realization of the potential benefits of the CRAd approach for breast cancer.

Derivation of A Novel, CAR-Independent Ad Vector

Many clinically relevant tissues are refractory to Ad5 infection due to negligible CAR levels. Some non-human Ads display CAR-independent infection of human cells. Canine adenovirus type 2 (CAd2) infects human cells via CAR, but also displays CAR-independent infection of CAR-negative human cells with identical entry kinetics to Ad5 (Soudais et al., 2000). To create an Ad vector for infection of CAR-deficient cells, a "knob-switching" technology (Krasnykh et al., 1996) was employed to engineer a non-replicative, E1a- deleted Ad vector, AdCK/CMV-Luc, which contains the knob domain of the canine adenovirus type 2 (CAd2) and a luciferase reporter gene. The AdCK/CMV-Luc vector was rescued in HEK 293 cells, and the correct chimeric fiber DNA sequence was confirmed. This novel Ad was propagated in HEK 293 cells, and was grown to high titers and purified by traditional methods.

Figure 26:
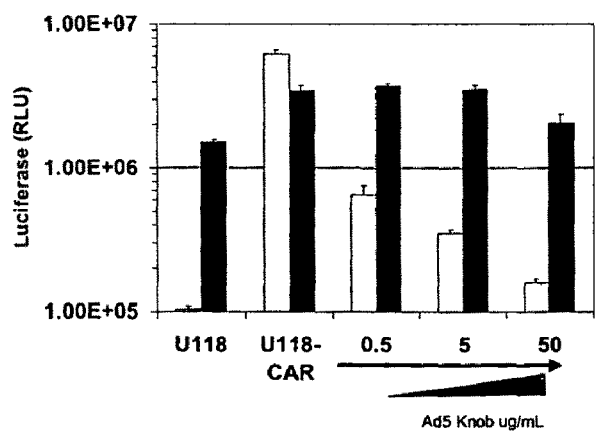
FIG. 26 shows AdCK/CMV-Luc (black) demonstrates CAR-independent tropism versus Ad5/CMV-Luc (gray) in CAR-negative U118 cells and in the presence of increasing free Ad5 knob in CAR-positive UI18-CAR cells. 100 viral particles/cell, n=4, Bar=S.D.

To confirm that AdCK/CMV-Luc displays CAR-independent infection, infection assays were performed on human glioma cells, U118-CAR that was engineered to express human CAR, and the parental CAR-negative U118 cells. In CAR-negative U118 cells, AdCK/CMV-Luc showed 15-fold higher luciferase activity than the isogenic control, Ad5/CMV-Luc (FIG. 26). Furthermore, in U118-CAR cells, AdCK/CMV-Luc had similar luciferase activity to Ad5/CMV-Luc. Importantly, addition of excess recombinant Ad5 knob protein blocked Ad5/CMV-Luc infection, but not that of AdCK/CMV-Luc, indicating AdCK/CMV-Luc has novel, CAR-independent tropism. In addition, AdCK/CMV-Luc demonstrated a 10-fold infectivity enhancement in ovarian SKOV3.ipl vs. Ad5/CMV-Luc (data not shown).

Initial Characterization of Potential Breast Cancer-Selective Promoters

The inventors have obtained full length human CXCR4 and survivin promoters for evaluation as breast cancer-specific promoters for CRAd agents. CXCR4, identified as co-receptor for HIV-1, is also a chemokine receptor recently implicated in the metastatic homing of breast cancer cells to alternate tissues. CXCR4 gene expression is markedly upregulated in breast cancer cells, but is undetectable in normal mammary primary epithelial and stromal cells. Expression of survivin, a member of the inhibitor of apoptosis (IAP) family, is associated with loss of apoptosis in breast cancer, and is a significant prognostic parameter of poor outcome. Over 70% of stage I to IH breast carcinomas have been shown to express survivin, with undetectable expression levels in adjacent normal differentiated tissues or stromal cells.

Figure 27:
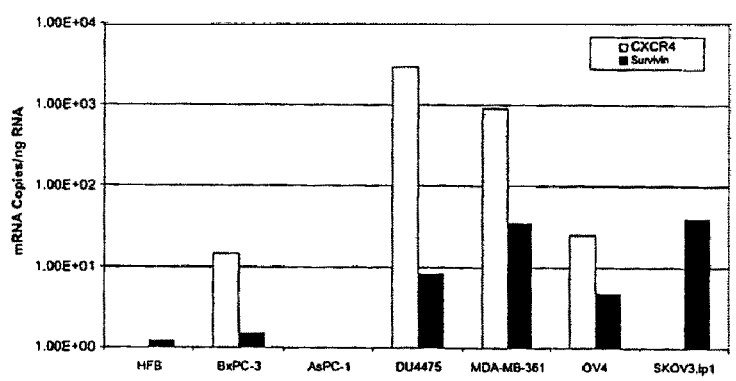
FIG. 27 shows real-time PCR quantification of CXCR4 (gray) and Survivin (black) mRNA in various cell lines. Data expressed as copies/ng total RNA.
Figure 28:
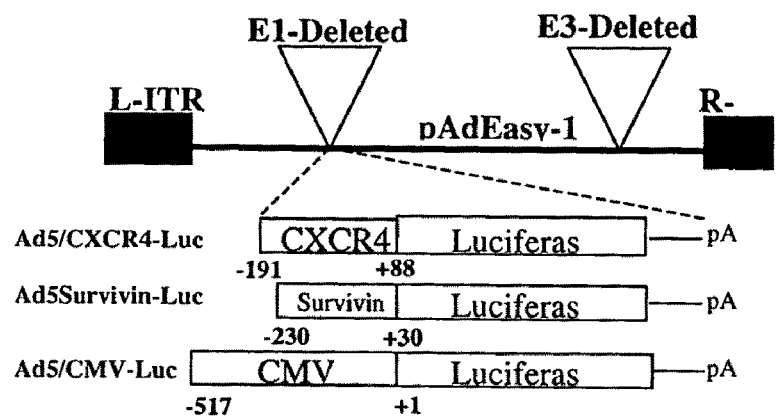
FIG. 28 shows schematic of vectors Ad5/CMV-Luc, Ad5/CXCR4-Luc and Ad5/Survivin-Luc. Promoter region is indicated for each.
Figure 29:
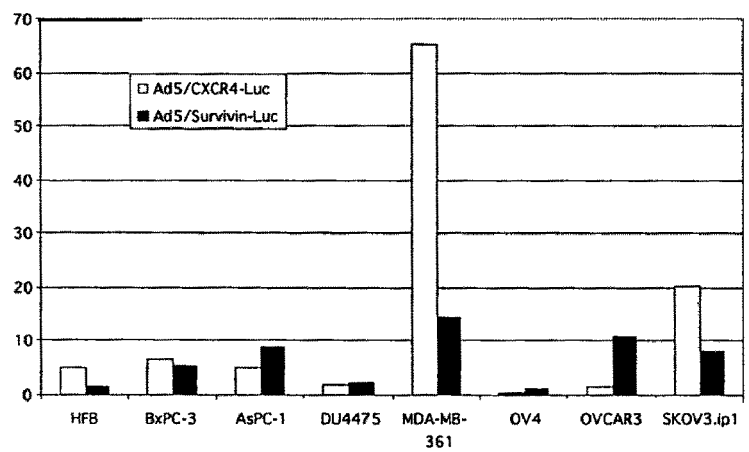
FIG. 29 shows luciferase activities as percent of Ad5/CMV-Luc for Ad5/CXCR4Luc and Ad5/Survivin-Luc at 48 h. 50 pfu/cell, n=3.

To verify the overexpression of CXCR4 and survivin in breast cancer cells, real-time PCR mRNA analysis was performed in two breast cancer cell lines, DU4475 and MDA-MB-361 (FIG. 27). Both cell lines showed elevated survivin and very high CXCR4 mRNA levels compared with human fibroblast (HFB), prostate (BxPC-3 and AsPC-1) or ovarian (OV4 and SKOV3.ipl) cancer cells. To evaluate promoter specificity in the Ad genome context, a panel of non-replicative Ad vectors was constructed with a luciferase reporter gene under the transcriptional control of the CXCR4 (Ad5/CXCR4-Luc) and survivin (Ad5/survivin-Luc) promoters (FIG. 28). As expected, luciferase activities were elevated in MDA-MB-361 breast cancer cells, expressed as percent of Ad5/CMV-Luc (FIG. 29).

Evaluation of CAR-Independent Breast Cancer CRAd Agents for Improved Oncolytic Potency Preliminary data clearly show that the CAR-independent vector, AdCK/CMV-Luc, provides substantial infectivity enhancement for CAR-deficient substrates. The CAd2 knob domain can be incorporated into the fiber of the CXCR4 and survivin CRAds via well established recombinational strategies. The viral replication and oncolytic cells killing activities of the newly derived CAR-independent CRAds can be compared to their wild-type counterparts as follows. Various doses of CRAds are added to target cells in culture. At various time points, cells are evaluated for CRAd replication using automated PCR-based assay based on the TaqMan approach. Crystal violet staining of infected plates, plus MTT/XTT viability assays can be used to provide indices of replication-induced oncolysis. Various input m.o.i's will be evaluated and dose equivalencies established. The CAR-independent CRAds should achieve increased oncolysis at lower m.o.i., indicating their increased potency. As an additional assay, the inventors will employ a spheroid cell culture system that provides growth of cell lines and primary cultures in a three-dimensional configuration. This novel system allows determination of efficacy of agents that operate via "amplification", such as CRAds. These studies will determine the relevance of infectivity enhancement for the context of breast cancer CRAds. CRAd agents that provide breast cancer-specific replication as well as increased breast cancer infectivity will allow early definition of a lead agent for further pre-clinical development Analysis of Therapeutic Utility in Murine Model Systems Studies accomplished to this point will establish a "lead agent" for further evaluation. The use of a murine xenograft model system will provide a means to determine the therapeutic utility of this agent. For therapeutic analysis studies, SCID mice are xenotransplanted subcutaneously with human breast cell lines, including MDA-MB-231 cells. This model will be challenged with the CRAd agent via distinct routes: intratumoral, intraperitoneal and intravenous. The former route parallels treatment of loco-regional disease via CRAd delivery. The latter route parallels systemic delivery relevant to disseminated disease. Tumors will be harvested post-treatment and assayed for CRAd replication via TaqMan PCR. Direct three-dimensional measurement of tumor regression can be performed as a function of time and viral dose. Control agents include non-replicative Ad, as well as replicative wild-type Ad. Comparisons are also made between the CAR-independent CRAd, and its native-tropism counterpart, and control Ads. Ectopic localization of CRAd occurs largely in liver. Thus, this organ provides the best index of CRAd-induced toxicity. Therefore, treated animals will undergo histopathological analysis for evidence of CRAd-related pathology. These efficacy and toxicity studies will provide direct insight into the therapeutic index of these CRAd agents, and predict the pre-clinical/clinical pathway for a human breast cancer clinical trial with the novel CRAd agents.

Example 15

Uses of Survivin Promoter in Double Targeting to Ovarian Carcinoma

This example discloses double targeting for ovarian cancer cells in vitro and in vivo that involves transductional targeting and transcriptional targeting. Transductional targeting is achieved by retargeting adenoviral vector to tumor-specific cell surface markers, such as epidermal growth factor receptor (EGFR), by a bi-functional adaptor or modified fiber of adenoviral vector. Transcriptional targeting can enhance tumor specificity by using a tumor-specific promoter (such as surviving promoter) to restrict transgene expression to tumor cells. It is anticipated that ovarian tumor specificity will be enhanced by targeting based on a tumor specific promoter, survivin, and a retargeting site, EGFR, which is overexpressed in ovarian cancer; and the toxicity to normal tissue will be limited by enhancing tumor specificity and decreasing the dose of administration.

Transductional Targeting by EGFR-Retargeted Adenoviral Vector

Several human ovarian cell lines have been chosen for this study. To determine EGF receptor expression on cell surface by flow cytometry, cells ($10^4$) are sorted on FACScan flow cytometry after treated with $1^{st}$ antibody (5 mg/ml) mAb 425, a monoclonal antibody anti-EGFR and $2^{nd}$ antibody (5 mg/ml), a goat anti-mouse IgG labeled with FITC.

Adenoviral vector will be targeted to EGF receptor by using a fusion protein sCAR-EGF encoded by the construct pFBsCAR6hEGF. The donor plasmid pFBsCAR6hEGF will be transformed into competent DH10Bac E. coli cells to generate a recombinant Bacmid. The fusion protein sCAR-EGF will be produced in High Five cells, purified with NI-NTA resin, and detected by Western Blot.

To compare EGFR-targeted Ad gene transfer among human ovarian cancer cell lines, human ovarian cancer cells ($5 \times 10^4$ cells) will be infected with AdGL3BCMV (M.O.I.=100) pre-incubated with various doses of the sCAR-EGF fusion protein (0, 5, 15, and 20 mg) at room temperature for 30 min. Forty-eight hours post-infection, the luciferase activity will be determined with the luciferase Assay System on the lumicount. A competition test will be performed by using mAb A-431 to block retargeting site on the surface of tumor cells.

Transcriptional Targeting Using Survivin Promoter mRNA levels of survivin are over expressed in the ovarian cell line, SKOV3.ipl, but not in OV4, as determined by real-time PCR using a LightCycler. The results indicated survivin transcriptional activity in SKOV3 ipl was 40-fold and 10-fold higher than that of 2 control cell lines, human fibroblasts and human mammary epithelial cells, respectively. The results also showed that, with in vitro analysis of the survivin promoter in an adenoviral context, the luciferase activities were 4- and 5-fold higher in SKOV3ip.1 and OVCAR3 cell lines than the 2 control cell lines, respectively. These cells were infected with AdGL3BSurvivin or AdGL3BCMV. AdGL3Bsurvivin is a vector in which the reporter gene luciferase is driven by the ovarian tumor specific promoter survivin, whereas AdGL3BCMV is a control for normalizing the luciferase activity driven by survivin promoter (set CMV promoter activity to 100%).

To determine survivin promoter activity in ovarian cancer cell lines in vitro and in vivo, luciferase activity driven by survivin promoter are detected as a percentage of that driven by CMV promoter in different ovarian cancer cell lines. Briefly, $5 \times 10^4$ cells are infected with AdGL3Bsurvivin or AdGL3BCMV (M.O.I=100) in a conventional condition. Luciferase activities are measured 48 hours post-infection.

To analysis the distribution of luciferase gene expression in mouse organs, six mice are injected with $10^9$ pfu of AdGL3B-Survivin or AdGL3BCMV via tail vein. Two days later, major organs are harvested, and luciferase activity determined.

Double Targeting for Ovarian Cancer Cells In Vitro and In Vivo

To examine double specific targeting for ovarian cancer cells in vitro, luciferase activity driven by survivin promoter will be determined as a percentage of that driven by CMV promoter in different ovarian cancer cell lines and controls. Briefly, $5 \times 10^4$ ovarian cancer cells are infected with AdGL3BSurvivin or AdGL3BCMV (M.O.I.=100) both pre-incubated with various amount of fusion protein sCAR-EGF (0, 5, 10, 15, 20 mg) at room temperature for 30 min. As a control, sCAR6His is used for blocking the native interaction of CAR. Luciferase activities will be measured 48 hours post-infection.

To examine double targeting in primary ovarian cancers, the experiment described above can be repeated with primary ovarian cancers obtained from 4-5 patients.

To determine double specific targeting for ovarian cancer in vivo, $2 \times 10^7$ cells of SKOV3ipl will be inoculated subcutaneously into flank of BALB/c nu/nu mice. When the tumor reaches a diameter of 6-8-mm, intra-tumor or i.v. injection will be performed with $5 \times 10^8$ pfu of AdGL3BSurvivin or AdGL3BCMV pre-incubated with suitable amount of fusion protein sCAR-EGF. Two days later, the tumor will be resected for luciferase analysis.

The following references were cited herein:

Adachi et al., A midkine promoter-based conditionally replicative adenovirus for treatment of pediatric solid tumors and bone marrow tumor purging. Cancer Res. 61:7882-7888 (2001).

Forsythe et al., Activation of vascular endothelial growth factor gene transcription by hypoxia-inducible factor I. Mol. Cell. Biol. 16:4604-4613 (1996).

Hardy et al., Construction of adenovirus vectors through Cre-lox recombination. J. Virol. 71:1842-1849 (1997).

He et al., A simplified system for generating recombinant adenoviruses. Proc. Natl. Acad. Sci. USA 95:2509-2514 (1998).

Heise et al., Efficacy of a replication-competent adenovirus (ONYX-015) following intratumoral injection: intratumoral spread and distribution effects. Cancer Gene Ther. 6:499-504 (1999).

Koivunen et al., Identification of receptor ligands with phage display peptide libraries. J. Nucl. Med. 40:883-888 (1999).

Krasnykh et al., Generation of recombinant adenovirus vectors with modified fibers for altering viral tropism. J. Virol. 70:6839-6846 (1996).

Ohta et al., Significance of vascular endothelial growth factor messenger RNA expression in primary lung cancer. Clin. Cancer. Res. 2:1411-1416 (1996).

Roelvink et al., Identification of a conserved receptor-binding site on the fiber proteins of CAR-recognizing adenoviridae. Science 286:1568-1571 (1999).

Shinoura et al., Highly augmented cytopathic effect of a fiber-mutant E1B-defective adenovirus for gene therapy of gliomas. Cancer Res. 59:3411-3406 (1999).

Soudais et al., Canine adenovirus type 2 attachment and internalization: coxsackie-adenovirus receptor, alternate receptors, and an RGD-independent pathway. J. Virol. 74:10639-10649 (2000).

Takayama et al., Suppression of tumor angiogenesis and growth by gene transfer of a soluble form of vascular endothelial growth factor receptor into a remote organ. Cancer Res. 60:2169-2177 (2000).

Takayama et al., The levels of integrin avb5 may predict the susceptibility to adenovirus-mediated gene transfer in human lung cancers. Gene Ther. 5:361-368 (1998).

Wickham et al., Increased in vitro and in vivo gene transfer by adenovirus vectors containing chimeric fiber proteins. J. Virol. 71: 8221-8229 (1997).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. An adenoviral vector comprising an adenoviral genome encoding an adenovirus type 5 (Ad5) E1A protein with a deletion consisting of amino acids 122 to 129.

* * * * *